US 12,232,683 B2

(12) United States Patent
Jung et al.

(10) Patent No.: US 12,232,683 B2
(45) Date of Patent: Feb. 25, 2025

(54) DRYING APPARATUS AND METHOD OF CONTROLLING SAME

(71) Applicant: LG ELECTRONICS INC., Seoul (KR)

(72) Inventors: Taeyong Jung, Seoul (KR); Chan Ho Chun, Seoul (KR); Chang Kyu Kim, Seoul (KR); Hye Yong Park, Seoul (KR); Manho Chun, Seoul (KR); Sora Kim, Seoul (KR); DoHyun Jung, Seoul (KR); Taehee Lee, Seoul (KR)

(73) Assignee: LG Electronics Inc., Seoul (KR)

( * ) Notice: Subject to any disclaimer, the term of this patent is extended or adjusted under 35 U.S.C. 154(b) by 672 days.

(21) Appl. No.: 17/560,992

(22) Filed: Dec. 23, 2021

(65) Prior Publication Data
US 2022/0192464 A1 Jun. 23, 2022

(30) Foreign Application Priority Data

Dec. 23, 2020 (KR) .................. 10-2020-0181803
Dec. 23, 2020 (KR) .................. 10-2020-0181804
(Continued)

(51) Int. Cl.
A47L 23/20 (2006.01)
A61L 2/07 (2006.01)
(Continued)

(52) U.S. Cl.
CPC .............. *A47L 23/205* (2013.01); *A61L 2/07* (2013.01); *F26B 9/00* (2013.01); *F26B 21/02* (2013.01); A61L 2202/122 (2013.01)

(58) Field of Classification Search
CPC .... A47L 23/205; A61L 2/07; A61L 2202/122; F26B 9/00; F26B 21/022
(Continued)

(56) References Cited

U.S. PATENT DOCUMENTS 3,299,529 A * 1/1967 Roberts ................. A47L 23/205
219/400
5,546,678 A * 8/1996 Dhaemers ............... F26B 21/02
34/224
(Continued)

FOREIGN PATENT DOCUMENTS

CN 1760593 4/2006
CN 102131440 7/2011
(Continued)

OTHER PUBLICATIONS

Office Action in Taiwanese Office Action Appln. No. 110148280, dated Aug. 1, 2022, 29 pages (with English translation).
(Continued)

*Primary Examiner* — Stephen M Gravini
(74) *Attorney, Agent, or Firm* — Fish & Richardson P.C.

(57) ABSTRACT

A shoe care device includes an inner cabinet, an air supply device that is configured to blow air to an accommodated space of the inner cabinet and includes a plurality of dehumidifying materials separate from one another, and a controller configured to control the air supply device. The air supply device includes a connection path configured to circulate air between an inlet and an outlet of the inner cabinet, and a regeneration path branched from the connection path and configured to guide air having passed through at least one of the dehumidifying materials to a portion of the air supply device other than the inlet. The controller is configured to control the air supply device to selectively open and close at least one of the connection path or the regeneration path based on whether or not at least one of the dehumidifying materials is heated.

20 Claims, 64 Drawing Sheets

(30) Foreign Application Priority Data

Apr. 1, 2021 (KR) ........................ 10-2021-0042900
Jun. 25, 2021 (KR) ........................ 10-2021-0083341

(51) Int. Cl.
*F26B 9/00* (2006.01)
*F26B 21/02* (2006.01)

(58) Field of Classification Search
USPC .......................................................... 34/104
See application file for complete search history.

(56) References Cited

U.S. PATENT DOCUMENTS

| | | | | |
|---|---|---|---|---|
| 5,592,750 | A * | 1/1997 | Eichten | F26B 9/003 |
| | | | | 34/106 |
| 5,852,879 | A * | 12/1998 | Schumaier | F26B 9/003 |
| | | | | 34/80 |
| 7,121,017 | B2 * | 10/2006 | DuRapau | A47L 23/205 |
| | | | | 34/437 |
| 9,464,843 | B2 * | 10/2016 | Karafinka | F26B 9/003 |
| 9,585,498 | B1 * | 3/2017 | Borden | D06F 59/02 |
| 10,197,332 | B2 * | 2/2019 | Hinkey | A47L 23/205 |
| 10,718,565 | B2 * | 7/2020 | Hinkey | F26B 21/006 |
| 10,961,655 | B2 * | 3/2021 | Hinkey | D06F 59/02 |
| 11,408,679 | B2 * | 8/2022 | Ohnari | F26B 25/008 |
| 2011/0000098 | A1 | 1/2011 | Karafinka | |
| 2022/0192464 | A1 * | 6/2022 | Jung | B01D 53/0446 |

FOREIGN PATENT DOCUMENTS

| | | | | |
|---|---|---|---|---|
| CN | 204889181 | | 12/2015 | |
| CN | 205390555 | | 7/2016 | |
| CN | 106222929 | | 12/2016 | |
| CN | 108740003 | | 11/2018 | |
| CN | 114652256 A | * | 6/2022 | ............ A47B 61/04 |
| DE | 3626887 A1 | | 2/1988 | |
| DE | 102020118881 A1 | * | 1/2022 | ............ D06F 58/10 |
| EP | 0627519 A1 | * | 6/1994 | |
| EP | 0777998 B1 | | 6/1997 | |
| JP | H06209894 | | 8/1994 | |
| JP | H06209895 | | 8/1994 | |
| JP | H09108495 | | 4/1997 | |
| JP | H09117598 | | 5/1997 | |
| JP | 2000126500 A | | 5/2000 | |
| JP | 2001227863 | | 8/2001 | |
| JP | 2002000997 A | | 1/2002 | |
| JP | 2005230324 | | 9/2005 | |
| JP | 2020-199239 A | | 12/2020 | |
| KR | 20000009653 | | 2/2000 | |
| KR | 10082620 | | 4/2008 | |
| KR | 1037245 | | 5/2011 | |
| KR | 20150117430 | | 10/2015 | |
| KR | 101579465 | | 12/2015 | |
| TW | I809618 B | * | 12/2021 | |
| WO | WO-2022139419 A1 | * | 6/2022 | ............ A47B 61/04 |

OTHER PUBLICATIONS

Extended European Search Report in European Appln. No. 21215816.6, dated Jun. 3, 2022, 5 pages.
International Search Report in International Appln. No. PCT/KR2021/019528, dated Mar. 29, 2022, 3 pages.
Extended European Search Report in European Appln. No. 23173648.9, mailed on Sep. 25, 2023, 5 pages.
Office Action in Korean Appln. No. 10-2023-7023953, mailed on Jul. 19, 2024, 10 pages (with English Translation).

* cited by examiner

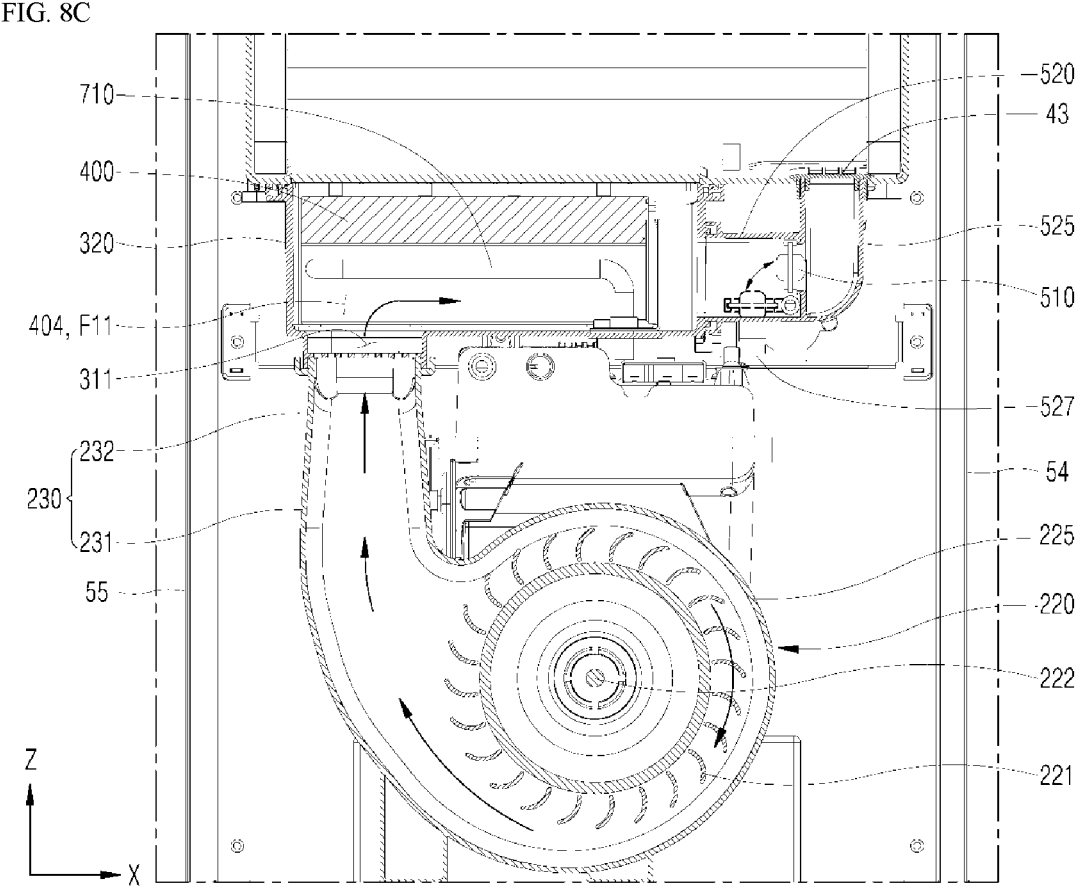

DRYING APPARATUS AND METHOD OF CONTROLLING SAME

CROSS-REFERENCE TO RELATED APPLICATIONS

This present application claims the benefit of priority to Korean Patent Application No. 10-2020-0181803, entitled "Drying Apparatus and Control Method for the same," filed on Dec. 23, 2020, Korean Patent Application No. 10-2020-0181804, entitled "Drying Apparatus and Control Method for the same," filed on Dec. 23, 2020, Korean Patent Application No. 10-2021-0042900, filed on Apr. 1, 2021, and Korean Patent Application No. 10-2021-0083341, entitled "Shoes Care Device," filed on Jun. 25, 2021, the entire disclosures of which are incorporated herein by reference.

TECHNICAL FIELD

The present disclosure relates to a drying apparatus and a method of controlling the drying apparatus.

BACKGROUND

Drying apparatuses may remove moisture or odor from drying objects such as clothes, shoes, etc. The drying apparatuses can be divided into a condensing type drying apparatus and an exhaust type drying apparatus. For example, the condensing type drying apparatus may dry the clothes by condensing the air that has undergone heat exchange with the clothes (air that has absorbed moisture from the clothes) and then resupplying the same to the clothes. The exhaust type drying apparatus may dry the clothes by exhausting the air that has undergone heat exchange with the clothes to the outside of the drying apparatus.

In some cases, the condensing type drying apparatus may be divided into an air-cooled drying apparatus and a water-cooled drying apparatus according to the cooling fluid. The water-cooled drying apparatus may remove moisture from the air by supplying low-temperature cooling water to an air circulation path, and the water-cooled drying apparatus may remove moisture from the air by heat exchange between the air moving along the circulation path and low-temperature external air.

In some cases, in order to increase the condensing efficiency of removing moisture from the air after heat exchange, a drying apparatus may use a dehumidifying material (e.g., zeolite, desiccant, etc.). However, in some cases, humid air generated when the dehumidifying material is regenerated may be exhausted into the room or resupplied to the space in which the drying object is accommodated.

The method of exhausting the humid air generated during the regeneration of the dehumidifying material into the room may have a disadvantage of increasing the indoor humidity, and the method of resupplying the humid air generated during the regeneration of the dehumidifying material into the space for accommodating the drying object may have a disadvantage of supplying even odor particles contained in the moisture to the drying object.

In some cases, shoes may be wet with a wearer's sweat, stained with external contaminants, or wet with rain or snow. Wearing contaminated shoes may make the wearer uncomfortable, and in such a state, bacteria may grow on the shoes, or the shoes may give off odors.

In some cases, a shoe care device may perform a predetermined process on the shoes to eliminate bacteria or odors so that users can wear the shoes in a comfortable state.

For example, the shoe care device may include a main body, an ultraviolet ray-emitting module, a deodorization module, and the like.

In some cases, the shoes may be placed inside a sterilization chamber of the main body, and the ultraviolet ray-emitting module may be operated to remove bacteria and odors from the shoes. Then, the air in the sterilization chamber may be suctioned into a blower pipe, pass through the deodorization module, and then discharge to the outside of the main body through a discharge hole.

In some cases, the deodorization module may include a deodorization column made of materials such as zeolite, activated carbon, charcoal, and the like, where contaminants may be removed from the air discharged from the inside of the main body to the outside thereof by the deodorization column.

For instance, the air, from which moisture has been removed by the deodorization module, may be discharged to the outside of the apparatus for sterilization disposal of shoes.

In some cases, since the air is discharged to the outside of the apparatus for sterilization of shoes, the discharged air may include moisture or odor that is not sufficiently removed before being discharged to the outside of the apparatus, and such air may be discharged to the room in which the user resides.

In some cases, a shoes cabinet may include a main body, a far-infrared ray-emitting unit, a circulation fan, an air circulation passage, a sanitary filter, and the like.

For example, the shoe cabinet may store the shoes and perform sanitary treatment such as dehumidification, sterilization, and deodorization of the shoes by far-infrared rays and a filter while storing the shoes in the shoe cabinet.

In some cases, the sanitary filter may be filled with a material with adsorption properties, such as charcoal and the like, to absorb moisture and filter bacteria while the air passes therethrough, and to serve to capture odor-generating substances.

In some cases, the shoe cabinet may not prevent deterioration of the performance of the sanitary filter to remove moisture or odors, so the shoes may not be effectively processed in the process of using the shoe care device by the user, thereby resulting in unsatisfactory situations.

SUMMARY

The present disclosure describes a shoe care device configured to treat shoes by circulating air.

For example, the present disclosure describes a shoe care device that dehumidifies and deodorizes shoes using a dehumidifying material to refresh the shoes, and regenerates the used dehumidifying material, thereby maintaining appropriate performance of processing shoes.

The present disclosure also describes a shoe care device that has an air circulation structure in which the air inside the inner cabinet where the shoes are placed is dehumidified using a dehumidifying material and in which the dehumidified air is supplied back into the inner cabinet, thereby preventing the user from being exposed to the air used in dehumidification and deodorization of shoes.

The present disclosure further describes a shoe care device that is in the most appropriate mode by reflecting the state of the shoes, which is an object to be processed, or the state of a dehumidifying material, thereby further improving the efficiency of processing shoes.

According to one aspect of the subject matter described in this application, a shoe care device includes an inner cabinet that has an accommodation space configured to accommodate shoes therein, an inlet defined at a first portion of the accommodation space and configured to supply air to the accommodation space, and an outlet defined at a second portion of the accommodation space and configured to suction air from the accommodation space. The shoe care device further includes an air supply device that is configured to blow air to the accommodated space along a plurality of paths, that includes a plurality of dehumidifying materials that are separate from one another and disposed in the plurality of paths, and that is configured to heat the plurality of dehumidifying materials. The shoe care device further includes a controller configured to control the air supply device. The plurality of paths of the air supply device include a connection path configured to circulate air between the inlet and the outlet, and a regeneration path branched from the connection path and configured to guide air having passed through at least one of the plurality of dehumidifying materials to a portion of the air supply device other than the inlet. The controller is configured to control the air supply device to selectively open and close at least one of the connection path or the regeneration path based on whether or not at least one of the plurality of dehumidifying materials is heated.

Implementations according to this aspect can include one or more of the following features. For example, the shoe care device can further a steam generator configured to supply steam to the accommodation space. In some implementations, the controller can be configured to, based on any one of the plurality of dehumidifying materials being heated, control the air supply device in a first operation mode by (i) closing a first portion of the connection path corresponding to a heated dehumidifying material among the plurality of dehumidifying materials to thereby open a first portion of the regeneration path corresponding to the heated dehumidifying material, and (ii) opening a second portion of the connection path corresponding to an unheated dehumidifying material among the plurality of dehumidifying materials to thereby close a second portion of the regeneration path corresponding to the unheated dehumidifying material.

In some examples, the controller can be configured to, in the first operation mode, control the air supply device to alternately heat the plurality of dehumidifying materials one after another. In some examples, the controller can be configured to, in the first operation mode, control the air supply device to supply a first amount of air to the heated dehumidifying material and a second amount of air to the unheated dehumidifying material, where the first amount of air is less than the second amount of air. In some examples, the controller can be configured to, based on none of the plurality of dehumidifying materials being heated, control the air supply device in a second operation mode by opening the connection path to thereby close the regeneration path. In some implementations, the controller can be configured to, based on all of the plurality of dehumidifying materials being heated, control the air supply device in a third operation mode by closing the connection path to thereby open the regeneration path.

In some implementations, the shoe care device can further include a control panel configured to receive an operation signal from a user, and the controller can be configured to, based on the operation signal being received through the control panel, control the air supply device to perform the third operation mode for a predetermined time. In some implementations, the shoe care device can further include a sensor configured to measure an amount of moisture adsorbed in the plurality of dehumidifying materials, and the controller can be configured to control the air supply device to perform the third operation mode until the amount of moisture measured by the sensor becomes less than or equal to a predetermined value.

In some implementations, the air supply device can include a plurality of chambers that are spaced apart from one another and connected to branches of the connection path, respectively, where each of the plurality of chambers accommodates one of the plurality of dehumidifying materials, and a plurality of heaters, where each of the plurality of heaters is disposed at one of the plurality of chambers and configured to heat one of the plurality of dehumidifying materials in the one of the plurality of chambers. Each chamber of the plurality of chambers can define a drying path hole configured to discharge air having passed through the dehumidifying material in the chamber toward the inlet, and a regeneration path hole that is separate from the drying path hole and configured to discharge air having passed through the dehumidifying material in the chamber in a direction other than toward the inlet.

The air supply device can further include a plurality of dampers that are disposed in the plurality of chambers, respectively, and configured to selectively open and close the drying path hole and the regeneration path hole of each the plurality of chambers, where the controller is configured to control the plurality of dampers to selectively open and close the drying path hole and the regeneration path hole of each the plurality of chambers based on operation of at least one of the plurality of heaters. In some examples, the air supply device can further include a condenser connected to the regeneration path holes and configured to condense moisture from air discharged through the regeneration path holes.

In some implementations, the controller can be configured to, based on one of the plurality of heaters operating, (i) control one of the plurality of dampers to close the drying path hole corresponding to an operating heater among the plurality of heaters to thereby open the regeneration path hole corresponding to the operating heater, and (ii) control another of the plurality of dampers to open the drying path hole corresponding to a remaining heater that is not the operating heater among the plurality of heaters to thereby close the regeneration path hole corresponding to the remaining heater. In some examples, the controller can be configured to alternately operate the plurality of heaters one after another.

In some implementations, the controller can be configured to control the plurality of dampers to supply a first amount of air to one of the plurality of chambers corresponding to the operating heater and a second amount of air to another of the plurality of chambers corresponding to the remaining heater, where the first amount of air is less than the second amount of air. In some implementations, an open area of the regeneration path hole can be less than an open area of the drying path hole. In some implementations, the controller can be configured to, based on none of the plurality of heaters operating, control the plurality of dampers to open the drying path holes to thereby close the regeneration path through the regeneration path holes.

In some implementations, the controller can be configured to, based on all of the plurality of heaters operating, control the plurality of dampers to close the drying path holes to thereby open the regeneration path through the regeneration path holes. In some examples, the shoe care device can include a control panel configured to receive an operation signal from a user, and the controller can be configured to, based on the operation signal being received through the control panel, operate all of the plurality of heaters for a predetermined time.

In some implementations, the shoe care device can include a sensor configured to measure an amount of moisture adsorbed in the plurality of dehumidifying materials, and the controller can be configured to operate all of the plurality of heaters until the amount of moisture measured by the sensor becomes less than or equal to a predetermined value.

In some implementations, the air supply device can include a blowing fan connected to the outlet and configured to blow air toward each of the plurality of chambers, and a drain tank connected to the condenser and configured to receive water generated from the condenser.

In some implementations, the shoe care device can be configured to dehumidify and deodorize shoes using a dehumidifying material and regenerate the used dehumidifying material. Specifically, the dehumidifying material can be disposed in an air supplier to capture moisture and bacteria in the blown air, and the dehumidifying material can be regenerated by being heated by the air supplier.

In some implementations, the shoe care device can be configured to have an air circulation structure in which the air used in dehumidification and deodorization of shoes circulates inside the shoe care device. Specifically, the shoe care device can be configured such that a connection path through which air circulates is formed between an inlet and an outlet formed inside an inner cabinet.

In some implementations, the shoe care device can be configured to selectively perform a dehumidification mode using a dehumidifying material or a regeneration mode for the dehumidifying material in consideration of the state of shoes or the state of the dehumidifying material. Specifically, a pair of dehumidifying materials is disposed in an air supply device, and a connection path and a regeneration path are formed in each dehumidifying material so that each of the connection path and the regeneration path is configured to be selectively opened and closed depending on the need for the dehumidification mode and the regeneration mode.

In some implementations, the shoe care device can supply steam into the inner cabinet to perform steam treatment on shoes. In some implementations, in the shoe care device, dehumidification can be performed through any one dehumidifying material among a pair of dehumidifying materials, and regeneration can be performed for the one remaining dehumidifying material. In some implementations, any one of a pair of dehumidifying materials and the remaining one thereof can be alternately dehumidified and regenerated.

In some implementations, the amount of air blown to any one dehumidifying material performing dehumidification can be larger than the amount of air blown to the one remaining dehumidifying material performing regeneration. In some implementations, dehumidification can be simultaneously performed using all of a pair of dehumidifying materials. In some examples, regeneration can be simultaneously performed for all of a pair of dehumidifying materials.

In some implementations, the shoe care device can regenerate all dehumidifying materials for a configured time during the initial operation after an idle period of time. In some examples, when it is detected that the amount of moisture adsorbed into the dehumidifying material exceeds a reference value, the shoe care device can regenerate all dehumidifying materials until the amount of moisture becomes less than or equal to the reference value.

In some implementations, the air supply device can be configured to include a chamber, a heater, a drying path hole, a regeneration path hole, and a damper. In some examples, the air supply device can be configured to further include a condenser.

In some implementations, the open area of the regeneration path hole can be configured to be smaller than the open area of the drying path hole.

In some implementations, since the dehumidifying material is disposed in the air supplier to capture moisture and bacteria in the blown air and since the air supplier heats the dehumidifying material to be regenerated, it can be possible to maintain appropriate performance of processing shoes.

In some implementations, since the connection path through which air circulates is formed between the inlet and the outlet formed inside the inner cabinet, it can be possible to help to prevent the user from being exposed to the air used in dehumidification and deodorization of shoes.

In some implementations, since a pair of dehumidifying materials is disposed in an air supply device and since a connection path and a regeneration path are formed in each dehumidifying material so that each of the connection path and the regeneration path can be selectively opened and closed depending on the need for a dehumidification mode and a regeneration mode, the shoe care device can be operated in an optimal state depending on the situation to further improve the efficiency of processing shoes.

In some implementations, since steam is supplied into the inner cabinet to perform steam treatment on shoes, it can be possible to exert an effect of sterilization by the high temperature steam and a refreshing effect by inflating the material of the shoes or the like.

In some implementations, since dehumidification is performed through any one dehumidifying material among a pair of dehumidifying materials and since regeneration is performed for the one remaining dehumidifying material, it can be possible to simultaneously perform the dehumidification mode and the regeneration mode in the shoe care device.

In some implementations, since any one of a pair of dehumidifying materials and the remaining one thereof are alternately dehumidified and regenerated, the shoe care device can continuously refresh the shoes without interruption.

In some implementations, since the amount of air blown to any one dehumidifying material performing dehumidification is larger than the amount of air blown to the one remaining dehumidifying material performing regeneration, it can be possible to help to prevent dehumidification efficiency from deteriorating even during regeneration.

In some implementations, since dehumidification is simultaneously performed using all of a pair of dehumidifying materials, the shoe care device can refresh the shoes more quickly.

In some implementations, since regeneration can be simultaneously performed for all of a pair of dehumidifying materials, the dehumidifying material can be maintained in a state suitable for dehumidification in the shoe care device.

In some implementations, since all dehumidifying materials are regenerated for a configured time during the initial operation after an idle period of time, the dehumidifying material can be in the appropriate state for dehumidification prior to the operation of the shoe care device for refreshing shoes.

In some implementations, when it is detected that the amount of moisture adsorbed into the dehumidifying material exceeds a reference value, all dehumidifying materials can be regenerated until the amount of moisture becomes less than or equal to the reference value, so the dehumidifying materials can be in the appropriate state for dehumidification even during the operation of the shoe care device for refreshing shoes.

In some implementations, since the air supply device includes a chamber, a heater, a drying path hole, a regeneration path hole, and a damper, the controller can control the damper so as to selectively perform the dehumidification mode and the regeneration mode.

In some implementations, since the air supply device further includes a condenser, it can be possible to condense moisture generated in the process of regenerating the dehumidifying material.

In some implementations, since the open area of the regeneration path hole is configured to be smaller than the open area of the drying path hole, it can possible to help to prevent the dehumidification efficiency from deteriorating during the regeneration even without separately controlling the degree of air distribution by the controller.

Additional scope of applicability of the present disclosure will become apparent from the following detailed description. However, it should be understood that the detailed description and specific implementations such as implementations of the present disclosure are given by way of example only because various changes and modifications within the spirit and scope of the present disclosure can be clearly understood by those skilled in the art.

BRIEF DESCRIPTION OF THE DRAWINGS

The above and other aspects, features, and advantages of the present disclosure will be more apparent from the following detailed description taken in conjunction with the accompanying drawings.

FIG. 8C is a cross-sectional view illustrating a portion of the shoe care device taken along line C-C' in FIG. 7A.

DETAILED DESCRIPTION

Figure 1:
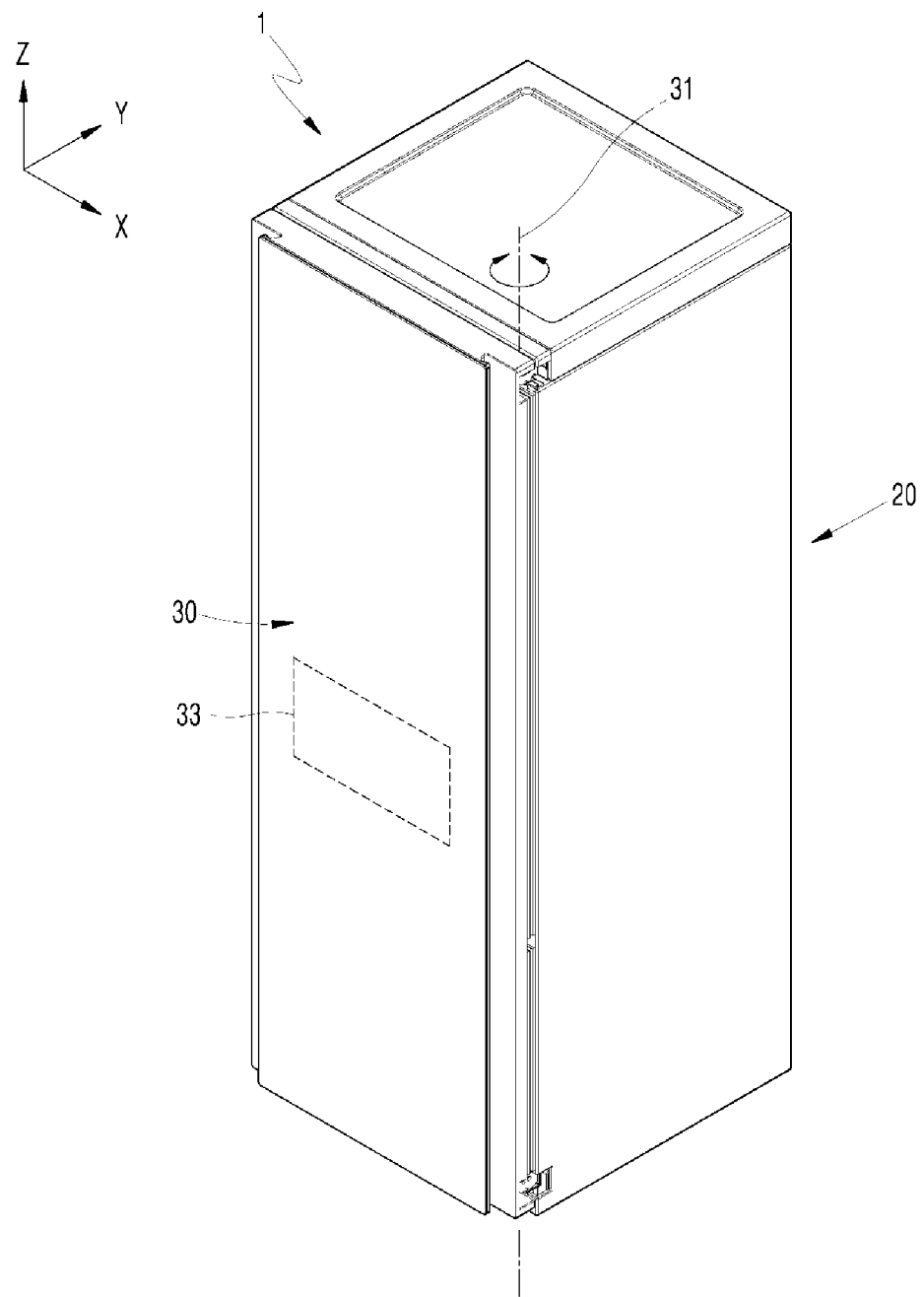
FIG. 1 is a perspective view showing an example of a shoe care device.

Hereinafter, one or more implementations of the present specification will be described in detail with reference to the accompanying drawings, and the same or similar elements are given the same and similar reference numerals, so duplicate descriptions thereof will be omitted.

In the description below, a first direction X, a second direction Y, and a third direction Z described can be directions perpendicular to each other.

The first direction X and the second direction Y can be directions parallel to the horizontal direction, respectively, and the third direction Z can be a direction parallel to the vertical direction. When the first direction X is parallel to the left-right direction, the second direction Y can be parallel to the front-back direction. When the first direction X is parallel to the front-back direction, the second direction Y can be parallel to the left-right direction.

Hereinafter, a drying apparatus will be described, and a shoe care device for processing shoes or a clothing care device for processing clothing will be described as an example of the drying apparatus.

FIG. 1 is a perspective view showing an example of a shoe care device 1.

Figure 2A:
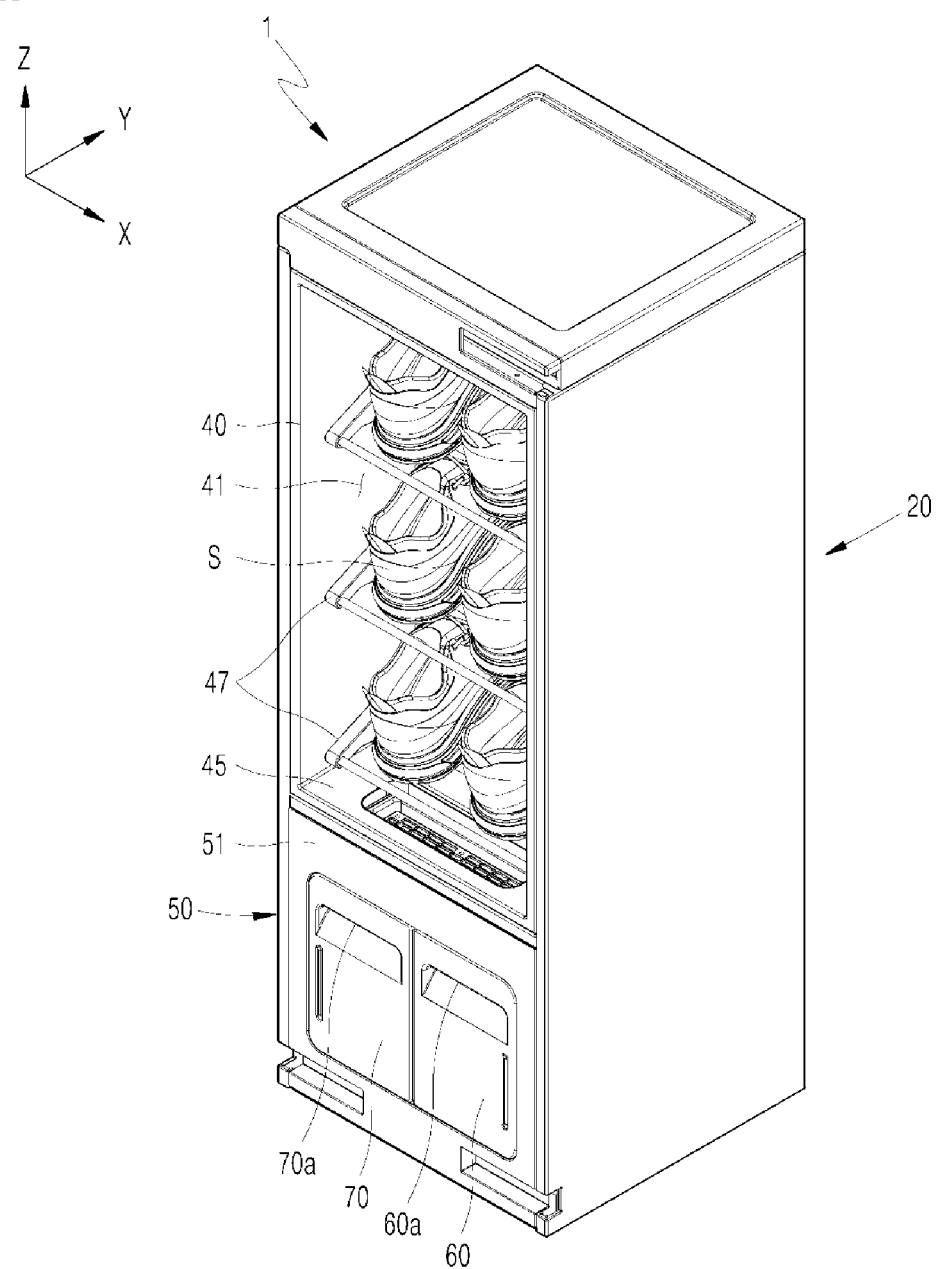
FIG. 2A is a perspective view illustrating the shoe care device in FIG. 1 without a door to show the inside of the shoe care device in FIG. 1.
Figure 2B:
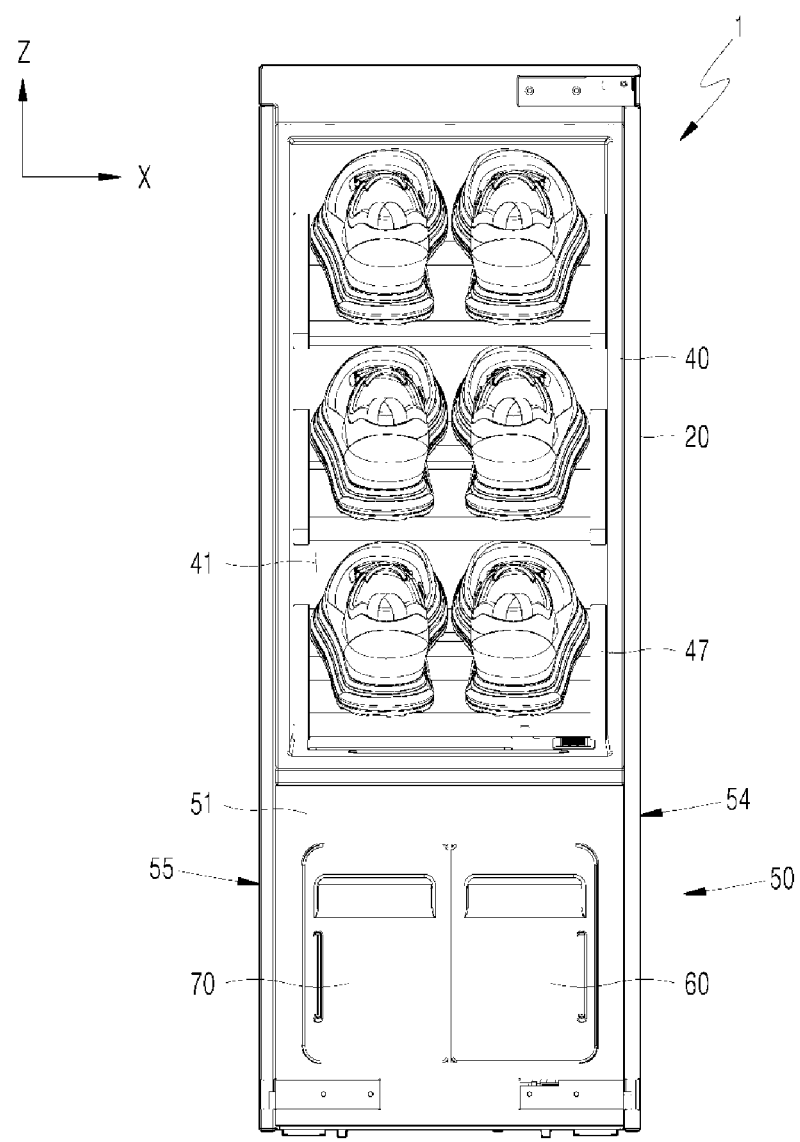
FIG. 2B is a front view illustrating the shoe care device in FIG. 2A.

FIG. 2A is a perspective view illustrating the shoe care device 1 in FIG. 1 from which a door 30 is removed to show the inside of the shoe care device 1 in FIG. 1. FIG. 2B is a front view illustrating the shoe care device 1 in FIG. 2A.

Figure 3A:
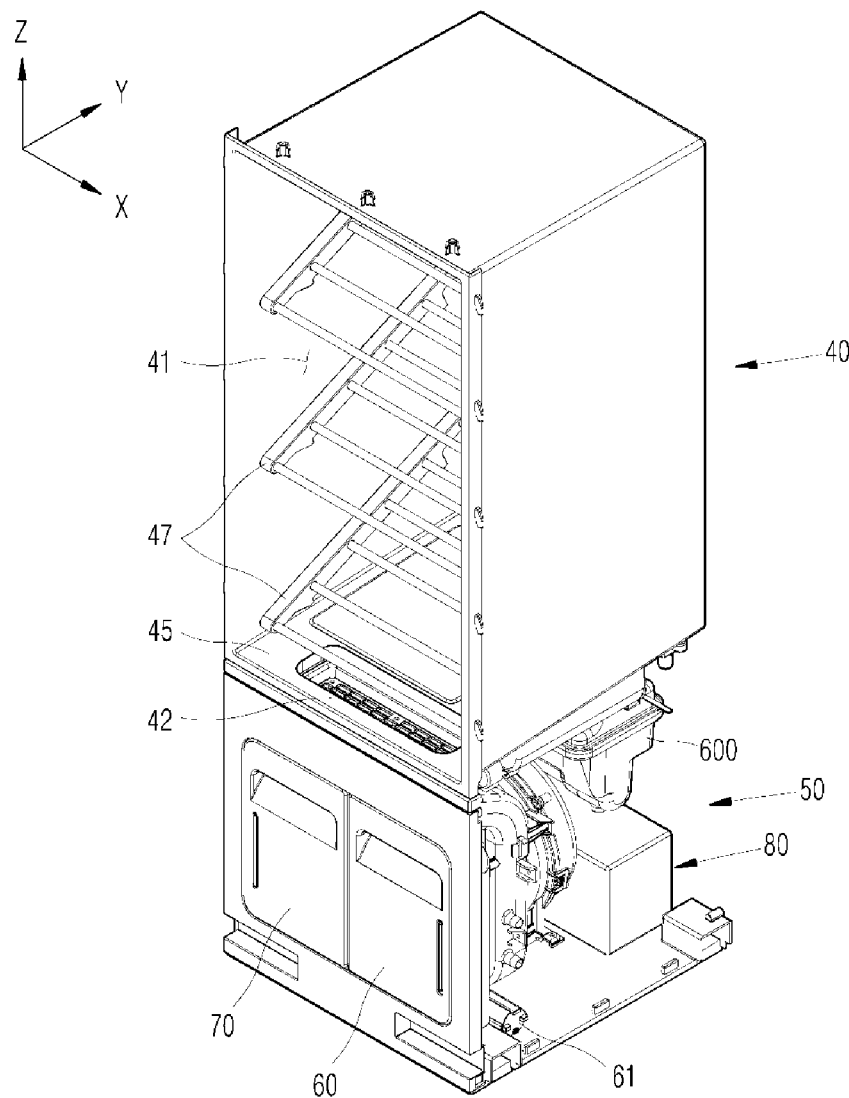
FIG. 3A is a perspective view illustrating the shoe care device without an outer cabinet in FIG. 2A.

FIG. 3A is a perspective view illustrating the state in which an outer cabinet 20 is removed from the shoe care device 1 in FIG. 2A.

Figure 3B:
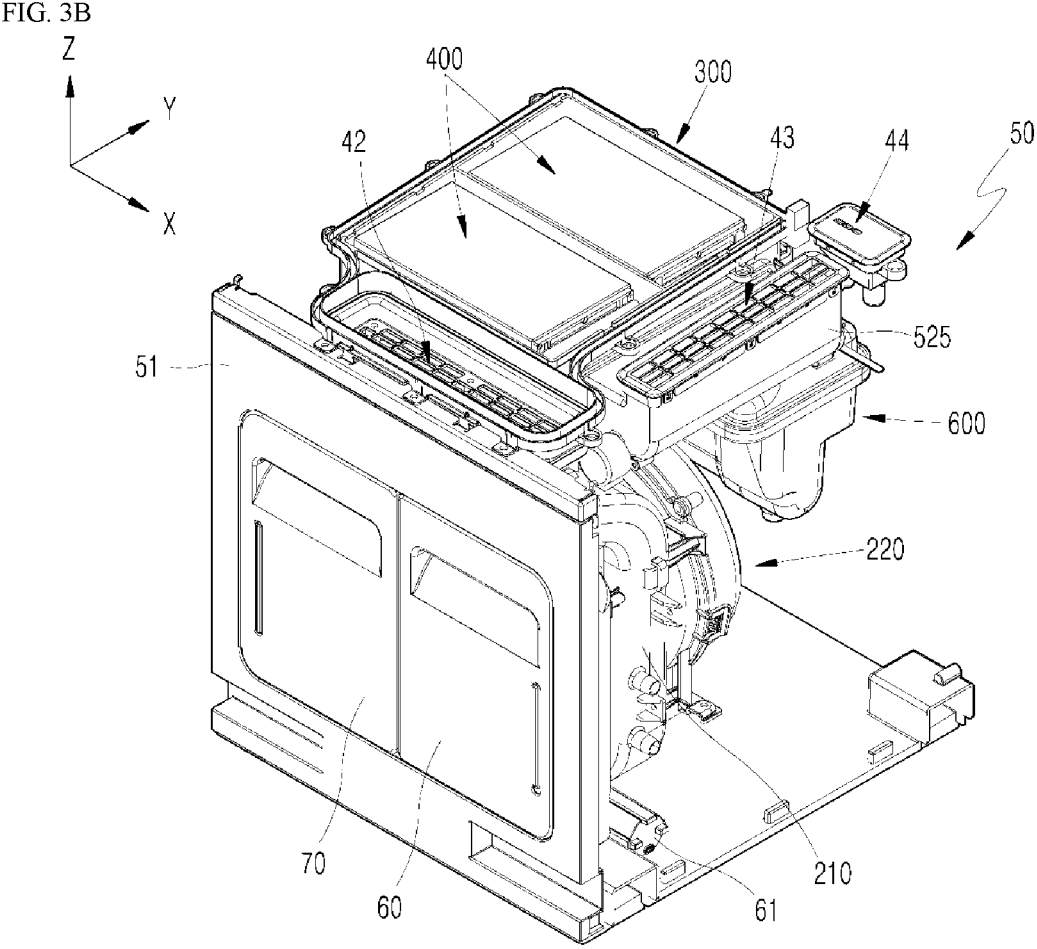
FIG. 3B is a perspective view illustrating an example of a machine room in FIG. 3A.

FIG. 3B is a perspective view illustrating the configurations provided in the machine room 50 in FIG. 3A.

In some implementations, the shoe care device 1 can be configured to include an outer cabinet 20, a door 30, an inner cabinet 40, a machine room 50, and a controller 80. In some examples, the shoe care device 1 can be configured to include a steam generator 600. In some examples, the shoe care device 1 can be configured to include a dehumidifying housing 300, a dehumidifying block 400, and a heater 710. In some examples, the shoe care device 1 can include an outlet 42, an inlet 43 and a connection path F10.

In some implementations, the shoe care device 1 can include a blower 220. In some examples, the shoe care device 1 can include a damper 510, a damper housing 520, a sump 214, a regeneration path F20, and a condenser 800. In some examples, the shoe care device 1 can include a water supply tank 60 and a drain tank 70.

In some implementations, the outer cabinet 20 and the door 30 can define the overall appearance of the shoe care device 1. For instance, the shoe care device 1 can have a hexahedral shape. That is, in the state that the outer cabinet 20 and the door 30 are coupled to each other and that the door 30 is closed, the outer shape of the shoe care device 1 can be configured in the form of a hexahedron.

The door 30 can be configured to open and close the inner space of the shoe care device 1. The door 30 can configure any one surface of the shoe care device 1. The door 30 can configure a left surface or right surface of the shoe care device 1, or can configure the front surface of the shoe care device 1.

Hereinafter, the surface on which the door 30 is formed in the shoe care device 1 will be described as the front surface of the shoe care device 1, unless otherwise specifically stated.

The inner cabinet 40 and the machine room 50 can be provided inside the outer cabinet 20. The outer cabinet 20 can configure outer wall surfaces of the inner cabinet 40 and the machine room 50. In the case where a separate cabinet for the machine room 50 is not provided in the shoe care device 1, the outer cabinet 20 can configure walls that separate the machine room 50 from the outside thereof.

An inner space is provided inside the shoe care device 1 as an accommodation space in which shoes are accommodated. The inner cabinet 40 can be configured in the form of a box, and the accommodation space 41 inside the inner cabinet 40 configures the inner space of the shoe care device 1. That is, the inner cabinet 40 can be configured to accommodate shoes S therein.

The inner cabinet 40 can be configured in the form of a vertically long-shaped box, and a plurality of shoes S can be arranged vertically inside the inner cabinet 40.

The inner cabinet 40 can be in the form of a box having an opening on one side thereof. The opening of the inner cabinet 40 can be closed or opened by the door 30. The inner cabinet 40 can be configured in a form that is open to the front of the shoe care device 1.

The inner cabinet 40 and the machine room 50 can form spaces separated from each other inside the shoe care device 1. The inner cabinet 40 can form a space for accommodating an object to be processed (shoes S), and the machine room 50 can form a space for accommodating elements for operation of the shoe care device 1.

The machine room 50 can be configured to accommodate a connection path F10, a blower 220, a dehumidifying housing 300, a dehumidifying block 400 (and a dehumidifying material 430), a heater 710, a sump 214, a regeneration path F20, a condenser 800, and a steam generator 600. The machine room 50 can be configured to accommodate a water supply tank 60 and a drain tank 70.

Elements that are coupled to or accommodated in the machine room 50 can be fixedly coupled to the machine room 50.

The machine room 50 can be configured to include a first wall 51.

The first wall 51 can configure any one wall surface of the machine room 50. The first wall 51 can be erected in a vertical direction or erected in a substantially vertical direction. In some implementations, the first wall 51 can form a wall surface perpendicular to or inclined to the first direction X. In an example, the first wall 51 can form a wall surface perpendicular to or inclined to the second direction Y.

The first wall 51 can form a front wall surface of the machine room 50, form a left wall of the machine room 50, or form a right wall of the machine room 50.

The water supply tank 60 and the drain tank 70 can be configured in the form of a container for accommodating water.

The water supply tank 60 can be configured to store water, supplied to the inside of the shoe care device 1, therein. In particular, the water supply tank 60 can be configured to store water supplied to the steam generator 600 therein.

In order to supply water from the water supply tank 60 into the shoe care device 1, a water pump (a first water pump 61) can be connected to the water supply tank 60.

The drain tank 70 can be configured to store water discharged from the shoe care device 1 therein. The drain tank 70 can store the water condensed inside the shoe care device 1. The drain tank 70 can be configured to store the water drained from the sump 214.

A water pump (a second water pump 71) can be connected to the drain tank 70 to discharge water to the drain tank 70.

The water supply tank 60 and the drain tank 70 can be coupled to the machine room 50 so as to be exposed to the outside through any one wall surface of the machine room 50.

The water supply tank 60 and the drain tank 70 can be located in the front portion of the machine room 50.

The water supply tank 60 and the drain tank 70 can configure one wall surface of the machine room 50 together with the first wall 51. In the case where the first wall 51 configures the front surface of the machine room 50, the water supply tank 60 and the drain tank 70 can be coupled to the machine room 50 so as to be exposed through the front side of the machine room 50 and so as to be exposed to the outside of the first wall 51.

Since the water supply tank 60 and the drain tank 70 are exposed to the outside of the first wall 51, the user can put water into the water supply tank 60 or discharge water from the drain tank 70.

The water supply tank 60 and the drain tank 70 can be configured to be detachable from the machine room 50. The water supply tank 60 and the drain tank 70 can be attached to and detached from the first wall 51. In order to facilitate attachment and detachment of the water supply tank 60 and the drain tank 70, a handle 60a of the water supply tank can be formed on the outer surface of the water supply tank 60, and a handle 70a of the drain tank can be formed on the outer surface of the drain tank 70.

The water supply tank 60 and the drain tank 70 can be configured to be separated from the machine room 50 in the outer direction of the first wall 51, respectively.

The controller 80 can be configured to control the operations of the respective elements in connection with respective elements constituting the shoe care device 1.

The door 30 can be configured to open and close both the inner cabinet 40 and the machine room 50.

The door 30 can be configured to be rotatable around the rotation axis 31 in the vertical direction in the shoe care device 1. The door 30 can be coupled to the outer cabinet 20 by a hinge. The door 30 can be coupled to the inner cabinet 40 and/or the machine room 50 by a hinge.

The door 30 can be coupled to the inner cabinet 40 and the machine room 50 on the same side as the first wall 51. That is, when the door 30 configures the front surface of the shoe care device 1, the first wall 51 can configure the front surface of the machine room 50, and the door 30 can be located right outside the first wall 51.

The door 30 can be configured to expose or shield the inner cabinet 40, the water supply tank 60, and the drain tank 70. The door 30 can be configured to open and close the front side of the inner cabinet 40, the water supply tank 60, and the drain tank 70.

In the shoe care device 1, the door 30, the water supply tank 60, and the drain tank 70 can be provided on the same side, and when the door 30 is opened, the water supply tank 60 and the drain tank 70 can be exposed and separated from the shoe care device 1.

With the configuration above, even if the left and right sides and the back of the shoe care device 1 are blocked by other items or structures, the door 30 can be opened from the front side of the shoe care device 1, and furthermore, the water supply tank 60 and the drain tank 70 can be separated from or attached to the shoe care device 1.

A control panel 33 for controlling the shoe care device 1 is provided outside the door 30. A control unit (a controller 80) for controlling respective elements of the shoe care device 1 in connection with the control panel 33 can be provided in the inner space of the door 30. The controller 80 can be provided inside the machine room 50.

As shown in FIGS. 1 and 2A, the door 30 can be configured to open and close both the inner cabinet 40 and the machine room 50.

In an example, the door 30 can be configured to open and close only the inner cabinet 40. In this case, the machine room 50 can be configured not to be shielded by the door 30. Furthermore, in this case, the shoe care device 1 can further include a dedicated door of the machine room 50 provided to close the machine room 50 separately from the door 30.

A steam generator 600 is provided in the shoe care device 1 as a device for generating moisture inside the inner cabinet 40. The steam generator 600 can be provided inside the machine room 50. The steam generator 600 can be configured to generate steam and selectively supply moisture and steam into the inner cabinet 40.

Humid air generated by the steam generator 600 ("air" described in the present disclosure can be "air containing moisture") can be supplied to the inner space of the shoe care device 1, and the moisture can circulate through the inner space, thereby providing moisture to the shoes.

In some examples, the shoe care device 1 can be a refresher device for refreshing shoes.

For example, "refreshing" can indicate a process of removing contaminants from shoes, deodorizing shoes, sanitizing shoes, preventing static electricity of shoes, or warming shoes by providing air, heated air, water, mist, steam, etc. to the shoes.

The steam generator 600 can supply steam to the accommodation space 41 of the inner cabinet 40 in which shoes are accommodated to perform steam treatment on the shoes, and furthermore, it is intended to exert a refreshing effect by inflating the shoe material, as well as a sterilization effect by high-temperature steam.

The steam generator 600 can be provided with a separate heater 610 for heating water therein, and can generate steam by heating water and supply the steam to the accommodation space 41 of the inner cabinet 40.

As a water supply source for supplying water to the steam generator 600, an external faucet or the like can be used, or a container-type water supply tank provided on one side of the machine room 50 can be used. The steam generator 600 can generate steam by receiving water from the water supply tank 60.

In the shoe care device 1, the dehumidifying block 400 can be used as a means for dehumidifying air.

The dehumidifying block 400 can be provided in the machine room 50.

The dehumidifying block 400 can be configured to have a predetermined volume. The dehumidifying block 400 can be configured to be porous by itself. A plurality of pores can be formed in the dehumidifying block 400 over the entire volume, and air can pass through the dehumidifying block 400 through the pores. As will be described below, in the case where the dehumidifying block 400 is configured as a combination of a plurality of dehumidifying materials 430, the plurality of dehumidifying materials 430 can be fixed to each other by separate fixing means, or fixed to each other by adhesion.

The dehumidifying block 400 can be configured to include a dehumidifying material.

The dehumidifying material 430 can be configured to include a material capable of lowering humidity by absorbing moisture in the air. The dehumidifying material 430 can be formed of various materials or combinations of materials capable of absorbing or adsorbing moisture in the air, and can have various shapes and structures.

The dehumidifying material 430 can be referred to as "desiccant," "absorbent," or "adsorbent."

The dehumidifying material 430 can be made of a microporous material. The dehumidifying material 430 can be configured to include silica gel, activated carbon, activated alumina (AL2O3), diatomaceous earth, and the like.

In particular, the dehumidifying material 430 can be made of zeolite or can be configured to include zeolite.

Zeolite is a natural and synthetic silicate mineral in which tunnels (or open channels) having a size of about 3 to 10 angstroms (Å) are regularly arranged, and can perform a dehumidification function by adsorbing moisture from the air In the case of heating zeolite, the moisture adsorbed onto the zeolite can be separated into a large amount of vapor. Zeolite can perform a dehumidification function of removing moisture from the air according to the above characteristic thereof, and the moisture adsorbed onto the zeolite can be separated by heating the zeolite, thereby regenerating the zeolite into the state capable of the dehumidification function.

Hereinafter, a description will be made based on that the dehumidifying material 430 is made of zeolite.

Zeolite can be made in the form of a small grain (or stone) having a size (diameter) of several millimeters (mm) to several tens of millimeter (mm), and the dehumidifying material 430 can be a form in which these grains (or stones) are combined. Each of the grains (or stones) can be aggregated or combined to form a single structure.

The heater 710 can be provided on one side of the dehumidifying material (zeolite) 430, and the heater 710 can be selectively heated so that dehumidification by the dehumidifying material 430 or regeneration of the dehumidifying material 430 can be performed.

The dehumidifying material (zeolite) 430 and the heater 710 can be configured as a set. A plurality of sets of the dehumidifying material and the heater can be provided. In the shoe care device 1, in some examples, two sets of the dehumidifying material and the heater 710 can be provided.

Such a set can be referred to as a "drying module" in the shoe care device 1. In the shoe care device 1, a plurality of drying modules can be provided or a pair of drying modules can be provided. In the case where a pair of drying modules is provided in the shoe care device 1, one drying module can be "drying module A," and the other drying module can be "drying module B" (see FIG. 6).

In the shoe care device 1, the drying module A and the drying module B can be configured to operate in different modes. When the drying module A is operated in a dehumidifying mode (the case where the dehumidifying material adsorbs moisture from the air), the drying module B can be operated in a regeneration mode (the case where the moisture adsorbed onto the dehumidifying material is separated by heating the dehumidifying material). In some examples, when the drying module A is operated in a regeneration mode, the drying module B can be operated in a dehumidifying mode.

In some examples, both the drying module A and the drying module B can be operated in a dehumidifying mode, or can be operated in a regeneration mode.

The shoe care device 1 can have a structure in which the dehumidifying block 400 is not separable from the machine room 50.

The shoe care device 1 according to an example of the present disclosure can have a structure in which the dehumidifying block 400 can be separable from the machine room 50. This structure of the shoe care device 1 can provide an advantage in overall maintenance and management of the dehumidifying block 400 and the shoe care device 1.

The dehumidifying block 400 can be repeatedly used by regeneration, but can need to be replaced due to repeated use.

In some implementations, the shoe care device 1 can be configured to enable separation and replacement of the dehumidifying block 400.

Figure 4A:
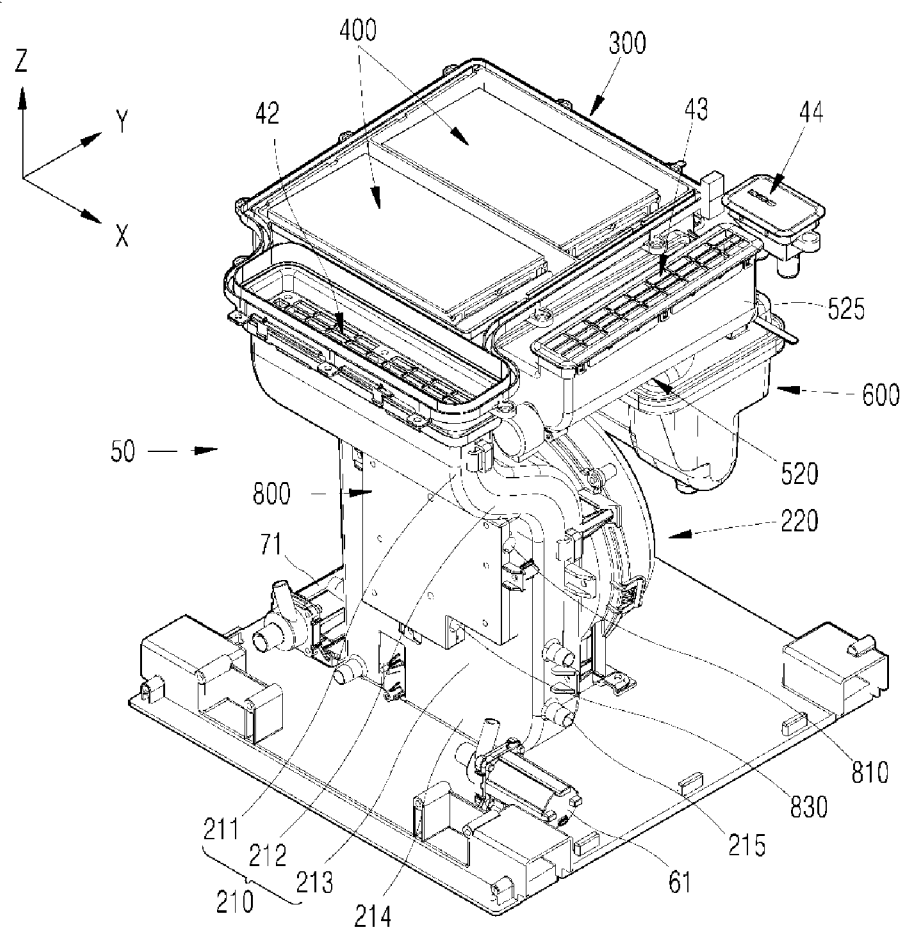
FIG. 4A is a perspective view illustrating the inside of the machine room of the shoe care device shown in FIG. 2A.
Figure 4B:
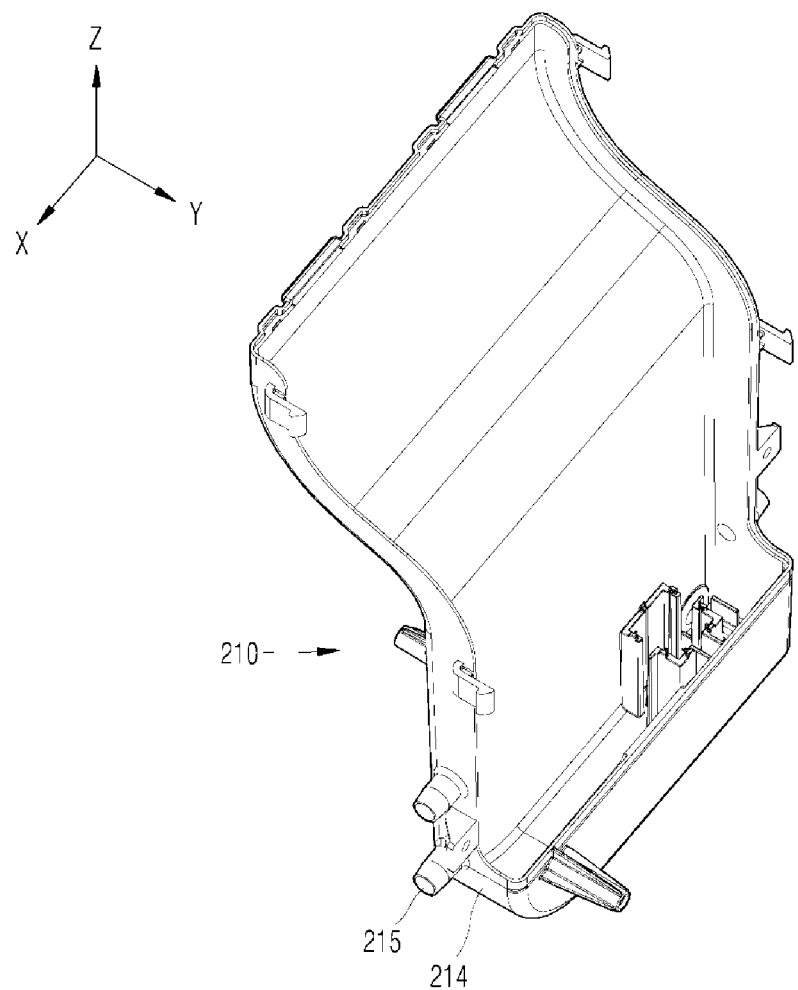
FIG. 4B is a perspective view illustrating a portion of the suction duct in FIG. 4A.

FIG. 4A is a perspective view illustrating the inside of the machine room 50 of the shoe care device 1 shown in FIG. 2A. FIG. 4B is a perspective view illustrating a portion of the suction duct 210 in FIG. 4A.

Figure 5A:
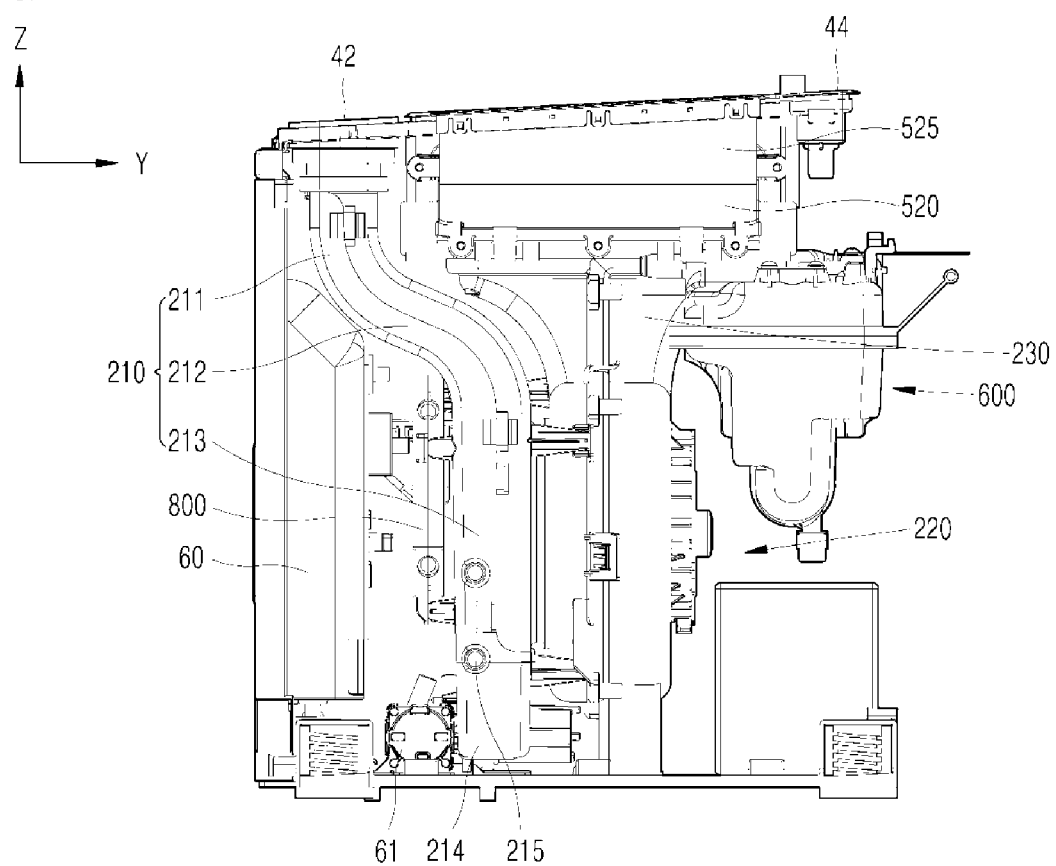
FIGS. 5A and 5B are views illustrating the inside of the machine room of the shoe care device shown in FIG. 2A when viewed from opposite sides.
Figure 5B:
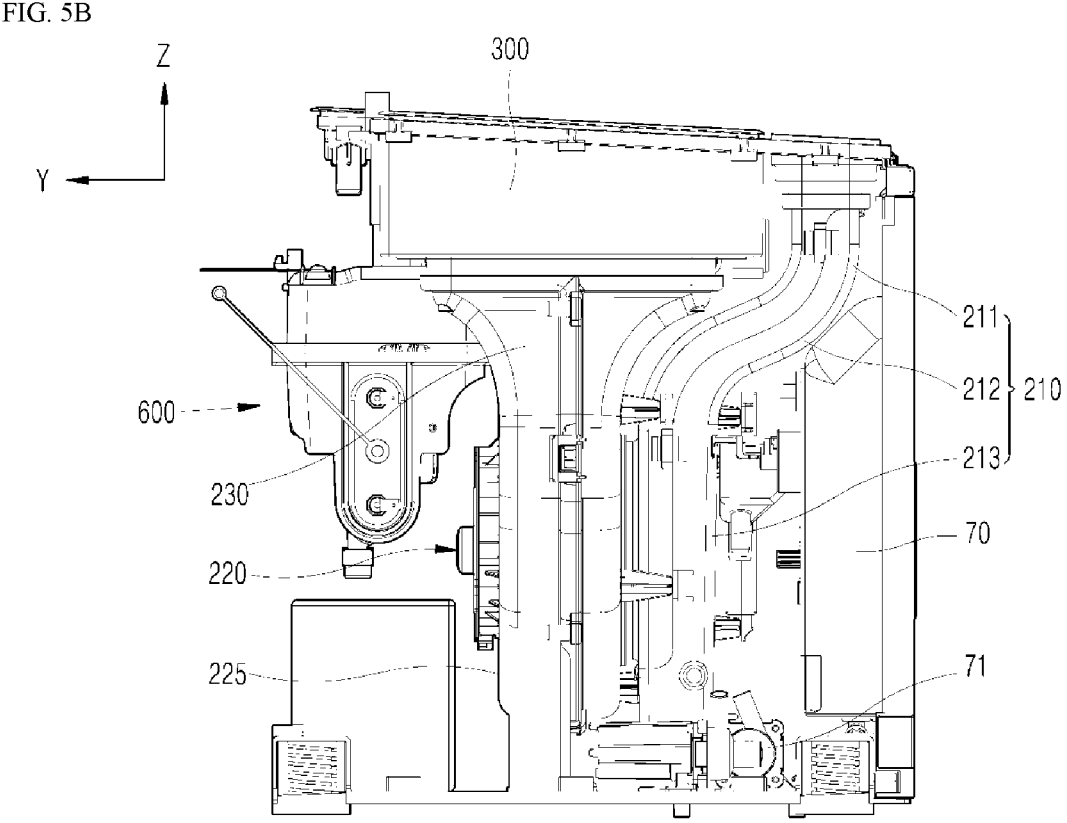

FIGS. 5A and 5B are views illustrating the inside of the machine room 50 of the shoe care device 1 shown in FIG. 2A when viewed from opposite sides.

Figure 6:
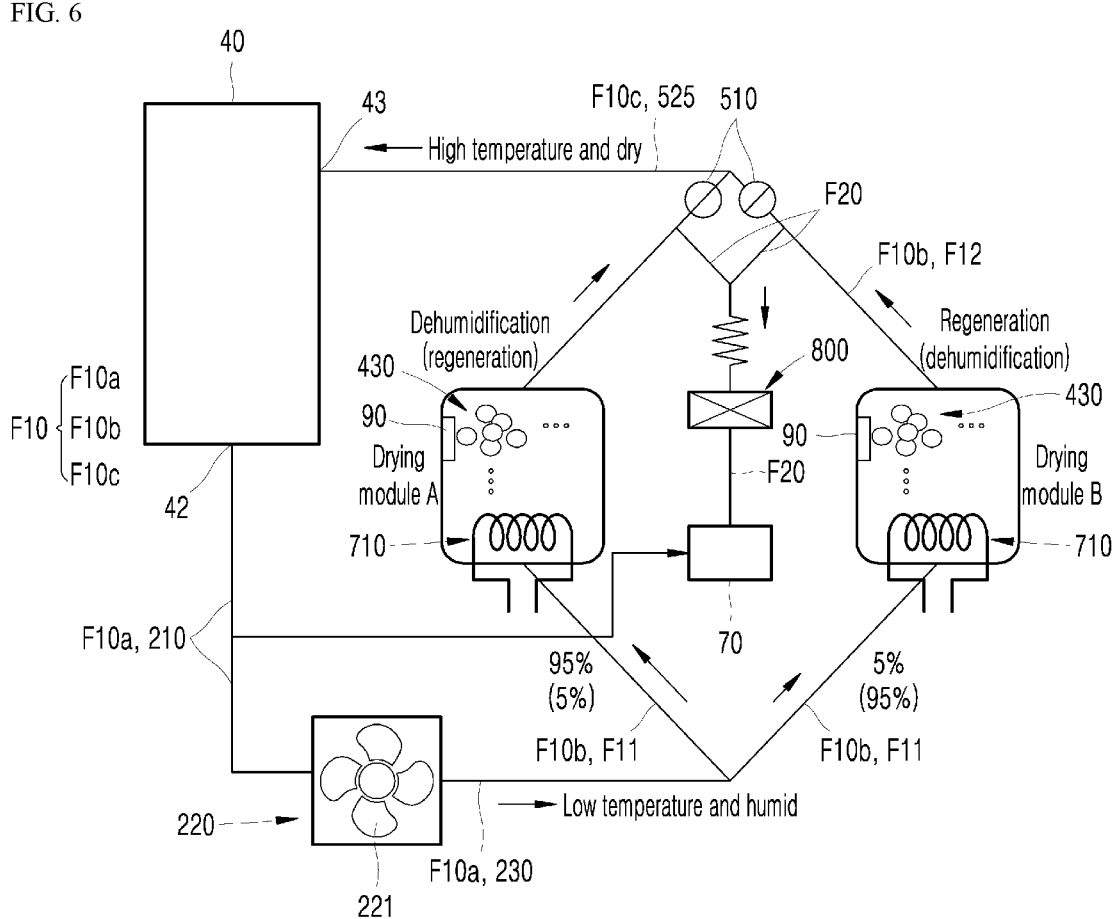
FIG. 6 is a view illustrating an example of a movement cycle of air in the shoe care device.

FIG. 6 is a view illustrating a movement cycle of air in a shoe care device 1

The connection path F10 can form a passage through which the air moves inside the shoe care device 1.

The shoe care device 1 has an air circulation structure in which the air inside the inner cabinet 40 where shoes are placed is sucked into the machine room and is dehumidified using a dehumidifying material 430 and in which the dehumidified air is supplied back into the inner cabinet 40.

The connection path F10 can be used as a means for making such an air circulation structure in the shoe care device 1. All or a portion of the connection path F10 can be configured in the form of a pipe, a tube, a duct, or a combination thereof.

The connection path F10 can define an air moving path connected from the outlet 42 to the inlet 43. That is, the outlet 42 can configure an entrance to the connection path F10, and the inlet 43 can configure an exit of the connection path F10.

The outlet 42 and the inlet 43 can be provided in the inner cabinet 40, and most portions of the connection path F10, excluding the outlet 42 and the inlet 43, can be provided in the machine room 50.

The air inside the inner cabinet 40 can move to the connection path F10 through the outlet 42, and the air that has passed through the connection path F10 can move back to the inner cabinet 40 through the inlet 43. As such airflow is repeated, a circulating airflow can occur in the shoe care device 1.

The dehumidifying block 400 is disposed on the connection path F10. The air moving through the connection path F10 can pass through the dehumidifying block 400, and the dehumidifying block 400 can absorb moisture from the air moving through the connection path (F10) so that the dehumidified air can be supplied to the inner cabinet 40.

The blower 220 is provided inside the machine room 50 to generate airflow in the shoe care device 1.

In particular, the blower 220 makes the flow of air in the connection path F10. That is, the blower 220 causes the air inside the inner cabinet 40 to be sucked into the outlet 42 and the air inside the connection path F10 to be discharged to the inner cabinet 40 through the inlet 43.

Dry air can be supplied into the inner cabinet 40 by the blower 220.

The connection path F10 can be divided into a first section F10a, a second section F10b, and a third section F10c. The first section F10a, the second section F10b, and the third section F10c are sequentially connected to each other to form an air passage. Air in the connection path F10 can pass through the first section F10a, the second section F10b, and the third section F10c in sequence.

The first section F10a can be an upstream section of the connection path F10, which is connected to the outlet 42.

The first section F10a can be connected to the outlet 42 and can be a section in which the blower 220 is located.

The first section F10a can be a section through which humid air moves.

The second section F10b can be a section connected to the first section F10a and in which the dehumidifying block 400 is located. The second section F10b can be a midstream section of the connection path F10.

The second section F10b can be a section in which air is dehumidified by the dehumidifying block 400, or can be a section in which the dehumidifying block 400 (the dehumidifying material 430) is regenerated.

The third section F10c can be a downstream section of the connection path F10, which connects the second section F10b and the inlet 43.

The third section F10c can be a section through which dry air, from which moisture has been removed, moves.

The connection path F10 can be configured to include a suction duct 210, a blowing duct 230, and a discharge duct 525. The suction duct 210, the blowing duct 230, and the discharge duct 525 can be accommodated in the machine room 50.

The suction duct 210 configures a portion of the connection path F10. The suction duct 210 can be connected to the outlet 42 to suck air from the inner cabinet 40.

The sump 214 has a structure for accommodating water. The sump 214 is positioned below the dehumidifying material 430.

The sump 214 can be formed integrally with the suction duct 210. In some implementations, the lowermost portion of the suction duct 210 can have a container structure capable of storing water, and the lower portion of the suction duct 210 in the container structure (the lowermost portion of the lower duct 213) can be a sump 214.

A sump hole 215 forming an entrance, through which condensate water flows into the sump 214, is formed on the outer edge of the sump 214.

The air introduced into the suction duct 210 can contain a relatively large amount of moisture in the process of refreshing shoes, and some of the air introduced into the suction duct 210 can be condensed in the suction duct 210. In addition, condensate water inside the inner cabinet 40 can be sucked into the suction duct 210 together with the air. In this case, the condensate water can fall to the lower portion of the suction duct 210, move to the sump 214 formed integrally with the suction duct 210 to be collected, and can then be discharged to the drain tank or to the outside, or can be transported to the steam generator 600 or the like.

As described above, the shoe care device 1 can facilitate management and discharge of condensate water.

The blowing duct 230 configures a portion of the connection path F10. The blowing duct 230 configures a passage through which air is supplied to the dehumidifying material 430. The blowing duct 230 configures a passage through which the air passing through the blower 220 moves toward the first path F11. The blowing duct 230 extends from the blower 220 to be connected to the housing inlet 311. The blowing duct 230 can extend upwards from the blower 220 to be connected to the housing inlet 311.

The blower 220 can be connected between the suction duct 210 and the blowing duct 230, and a blowing fan 221 can be provided inside the blower 220. Air can be sucked from the inner cabinet 40 and the sucked air can be blown toward the blowing duct 230 by the operation of the blower 220 (the blowing fan 221).

The suction duct 210, the blower 220, and the blowing duct 230 can together form the first section F10a.

The blowing duct 230 can be connected to one side of the dehumidifying housing 300 accommodating the dehumidifying material 430 so that the air blown through the blowing duct 230 can come into contact with the dehumidifying material 430. Accordingly, moisture is removed from the air in contact with the dehumidifying material 430.

The dehumidifying housing 300 and the dehumidifying block 400 can together form the second section F10b.

The damper housing 520 can form the discharge duct 525.

The air passing through the dehumidifying housing 300 can be blown toward the discharge duct 525 of the damper housing 520, which is connected to the opposite side of the dehumidifying housing 300.

The damper housing 520 and the discharge duct 525 can form the third section F10c.

In some implementations, the damper 510 can be configured in the form of a damper valve.

The damper 510 can be configured to open the regeneration path F20 while closing the third section F10c, or open the third section F10c while closing the regeneration path F20.

A damper housing 520 is configured to accommodate the damper 510.

A regeneration path hole 527 forming an entrance to the regeneration path F20 is formed on the bottom of the damper housing 520.

The damper 510 can be configured to selectively shield the inside of the damper housing 520 and the regeneration path hole 527. The damper 510 can be configured to selectively seal the inside of the damper housing 520 and the regeneration path hole 527.

The dry air blown into the discharge duct 525 of the damper housing 520 can flow back into the inner cabinet 40 through the inlet 43 to refresh the shoes.

As described above, the air inside the inner cabinet 40 passes through the outlet 42, the suction duct 210, the blower 220, the blowing duct 230, the dehumidifying housing 300

(and the dehumidifying block 400), the discharge duct 525 of the damper housing 520, and the inlet 43, in sequence, into the connection path F10.

The damper 510 is provided inside the damper housing 520 and controls the movement path of the air passing through the dehumidifying material 430. Upon operation of the damper 510, the air passing through the dehumidifying material 430 can move into the inner cabinet 40 through the inlet 43, or can move to the regeneration path F20.

The damper 510 can be configured to selectively close any one of the discharge duct 525 and the regeneration path F20. In the case where the damper 510 opens the discharge duct 525 while closing the regeneration path F20, the air passing through the dehumidifying material 430 can flow into the inner cabinet 40 through the inlet 43, and in the case where the damper 510 opens the regeneration path F20 while closing the discharge duct 525, the air passing through the dehumidifying material 430 can be condensed while moving through the regeneration path F20.

The moisture generated in the process of regenerating the dehumidifying material needs to be discharged through a path separated from the connection path (F10) (the third section F10c), which is the path through which dry air flows. Accordingly, the shoe care device 1 is configured to include the regeneration path F20, and when the dehumidifying material (zeolite) 430 is regenerated, the air passing through the dehumidifying material 430 moves through the regeneration path F20, instead of being blown to the discharge duct 525.

The regeneration path F20 diverges from the connection path F10. The regeneration path F20 can diverge from the third section F10c of the connection path F10. The regeneration path F20 leads to the sump 214.

The regeneration path F20 configures a path through which air passing through the dehumidifying material 430 and/or condensed water flows when the dehumidifying material 430 is regenerated. The entire regeneration path F20 can be configured in the form of a pipe, a tube, a duct, or a combination thereof.

The moisture separated from the dehumidifying material 430 can move to the condenser 800 together with the air moving through the regeneration path F20 and can then be condensed. In addition, the condensate water condensed in the condenser 800 can move to the lower portion of the suction duct 210 through the regeneration path F20, can be collected at the lower portion of the suction duct 210, and can then be discharged to the drain tank 70 or to the outside or transported to the steam generator 600.

The regeneration path F20 can be configured such that the height thereof is gradually reduced from the point connected to the connection path F10 to the point connected to the sump 214.

The cross-sectional area of the inside of the damper housing 520 is configured to be greater than the cross-sectional area of the regeneration path hole 527.

The cross-sectional area of the inside of the damper housing 520 and the cross-sectional area of the discharge duct 525 can be configured to be greater than the cross-sectional area of the regeneration path hole 527. In some implementations, the cross-sectional area of the inside of the damper housing 520 and the cross-sectional area of the discharge duct 525 can be configured to be double the cross-sectional area of the regeneration path hole 527 or more. In an example, in the case where the cross-sectional area of the inside of the damper housing 520 and the relative cross-sectional area of the discharge duct 525 are 10 cm$^2$, respectively, the relative cross-sectional area of the regeneration path hole 527 can be 0.5 to 2 cm$^2$.

Accordingly, the amount of moving air per unit time in the case where the damper 510 closes the regeneration path hole 527 and opens the inside (the discharge duct 525) of the damper housing 520 is much larger than the amount of moving air per unit time in the case where the damper 510 opens the regeneration path hole 527 and closes the inside (the discharge duct 525) of the damper housing 520.

As described above, in the case where the cross-sectional areas of the inside of the damper housing 520 and the discharge duct 525 are much greater than the cross-sectional area of the regeneration path hole 527, as shown in FIG. 6, if the damper 510 closes the regeneration path hole 527 and opens the discharge duct 525 in the drying module A and if the damper 510 opens the regeneration path hole 527 and closes the discharge duct 525 in the drying module B, most of the air (e.g., 95%) can flow to the drying module A, and only a small fraction (e.g., 5%) of the air can flow to drying module B in the second section F10b. In this case, the drying module A can operate in a dehumidifying mode and drying module B can operate in a regeneration mode.

In some examples, in FIG. 6, if the damper 510 opens the regeneration path hole 527 and closes the discharge duct 525 in the drying module A and if the damper 510 closes the regeneration path hole 527 and opens the discharge duct 525 in the drying module B, most of the air (e.g., 95%) can flow to the drying module B, and only a small fraction (e.g., 5%) of the air can flow to drying module A in the second section F10b. In this case, the drying module B can operate in a dehumidifying mode and drying module A can operate in a regeneration mode.

The shoe care device 1 can have various shapes and structures depending on the usage conditions thereof. The shoe care device 1 can be formed in a hexahedron shape that is long in the vertical direction. This form enables the shoe care device 1 to be installed and used in a relatively narrow space in the vertical direction, and also causes the shoe care device 1 to be naturally arranged with the existing shoe cabinet.

The inner cabinet 40 can have any shape and structure as long as shoes can be received in the accommodation space 41.

The machine room 50 can be located below the inner cabinet 40 (the inner space). This structure makes it suitable for the shoe care device 1 to be formed in a hexahedral shape that is long in the vertical direction, and is advantageous for the convenience of use of the inner cabinet 40.

A rack 47 on which the shoes S are mounted can be provided in the inside of an accommodation space 41 (an inner space) of the inner cabinet 40. A plurality of racks 47 can be provided, and the respective racks 47 can be arranged vertically.

The dry air and steam supplied to the accommodation space 41 of the inner cabinet 40 tend to rise. In the shoe care device 1, the machine room 50 can be located below the inner cabinet 40, and accordingly, the dry air and steam can naturally move upwards from the machine room 50 toward the inner cabinet 40, so that the dry air and steam can be effectively supplied.

In the shoe care device 1, zeolite effective for dehumidification, deodorization, and humidification can be disposed in the machine room 50, and the air that has passed through the zeolite can flow back into the inner cabinet 40 to circulate through the connection path F10, and condensate water can be discharged through the regeneration path F20 when the zeolite is regenerated, thereby effectively managing the shoes.

The dehumidifying block 400 can have a predetermined length in the first direction X. The dehumidifying block 400 can have a length d1 in the first direction X longer than a length d2 in the second direction Y and a length d3 in the third direction Z. Here, the first direction X can indicate the longitudinal direction of the dehumidifying block 400 (see FIG. 13A).

The first direction X can be parallel to the horizontal direction or can be substantially parallel to the horizontal direction.

The first direction X can be the direction directed from the dehumidifying block 400 to the inlet 43.

As described above, the shoe care device 1 can have a substantially hexahedral shape, and the surface of the shoe care device 1, on which the door 30 is formed, can be the front surface of the shoe care device 1.

In some implementations, the first direction X can be the direction directed from the front of the shoe care device 1 to the rear thereof. In an example, the first direction X can be a left-to-right direction of the shoe care device 1, or can be a right-to-left direction of the shoe care device 1.

Figure 7A:
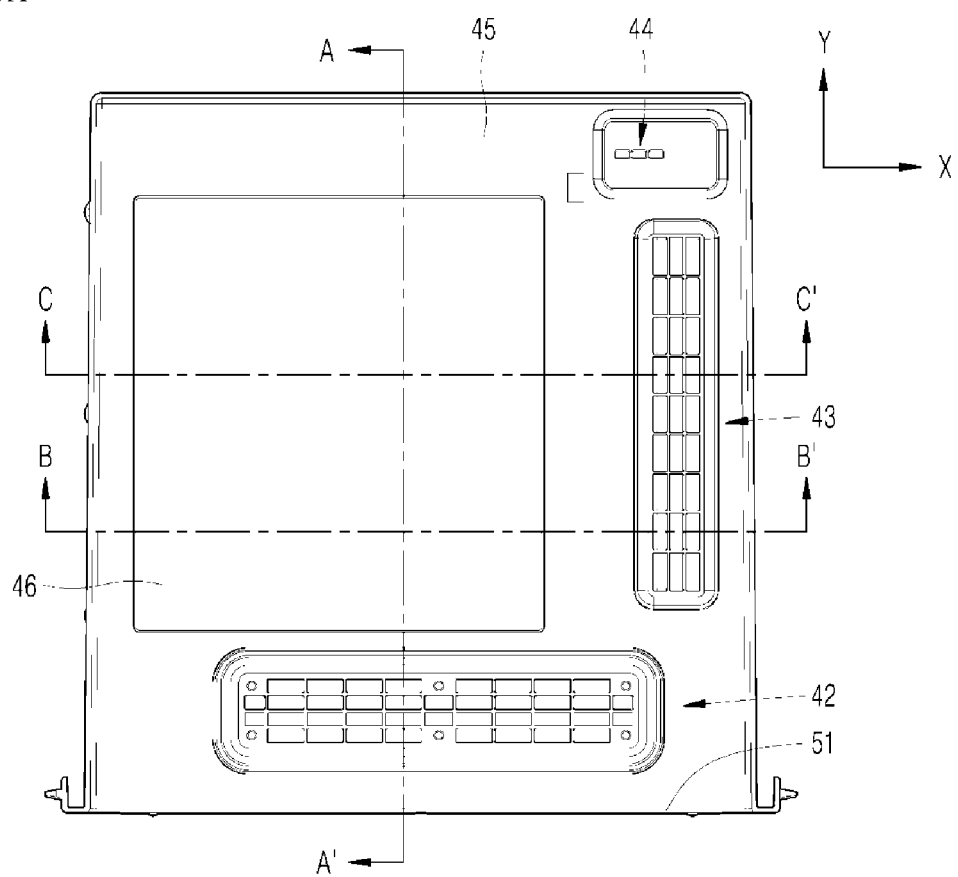
FIG. 7A is a view illustrating an example of a bottom of an inner cabinet of the shoe care device shown in FIG. 2A.

FIG. 7A is a view illustrating a bottom of an inner cabinet 40 of the shoe care device 1 shown in FIG. 2A.

Figure 7B:
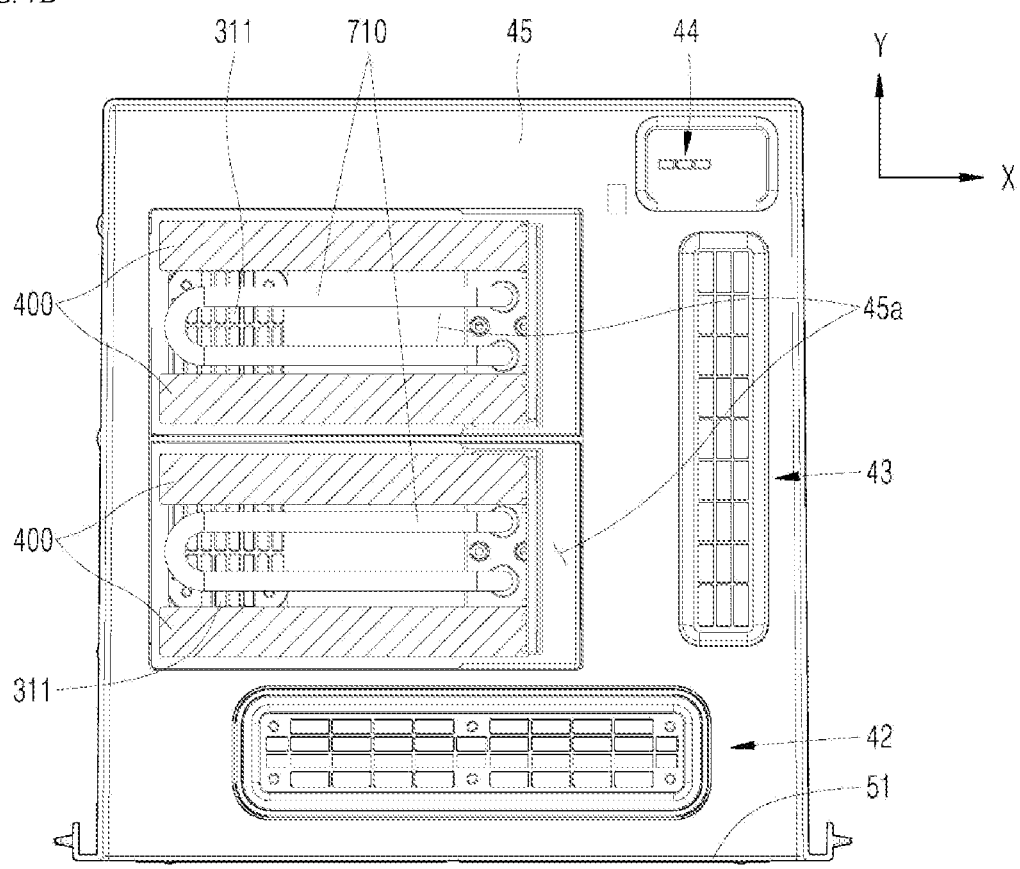
FIG. 7B is a view illustrating an example state in which a dehumidifying material cover is removed from the cabinet bottom plate in FIG. 7A, in which the dehumidifying block is shown in a cross-sectional view from which a ceiling part is deleted.

FIG. 7B is a view illustrating the state in which a dehumidifying material cover 46 is removed from the cabinet bottom plate 45 in FIG. 7A, in which the dehumidifying block 400 is shown in a cross-sectional view from which a ceiling part 401 is removed.

The inner cabinet 40 can be configured to include a cabinet bottom plate 45 forming the bottom thereof.

The cabinet bottom plate 45 can be the boundary of the inner cabinet 40 and the machine room 50. The cabinet bottom plate 45 can have a rectangular shape.

The cabinet bottom plate 45 can be configured to be parallel to the horizontal direction.

Alternatively, the cabinet bottom plate 45 can be configured to be inclined to either side. In this case, water (e.g., the condensate water) on the upper surface of the cabinet bottom plate 45 can flow in any direction along the inclination.

In some implementations, the cabinet bottom plate 45 can be configured such that the front thereof is inclined downwards.

In an example, the cabinet bottom plate 45 can be configured to be inclined downwards to the left, or can be configured to be inclined downwards to the right.

The cabinet bottom plate 45 can configured to be inclined upwards along the first direction X, or the cabinet bottom plate 45 can be configured to be inclined upwards along the second direction Y.

A steam hole 44 can be formed in the cabinet bottom plate 45. The steam hole 44 can be connected to the steam generator 600 by a pipe, a hose, a duct, or the like, and steam of the steam generator 600 can be discharged into the inner cabinet 40 through the steam hole 44.

The shoe care device 1 can be configured to include a dehumidifying material cover 46.

The dehumidifying material cover 46 configures a portion of the cabinet bottom plate 45, which is the bottom of the inner cabinet 40. In addition, the dehumidifying material cover 46 can be detachably coupled to the cabinet bottom plate 45 of the inner cabinet 40, or can be connected to the cabinet bottom plate 45 by a hinge.

A dehumidifying material cover 46 can be formed in the middle of the cabinet bottom plate 45.

In the cabinet bottom plate 45, a bottom hole 45a can be formed as an opening having a shape and size corresponding to the dehumidifying material cover 46. The dehumidifying material cover 46 can be configured to open and close the bottom hole 45a. The dehumidifying material cover 46 can be at least partially removable from the cabinet bottom plate 45. In some implementations, the dehumidifying material cover 46 can be completely separated from the cabinet bottom plate 45, thereby opening the bottom hole 45a, and in an example, the dehumidifying material cover 46 can rotate about a hinge axis, thereby opening the bottom hole 45a. The dehumidifying block 400 can be inserted into or drawn out of the machine room 50 through the bottom hole 45a as an opening.

In addition, when the dehumidifying material cover 46 is separated from the cabinet bottom plate 45, the dehumidifying housing 300 positioned under the cabinet bottom plate 45 can be exposed through the bottom hole 45a, so that the dehumidifying block 400 can be placed inside the dehumidifying housing 300 or the dehumidifying block 400 can be separated from the dehumidifying housing 300.

The dehumidifying material cover 46 and the bottom hole can have any size and shape as long as insertion and taking out of the dehumidifying block 400 are possible.

The dehumidifying material cover 46 can be formed in a rectangular plate shape.

The length of the dehumidifying material cover 46 can be equal to or greater than the length of the dehumidifying block 400 in the first direction X, and the length of the dehumidifying material cover 46 can be equal to or greater than the length of the dehumidifying block 400 in the second direction Y.

In the case where a pair of dehumidifying blocks 400 is provided, a pair of dehumidifying material covers 46 can be provided to individually shield or open each dehumidifying block 400, or one dehumidifying material cover 46 can be provided to shield or open all of the pair of dehumidifying blocks 400.

The dehumidifying material cover 46 can be configured to shield the dehumidifying block 400 to be spaced apart therefrom. A space between the dehumidifying material cover 46 and the dehumidifying block 400 can form a second path F12.

As described above, the outlet 42, which is a hole through which the air is sucked from the inner cabinet 40, can configure the beginning of the connection path F10. The outlet 42 can be formed on the bottom (the cabinet bottom plate 45) of the inner cabinet 40 or can be formed adjacent to the bottom of the inner cabinet 40.

A mesh such as a grid type, a screen type, or the like can be provided in the outlet 42.

The outlet 42 can be formed parallel to the first direction X. That is, the outlet 42 can be configured in the form of a long slot on the cabinet bottom plate 45 along the first direction X. The outlet 42 can be disposed parallel to the dehumidifying block 400.

In some examples, the outlet 42 can be formed at the edge of the cabinet bottom plate 45. In some examples, the outlet 42 can be formed along the first direction X at the edge of the cabinet bottom plate 45. In some examples, the outlet 42 can be formed in the front portion or the rear portion of the cabinet bottom plate 45 in the second direction Y.

The outlet 42 can be located on the cabinet bottom plate 45 to be relatively close to the door 30. That is, the outlet 42 can be positioned relatively at the front of the cabinet bottom plate 45.

As described above, the inlet 43, which is a hole through which air is discharged into the inner cabinet 40, can configure the end portion of the connection path F10. The inlet 43 can be formed at the bottom (the cabinet bottom plate 45) of the inner cabinet 40 or can be formed adjacent to the bottom of the inner cabinet 40.

The inlet 43 can be formed along the second direction Y perpendicular to the first direction X at the edge of the bottom of the inner cabinet 40. The inlet 43 can be configured in the form of a long slot in one direction.

A nesh such as a grid type, a screen type, or the like can be provided in the inlet 43.

When the outlet 42 is located at the front of the bottom of the inner cabinet 40, the inlet 43 can be located in the left or right portion of the bottom of the inner cabinet 40. When the outlet 42 is located in the left or right portion of the bottom of the inner cabinet 40, the inlet 43 can be located at the rear of the bottom of the inner cabinet 40.

The steam hole 44 can be located on the side opposite the outlet 42 and close to the inlet 43 on the bottom of the inner cabinet 40. That is, the steam hole 44 can be located relatively far from the outlet 42 and relatively close to the inlet 43.

When the outlet 42 is formed at the front of the bottom of the inner cabinet 40 and when the inlet 43 is formed in the right portion of the bottom of the inner cabinet 40, the steam hole 44 can be formed on the bottom of the inner cabinet 40 so as to be close to the right side at the rear thereof (see FIGS. 7A and 7B).

Accordingly, the steam discharged from the steam hole 44 can sufficiently move to be dispersed throughout the inside of the inner cabinet 40, instead of being directly sucked into the outlet 42, and, in particular, since it is located adjacent to the inlet 43, the steam can be more strongly discharged into the inner cabinet 40 by the flow (force) of the air discharged from the inlet 43 so that the steam can be supplied to the entire space inside the inner cabinet 40.

Figure 8A:
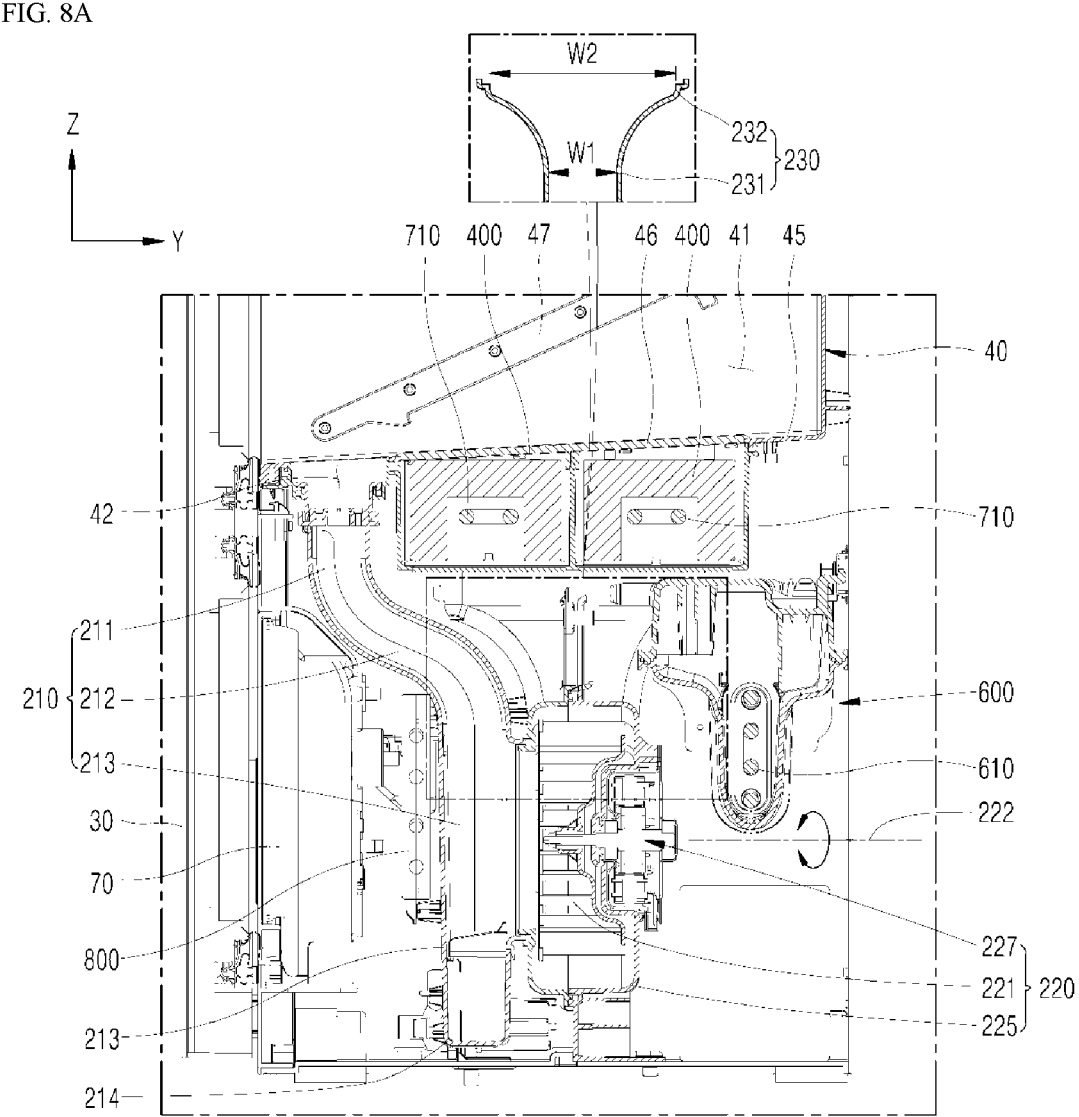
FIG. 8A is a cross-sectional view illustrating a portion of the shoe care device taken along line A-A' in FIG. 7A, in which an example of a blowing duct is shown as a separate cross-sectional view.
Figure 8B:
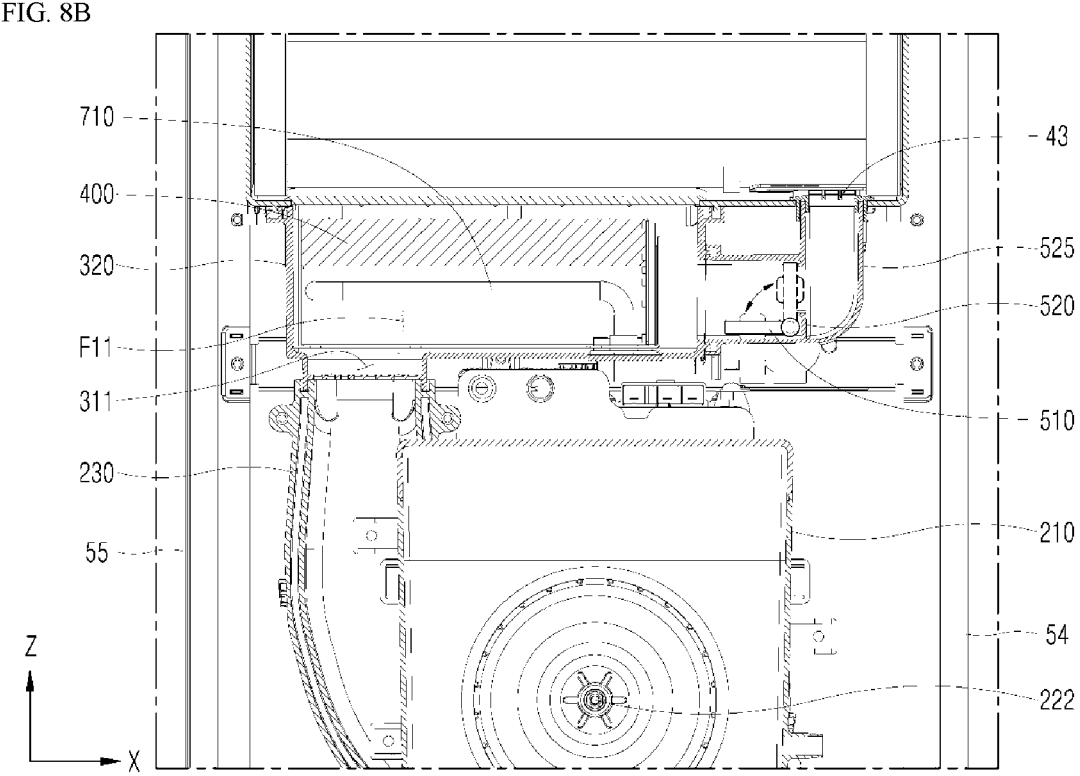
FIG. 8B is a cross-sectional view illustrating a portion of the shoe care device taken along line B-B' in FIG. 7A.

FIG. 8A is a cross-sectional view illustrating a portion of the shoe care device 1 taken along line A-A' in FIG. 7A, in which a blowing duct 230 is shown as a separate cross-sectional view, FIG. 8B is a cross-sectional view illustrating a portion of the shoe care device 1 taken along line B-B' in FIG. 7A, and FIG. 8C is a cross-sectional view illustrating a portion of the shoe care device 1 taken along line C-C' in FIG. 7A.

The suction duct 210 can be configured to extend downwards from the outlet 42.

The suction duct 210 can be configured to include an upper duct 211, a middle duct 212, and a lower duct 213.

The upper duct 211 can configure the uppermost portion of the suction duct 210. The upper duct 211 can be configured to extend downwards from the outlet 42 in the vertical direction.

The middle duct 212 configures a portion further extending downwards from the lower end of the upper duct 211.

The middle duct 212 can be configured to be bent to either side from the upper duct 211. The middle duct 212 can be configured to be bent to the inside of the shoe care device 1 from the upper duct 211.

The lower duct 213 configures a portion further extending downwards from the lower end of the middle duct 212. The lower duct 213 can be configured to extend downwards from the middle duct 212 in the vertical direction.

In some implementations, the blower 220 can be configured to generate airflow in the connection path F10. In some examples, the blower 220 can be positioned between the suction duct 210 and the blowing duct 230 based on the air movement direction in the connection path F10, and can be configured to connect the suction duct 210 with the blowing duct 230. In some examples, In some examples, the blower 220 can be configured to connect the lower duct 213 with the blowing duct 230. In some examples, the blower 220 can be positioned lower than the outlet 42 and the inlet 43. In some implementations, the blower 220 can include a blowing fan 221, a blowing housing 225, and a motor 227.

The blowing fan 221 can be configured to rotate about the rotation axis 222 in the second direction Y, which is a horizontal direction and is perpendicular to the first direction X. The motor 227 of the blower 220 rotates the blowing fan 221.

The rotation axis 222 of the blowing fan 221 can be positioned in front of the blowing duct 230 in the first direction X.

The blowing housing 225 is configured to accommodate the blowing fan 221. The blowing housing 225 can be formed in a round shape about the rotation axis 222 of the blowing fan 221.

The blowing housing 225 is configured to communicate with the suction duct 210 and the blowing duct 230, respectively, and configures a portion of the connection path F10.

The blowing housing 225 can be connected to and communicate with the suction duct 210 on the rotation axis 222 of the blowing fan 221, and can be connected to and communicate with the blowing duct 230 at the edge thereof.

Accordingly, the air inside the suction duct 210 is introduced into the blowing housing 225 near the rotation axis 222 of the blowing fan 221, and the air inside the blowing housing 225 moves along the circumferential direction of the blowing housing 225 while being pressed towards the edge of the blowing housing 225 according to the rotation of the blowing fan 221, thereby moving to the blowing duct 230.

The blowing duct 230 can be formed such that the width in the second direction Y is continuously increased toward the upper portion.

The blowing duct 230 can be configured to include a lower blowing duct 231 and an upper blowing duct 232.

The lower blowing duct 231 is connected to the blower 220. The lower blowing duct 231 communicates with the blowing housing 225 of the blower 220.

The upper blowing duct 232 extends upwards from the lower blowing duct 231. The upper blowing duct 232 can be connected to the housing inlet 311 to communicate therewith.

The width W2 of the upper blowing duct 232 in the second direction Y can be configured to be greater than the width W1 of the lower blowing duct 231 in the second direction Y. The width W2 of the upper blowing duct 232 in the second direction Y can be configured to be 1.5 to 2.5 times the width W1 of the lower blowing duct 231 in the second direction Y.

With the configuration of the blowing duct 230 described above, the flow rate of air supplied to the inner space (the first path F11) of the dehumidifying block 400 can be stably secured, and, in particular, even if a pair of dehumidifying blocks 400 is provided, sufficient air can be supplied to the dehumidifying block 400.

The blowing housing 225 and the blowing duct 230 can form a spiral passage about the rotation axis 222 of the blowing fan 221 together such that the air inside the blowing housing 225 can naturally move to the blowing duct 230 when the blowing fan 221 rotates.

The spiral passage can be configured such that the radial distance from the rotation axis 222 of the blowing fan 221 gradually increases from blowing housing 225 to the blowing duct 230 along the rotational direction of the blowing fan 221. In some implementations, as shown in FIG. 8C, the distance from the rotation axis 222 of the blowing fan 221 to the outer edges of the blowing housing 225 and the blowing duct 230 can be configured to gradually increase along the clockwise direction.

Based on the first direction X, the rear end of the blowing housing 225 or the rear end of the blowing duct 230 can be configured to further protrude backwards in the first direction X compared to the rear end of the dehumidifying block 400, or to be position at the same position as the same.

Accordingly, the flow direction of the air passing through the blowing housing 225 and the blowing fan 221 can substantially match the flow direction of the air moving to the path (the first path F11) inside the dehumidifying block 400, or can naturally switch to the same. As shown in FIG. 8C, the air inside the blowing housing 225 and the blowing duct 230 moves in the clockwise direction about the rotation axis 222 of the blowing fan 221, and the air of the path (the first path F11) inside the dehumidifying block 400 also moves in the clockwise direction.

Accordingly, the air moving along the connection path F10 can smoothly pass through the dehumidifying block 400, and the path resistance of the air passing through the dehumidifying block 400 can be prevented from increasing.

Figure 9:
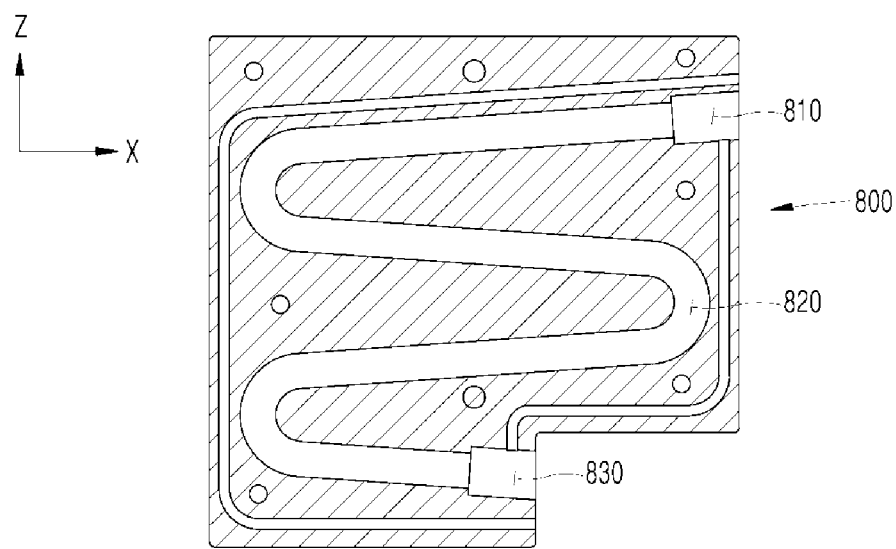
FIG. 9 is a view illustrating an example of an internal path structure of the condenser shown in FIG. 4A.

FIG. 9 is a view illustrating an internal path structure of the condenser 800 shown in FIG. 4A.

Figure 10A:
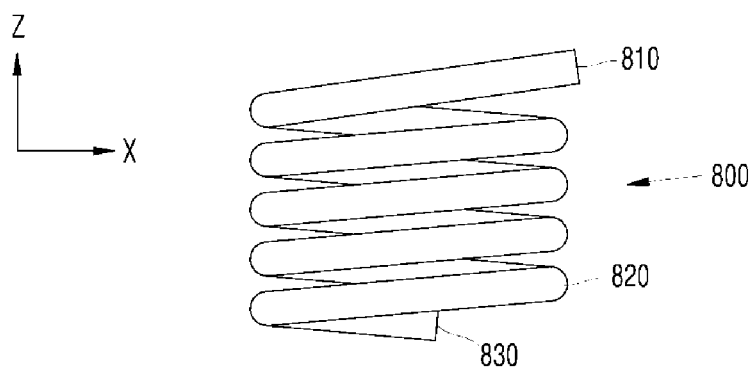
FIG. 10A is a side view illustrating an example of a condenser.
Figure 10B:
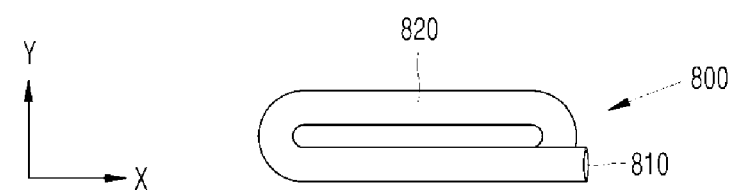
FIG. 10B is a plan view illustrating the condenser in FIG. 10A.

FIG. 10A is a side view illustrating an example of a condenser 800, and FIG. 10B is a plan view illustrating the condenser 800 in FIG. 10A.

The condenser 800 configures a portion of regeneration path F20.

The condenser 800 can be positioned behind the water supply tank 60 or the drain tank 70 inside the machine room 50.

The condenser 800 is positioned lower than the dehumidifying material 430 and higher than the sump 214. The condenser 800 is made of metal. The condenser 800 can be made of a metal with excellent thermal conductivity. The condenser 800 can be made of aluminum.

The condenser 800 can be configured to include a condenser inlet 810, a condenser outlet 830, and a condenser path 820.

The condenser inlet 810 is connected to the connection path F10. The condenser inlet 810 is connected to the regeneration path hole 527 by a separate pipe, hose, and the like constituting the regeneration path F20.

The condenser outlet 830 is connected to the sump 214. The condenser outlet 830 is connected to the sump hole 215 by a separate pipe, hose, and the like constituting the regeneration path F20.

The condenser path 820, which is a passage for air (or water) provided inside the condenser 800, connects the condenser inlet 810 with the condenser outlet 830.

The condenser path 820 can be configured such that the height thereof is gradually reduced from the condenser inlet 810 to the condenser outlet 830.

The condenser path 820 can be formed in a zigzag form. The condenser path 820 can be arranged parallel to the plane in the vertical direction.

Accordingly, the condenser 800 can be configured in a vertically thin structure, and the volume thereof occupying the inside of the machine room 50 can be minimized, and the water condensed inside the condenser 800 can move smoothly along the direction of gravity without gathering inside the condenser 800.

The condenser 800 can be positioned lower than the third section F10c and the damper 510.

The condenser 800 can be positioned on the opposite side of the heater 710 based on the suction duct 210. The suction duct 210 can be configured to shield the heater 710 and the condenser 800 from each other.

Accordingly, the heat of the heater 710 can be prevented from being transferred to the condenser 800, and condensation of water vapor can be effectively performed in the condenser 800.

Based on the lower duct 213, the condenser 800 can be positioned on the opposite side of the blower 220. Accordingly, the spaces on both sides of the lower duct 213 can be efficiently utilized, and the increase in the volume of the machine room 50 according to the provision of the condenser 800 can be prevented.

Figure 11A:
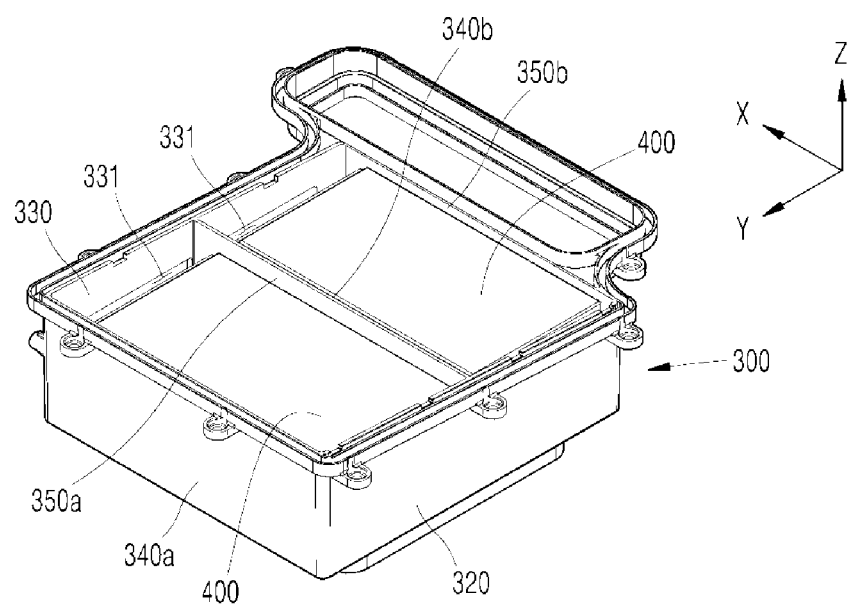
FIG. 11A is a perspective view illustrating an example state in which a dehumidifying housing, a dehumidifying block, and a heater are combined with each other in the shoe care device shown in FIG. 3B.
Figure 11B:
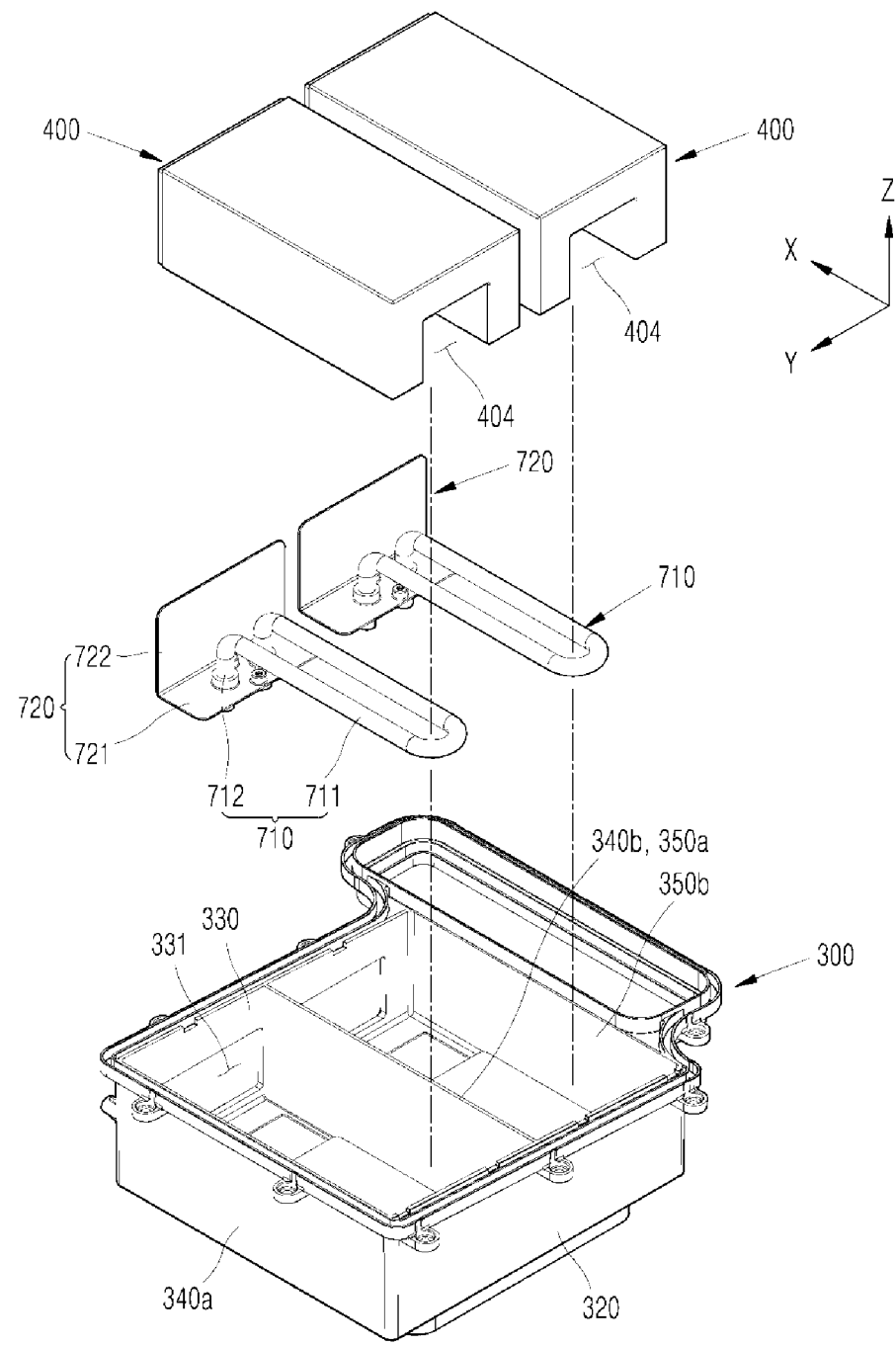
FIG. 11B is a perspective view illustrating an example state in which the dehumidifying housing, the dehumidifying block, and the heater are separated from each other in FIG. 11A.

FIG. 11A is a perspective view illustrating the state in which a dehumidifying housing 300, a dehumidifying block 400, and a heater 710 are combined with each other in the shoe care device 1 shown in FIG. 3B. FIG. 11B is a perspective view illustrating the state in which the dehumidifying housing 300, the dehumidifying block 400, and the heater 710 are separated from each other in FIG. 11A.

Figure 12:
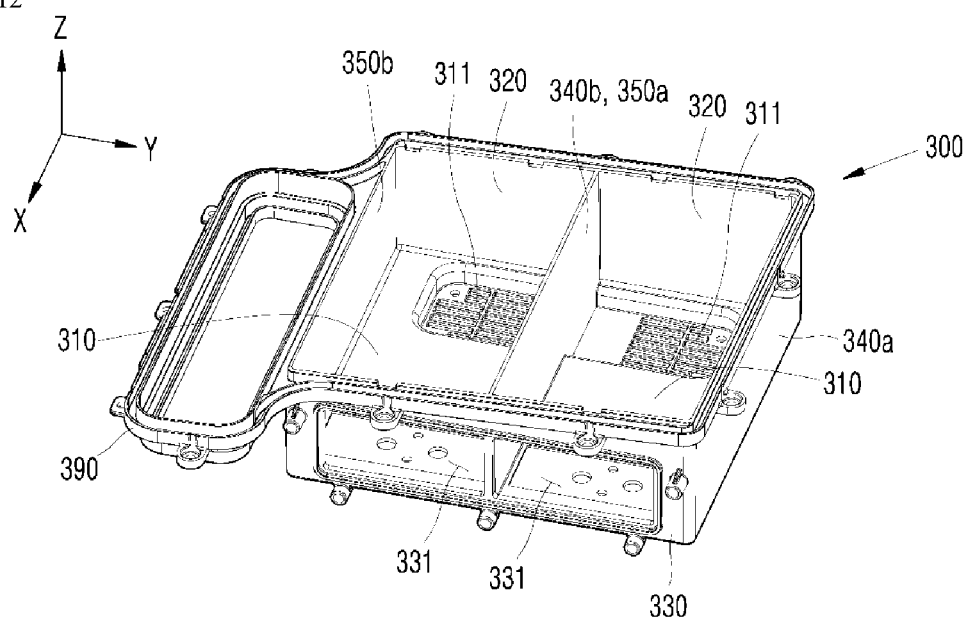
FIG. 12 is a perspective view illustrating the dehumidifying housing in FIG. 11A.

FIG. 12 is a perspective view illustrating the dehumidifying housing 300 in FIG. 11A.

The dehumidifying housing 300 can be configured as a container capable of accommodating the dehumidifying block 400.

The dehumidifying housing 300 can be configured as a container of which the upper side is substantially open. In particular, the dehumidifying housing 300 can be configured such that the dehumidifying block 400 can be put into or taken out of the dehumidifying housing 300 through the upper side thereof. The dehumidifying material cover 46 can be coupled to the upper side of the dehumidifying housing 300 to open and close the upper opening of the dehumidifying housing 300.

The dehumidifying block 400 is accommodated inside the dehumidifying housing 300.

The inner space of the dehumidifying housing 300 configures a portion of the connection path F10.

The heater 710 is positioned on the connection path F10 and configured to heat the air in the connection path F10.

In addition, the heater 710 is configured to heat the dehumidifying block 400. The heater 710 is configured to heat the dehumidifying material 430 constituting the dehumidifying block 400. In some examples, the heater 710 is disposed on the connection path F10 to be adjacent to the dehumidifying block 400.

Both the dehumidifying block 400 and the heater 710 can be accommodated in the dehumidifying housing 300.

The heater 710 can be positioned in the inner space formed by the dehumidifying housing 300 and the dehumidifying block 400.

The dehumidifying housing 300 and the heater 710 will be further described later.

Figure 13A:
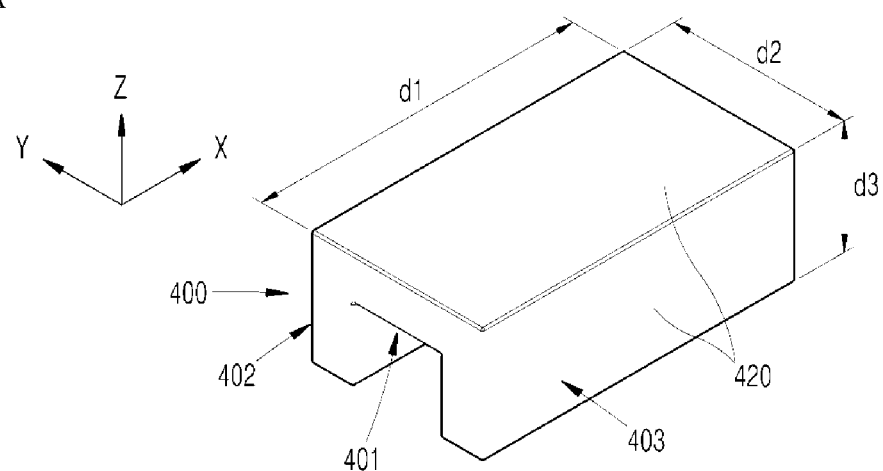
FIGS. 13A and 13B are perspective views illustrating an example of a dehumidifying block when viewed in different directions.
Figure 13B:
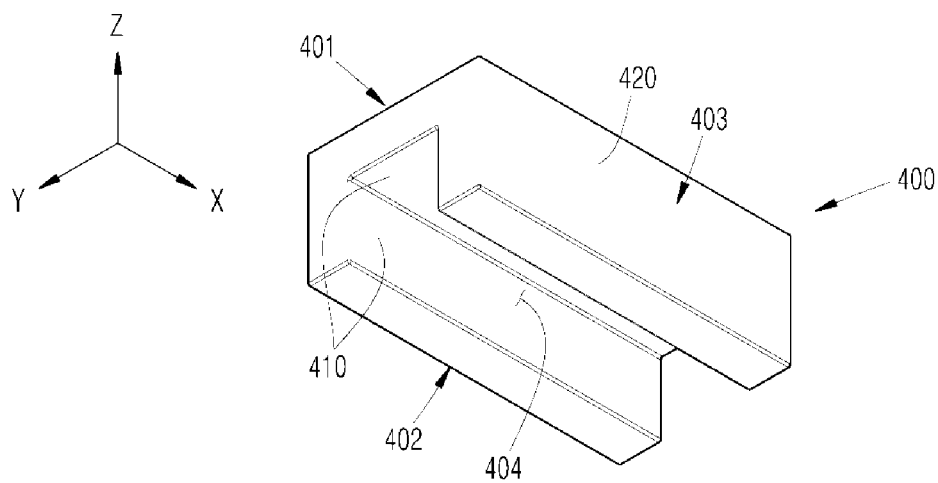

FIGS. 13A and 13B are perspective views illustrating a dehumidifying block 400 when viewed in different directions.

Figure 13C:
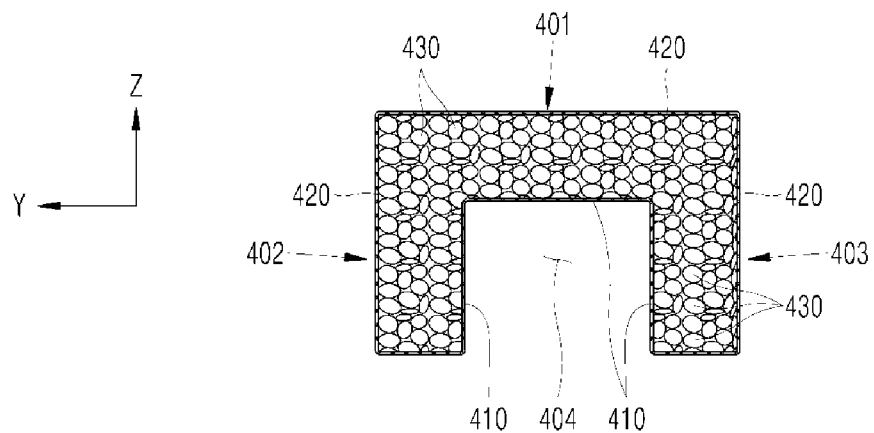
FIG. 13C is a transverse cross-sectional view illustrating the dehumidifying block in FIG. 13A.

FIG. 13C is a transverse cross-sectional view illustrating the dehumidifying block 400 in FIG. 13A.

Figure 14:
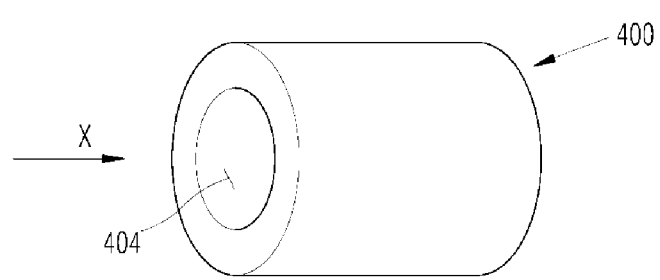
FIG. 14 is a perspective view illustrating an example of a dehumidifying block.

FIG. 14 is a perspective view illustrating a dehumidifying block 400.

Figure 15A:
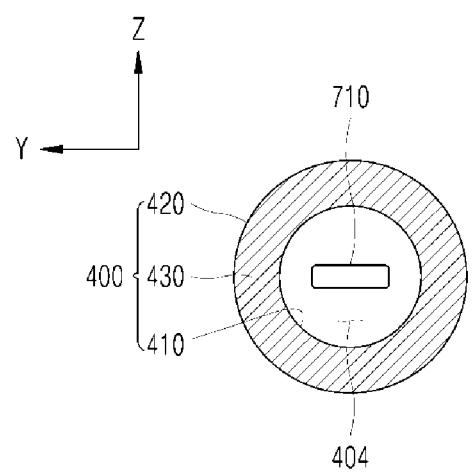
FIGS. 15A and 15B are transverse cross-sectional views illustrating examples of a dehumidifying block and a heater, respectively.
Figure 15B:
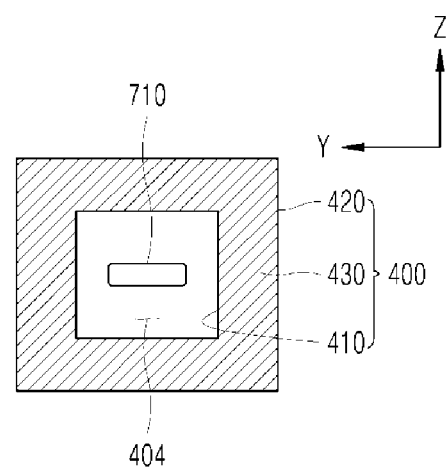

FIGS. 15A and 15B are transverse cross-sectional views illustrating a dehumidifying block 400 and a heater 710, respectively.

Figure 16A:
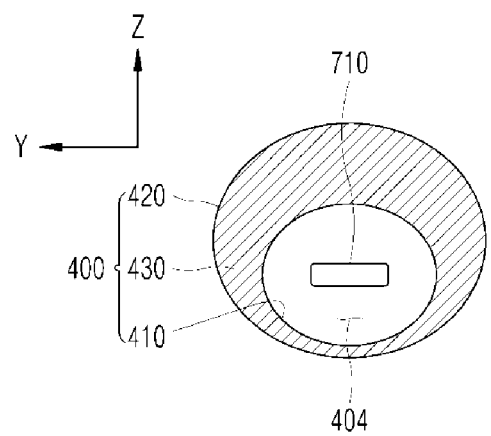
FIGS. 16A and 16B are transverse cross-sectional views illustrating examples of a dehumidifying block and a heater, respectively.
Figure 16B:
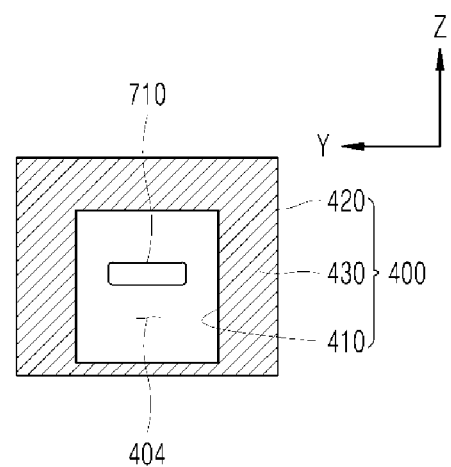

FIGS. 16A and 16B are transverse cross-sectional views illustrating a dehumidifying block 400 and a heater 710, respectively.

Figure 17A:
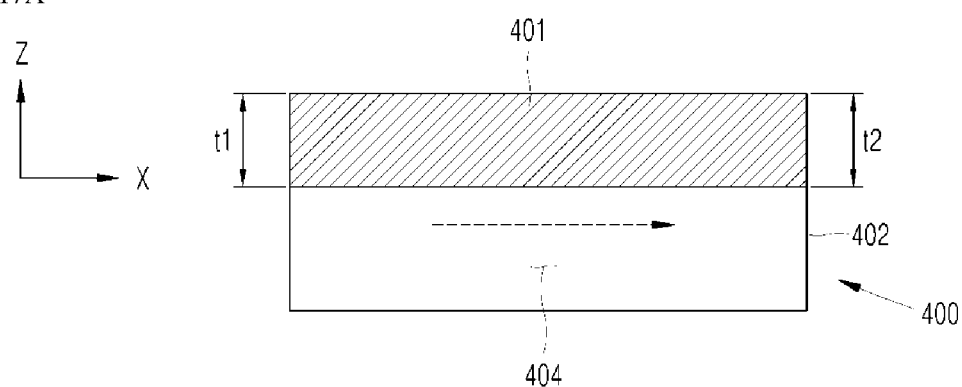
FIGS. 17A and 17B are longitudinal cross-sectional views illustrating examples of a dehumidifying blocks.
Figure 17B:
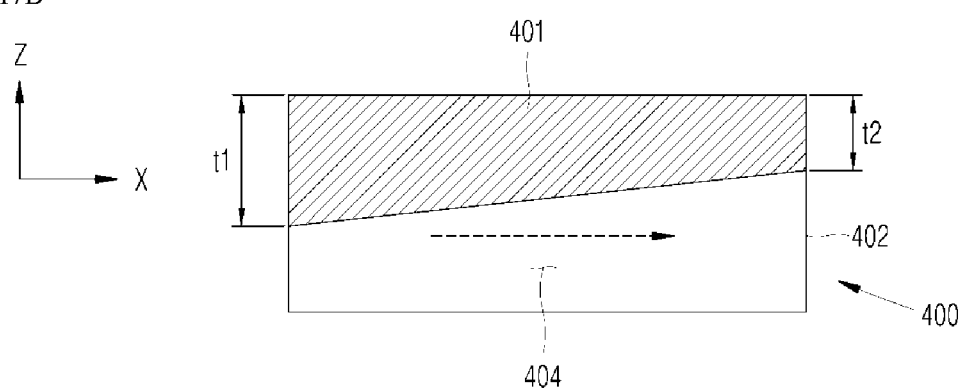

FIGS. 17A and 17B are longitudinal cross-sectional views illustrating a dehumidifying block 400.

A plurality of dehumidifying blocks 400 can be provided in the shoe care device 1.

A pair of dehumidifying blocks 400 can be provided in the shoe care device 1. The dehumidifying block 400 can be arranged in the second direction Y perpendicular to the first direction X.

The dehumidifying block 400 is positioned on the connection path F10, and is configured to remove moisture from the air passing through the connection path F10.

The dehumidifying block 400 is configured to form the inner space 404, and the air in the inner space 404 moves to pass through the dehumidifying block 400 over the entire area thereof. Accordingly, the contact area between the air passing through the connection path F10 and the dehumidifying material 430 can be increased.

The dehumidifying block 400 can be configured to include an inner mesh 410, an outer mesh 420, and a dehumidifying material 430. In addition, the dehumidifying block 400 can be configured to include a first frame 440.

Each of the inner mesh 410 and the outer mesh 420 can be configured in the form of a mesh, and a plurality of holes can be formed in the inner mesh 410 and the outer mesh 420 over the entire area thereof. The holes of the inner mesh 410 and the outer mesh 420 can be formed smaller than the size of each grain of the dehumidifying material 430 to prevent the dehumidifying material 430 from escaping therefrom.

The inner mesh 410 and the outer mesh 420 can be made of a relatively hard material to maintain the shape of the dehumidifying block 400. Each of the inner mesh 410 and the outer mesh 420 can be configured to include a material such as a metal, a heat-resistant synthetic resin or synthetic fiber, a carbon fiber, and the like.

Each of the inner mesh 410 and the outer mesh 420 can have a predetermined area, and can be formed in a curved shape, or they can be configured in the form of a combination of flat surfaces bent to each other.

The inner mesh 410 can have a structure to form the inner space 404 of the dehumidifying block 400. The heater 710 can be accommodated in the inner space 404 of the inner mesh 410.

The outer mesh 420 is positioned outside the inner mesh 410.

The inner mesh 410 configures the inner surface of the dehumidifying block 400, and the outer mesh 420 configures the outer surface of the dehumidifying block 400.

Each of the inner mesh 410 and the outer mesh 420 can have a constant section along the first direction X.

As described above, the dehumidifying material 430 is configured as a combination of a plurality of grains (or stones), and the space between the inner mesh 410 and the outer mesh 420 is filled with the dehumidifying material 430.

The dehumidifying block 400 can be configured in the form of a pipe or a tunnel extending along the horizontal direction.

The dehumidifying block 400 can have various shapes in the cross-section thereof, such as a circle, an ellipse, a polygon, and the like.

The dehumidifying block 400 can have a shape that is opened to one side in the cross-section thereof. The opening in the dehumidifying block 400 can be directed downwards.

The dehumidifying block 400 can have a cross-section in a "⊏" shape or a "U" shape.

The dehumidifying block 400 can have a cross-section in a "⌐⌐" shape (see FIG. 13C). The dehumidifying block 400 in the above structure expands the contact area between the dehumidifying material 430 and the air, enables uniform formation of the second path F12 over the entire outer area of the dehumidifying block 400, and facilitates separation and replacement of the dehumidifying block 400.

In the case where the dehumidifying block 400 has a cross-section in a "⌐⌐" shape, the inner mesh 410 and the outer mesh 420 can be connected to each other.

In the case where the dehumidifying block 400 has a cross-section in a "⌐⌐" shape, the dehumidifying block 400 can be divided into a ceiling part 401, a first side wall 402, and a second side wall 403, which will be described in detail later.

The inner space 404 of the dehumidifying block 400 (the inner space of the inner mesh 410) configures the first path F11 that is a portion of the connection path F10. The heater 710 can be positioned in the first path F11.

As described above, the dehumidifying block 400 has a predetermined length in the first direction X, and the length of the first path F11 is the same as or similar to the total length d1 of the dehumidifying block 400 in the first direction X.

The first path F11 is configured to have a predetermined length in the first direction X. In some implementations, the length of the first path F11 in the first direction X is configured to be greater than the length (width) in the second direction Y or the length (height) in the third direction Z. That is, the longitudinal direction of the first path F11 can be parallel to the first direction X. In some implementations, the length of the first path F11 in the first direction X can be configured to be double the length (width) in the second direction Y or the length (height) in the third direction Z.

If the first direction X is the longitudinal direction of the first path F11, if the second direction Y is the width direction of the first path F11, and if the third direction Z is the height direction of the first path F11, the length of the first path F11 can be greater than the width and the height of the first path F11.

The air introduced into the outlet 42 can flow while passing through the dehumidifying block 400 from the inside to the outside thereof.

The first path F11 configures the upstream of the second section F10b of the connection path F10. That is, when the air of the first section F10a flows to the second section F11b, the air first enters the first path F11, and then the air introduced into the first path F11 can pass through the dehumidifying block 400.

The first path F11 can be formed inside the dehumidifying block 400, and as described above, the first path F11 can be formed long in the first direction X so that the air moving along the first path F11 can move in the direction to pass through the dehumidifying block 400 (the direction crossing the first direction X), so the contact area between the air of the connection path F10 and the grains of each dehumidifying material 430 can become sufficiently large, thereby increasing the dehumidifying efficiency.

If the distance between the inner mesh 410 and the outer mesh 420 in the dehumidifying block 400 is the thickness of the dehumidifying block 400, the thickness of the upper portion of the dehumidifying block 400 can be greater than the thickness of the lower portion (see FIG. 16A and FIG. 16B).

The air passing through the first path F11 can tend to flow upwards while being heated by the heater 710, and since the thickness of the upper portion of the dehumidifying block 400 is greater than the thickness of the lower portion, the air passing through the dehumidifying block 400 can come into contact with a large number of dehumidifying material grains, thereby further improving the dehumidifying efficiency.

In some implementations, the dehumidifying block 400 can have a constant thickness (t1=t2) along the first direction X (see FIG. 17A).

In an example, the dehumidifying block 400 can have a thickness that changes along the first direction X. For example, the rear portion of the dehumidifying block 400 can be thicker in the first direction X, and the dehumidifying block 400 can become thinner toward the front portion thereof in the first direction X (t1>t2) (see FIG. 17B)

In particular, the rear portion of the ceiling part 401 of the dehumidifying block 400 can be thicker in the first direction X, and the ceiling part 401 of the dehumidifying block 400 can become thinner toward the front portion thereof in the first direction X (t1>t2). In addition, the ceiling part 401 of the dehumidifying block 400 can be configured such that the inner surface thereof is inclined upwards as it is closer to the front portion thereof in the first direction X.

As will be described later, the housing inlet 311 can face the bottom surface of the ceiling part 401 of the dehumidifying block 400, and the housing inlet 311 can be formed at the position close to the rear portion in the first direction X.

In this case, the air injected into the first path F11 through the housing inlet 311 can be directed toward the ceiling part 401 at the rear in the first direction X, and the air introduced into the first path F11 can first come into contact with the dehumidifying material in the thickest portion thereof, thereby improving the contact efficiency between the air and the dehumidifying material.

In addition, since the inner surface (bottom surface) of the ceiling part 401 of the dehumidifying block 400 is formed to be inclined upwards as it is closer to the front portion thereof in the first direction X (see FIG. 17B), the air passing through the blowing housing 225, the blowing duct 230, and the first path F11 can effectively move and a flow resistance can be minimized.

Figure 18:
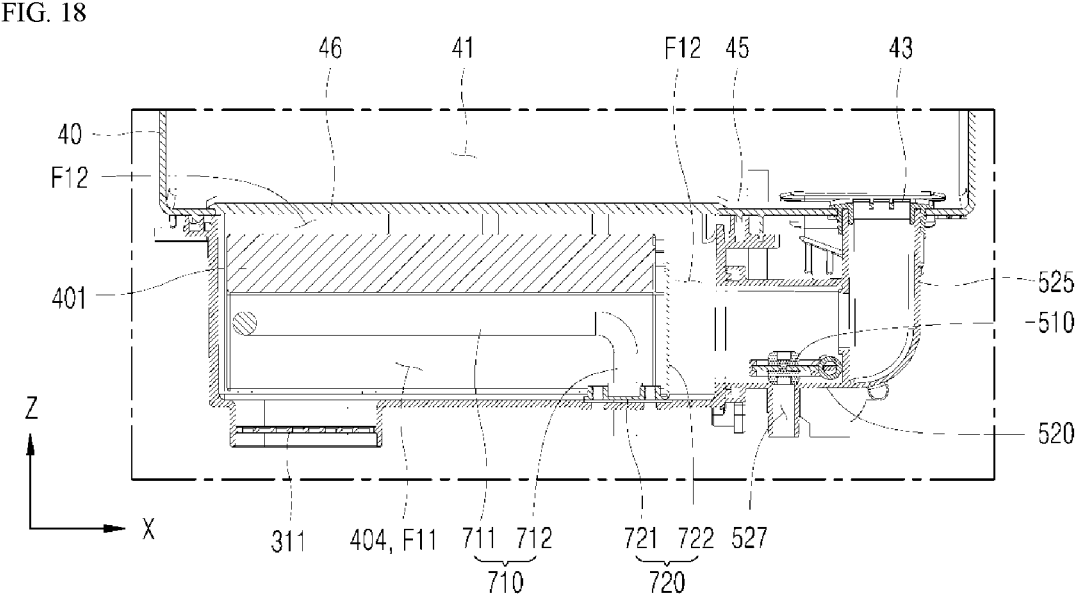
FIGS. 18 and 19A are cross-sectional views illustrating a partial configuration of the shoe care device shown in FIG. 3A, respectively.
Figure 19A:
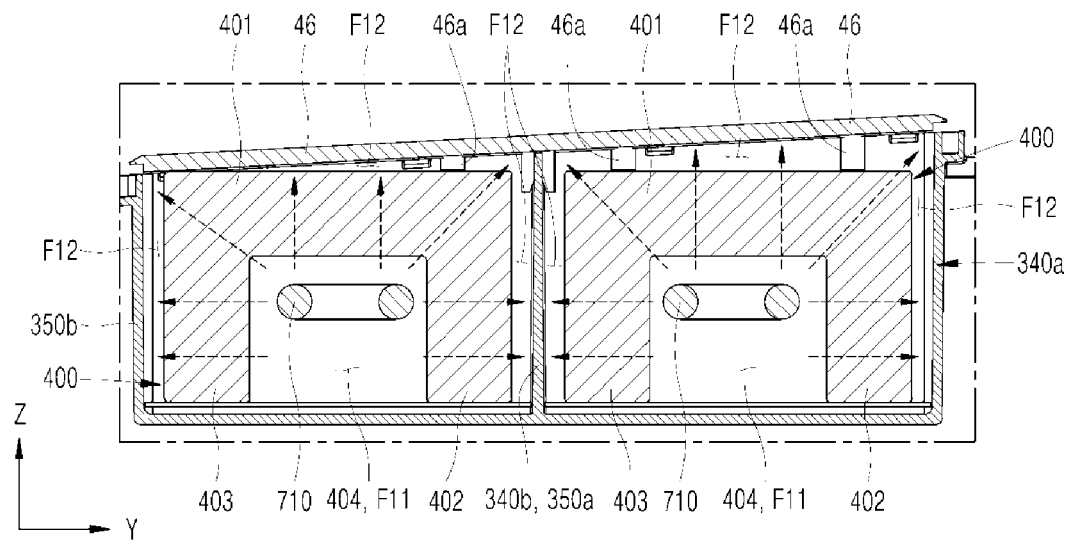

FIGS. 18 and 19A are cross-sectional views illustrating a partial configuration of the shoe care device 1 shown in FIG. 3A, respectively.

Figure 19B:
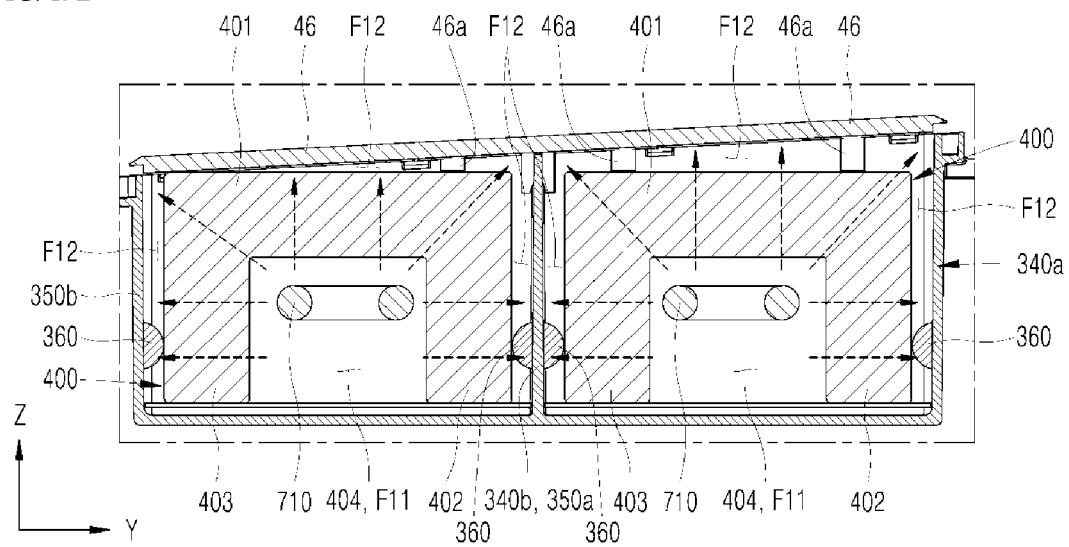
FIGS. 19B and 19C are cross-sectional views illustrating a partial configuration of the shoe care device, respectively.
Figure 19C:
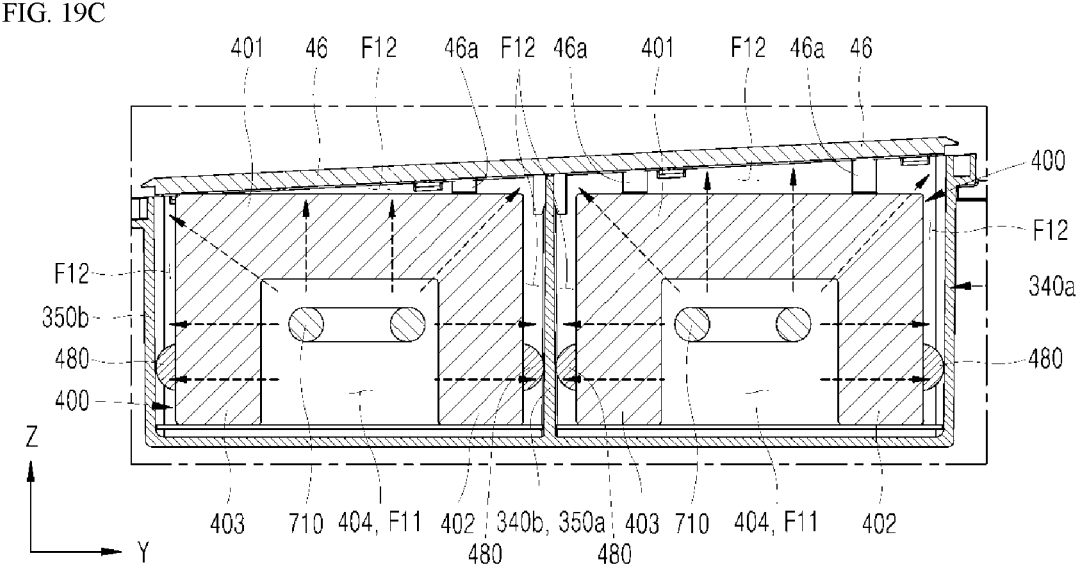

FIGS. 19B and 19C are cross-sectional views illustrating a partial configuration of a shoe care device 1, respectively.

The dehumidifying block 400 and the dehumidifying material 430 can be positioned below the bottom (the bottom plate 45 and the dehumidifying material cover 46) of the inner cabinet 40, and the dehumidifying block 400 can be spaced apart from the bottom of the inner cabinet 40.

The external space of the dehumidifying block 400 (the external space of the outer mesh 420) configures the second path F12 that is a portion of the connection path F10.

The space between the outer surface of the dehumidifying block 400 (the outer surface of the outer mesh 420) and the inner surface of the dehumidifying housing 300 can configure a portion of the second path F12.

The space between the cabinet bottom plate 45 of the inner cabinet 40 and the dehumidifying block 400 can configure a portion of the second path F12. In particular, the space between the dehumidifying material cover 46 and the dehumidifying block 400 can configure a portion of the second path F12.

The air introduced into the outlet 42 passes through the suction duct 210, the blower 220, and the blowing duct 230 to flow into the inner space 404 of the inner mesh 410, and flows from the first path F11 to the second path F12 while passing through the dehumidifying block 400.

The dehumidifying block 400 can be configured to include a ceiling part 401, a first side wall 402, and a second side wall 403. The inner mesh 410 and the outer mesh 420 can be connected to each other.

The ceiling part 401 can be formed to be flat in the horizontal direction.

Each of the first side wall 402 and the second side wall 403 can be flat in the vertical direction. The first side wall 402 extends downwards from one side of the ceiling part 401, and the second side wall 403 extends downwards from the opposite side of the ceiling part 401. The second side wall 403 can be spaced apart from the first side wall 402, and can be configured to be parallel to the first side wall 402.

The ceiling part 401, the first side wall 402, and the second side wall 403 are configured to have predetermined thicknesses, respectively.

The ceiling part 401, the first side wall 402, and the second side wall 403 is configured to include an inner mesh 410, an outer mesh 420, and a dehumidifying material 430, respectively.

The ceiling part 401, the first side wall 402, and the second side wall 403 are configured to respectively include an inner mesh 410, an outer mesh 420, a dehumidifying material 430, and a first frame 440.

In some implementations, assuming that the shortest distance from the inner mesh 410 to the outer mesh 420 in the dehumidifying block 400 is the thickness of the dehumidifying block 400, the ceiling part 401, the first side wall 402, and the second side wall 403 can be configured to have the same thickness as each other.

In an example, assuming that the shortest distance from the inner mesh 410 to the outer mesh 420 in the dehumidifying block 400 is the thickness of the dehumidifying block 400, the thickness of the ceiling part 401 can be configured to be greater than the thickness of the first side wall 402 or second side wall 403.

The inner space 404 surrounded by the ceiling part 401, the first side wall 402, and the second side wall 403 configure a first path F11, and the outer space of the ceiling part 401, the first side wall 402, and the second side wall 403 configure a second path F12.

The heater 710 can be configured to be surrounded by the ceiling part 401, the first side wall 402, and the second side wall 403.

In the shoe care device 1, the first path F11, which is the inner space 404 of the dehumidifying block 400, can be configured to be shielded or sealed in the rear and front thereof in the first direction X. The first path F11, which is the inner space of the dehumidifying block 400, can be shielded or sealed in the foremost and rearmost thereof in the first direction X.

Therefore, all or most air introduced into the first path F11 can pass through the dehumidifying block 400, instead of escaping from the first path F11 through the rear or front in the first direction X.

The dehumidifying housing 300 can be configured to include a housing bottom plate 310, a rear dehumidifying material wall 320, a front dehumidifying material wall 330, left dehumidifying material walls 340a and 340b, and right dehumidifying material walls 350a and 350b (see FIGS. 11B and 12).

The housing bottom plate 310 can be configured in the form of a plate on which the dehumidifying block 400 is placed. The housing bottom plate 310 can be configured in the form of a plate that is flat in the horizontal direction.

A housing inlet 311 is formed on the housing bottom plate 310.

The housing inlet 311 is a hole formed on the housing bottom plate 310 and configures an inlet through which air is introduced into the inner space of the dehumidifying block 400. The housing inlet 311 configures an inlet through which air flows into the first path F11.

In the housing inlet 311, a mesh such as a grid type, a screen, or the like can be provided.

The housing inlet 311 can be formed to face the bottom surface of the ceiling part 401 of the dehumidifying block 400.

The housing inlet 311 can be formed to be closer to the rear of the dehumidifying housing 300 in the first direction X. The housing inlet 311 can be formed adjacent to the rear end of the housing bottom plate 310 in the first direction X.

The ceiling part 401 of the dehumidifying block 400 can be configured such that a portion thereof closer to the housing inlet 311 is thicker than the portion far away from the housing inlet 311.

The rear dehumidifying material wall 320, the front dehumidifying material wall 330, the left dehumidifying material walls 340a and 340b, and the right dehumidifying material walls 350a and 350b can respectively constitute wall surfaces erected in the vertical direction. In the dehumidifying housing 300, based on the first direction X, the rear dehumidifying material wall 320 can configure a rear wall surface, the front dehumidifying material wall 330 can configure a front wall surface, the left dehumidifying material wall 340a and 340b can configure left wall surfaces, and the right dehumidifying material walls 350a and 350b can configure right wall surfaces.

The rear dehumidifying material wall 320 extends upwards from the housing bottom plate 310. In the state in which the dehumidifying block 400 is accommodated in the dehumidifying housing 300, the rear dehumidifying material wall 320 is positioned behind the dehumidifying block 400 in the first direction X. In this case, the rear dehumidifying material wall 320 can be configured to be in close contact with or close to the rear surface of the dehumidifying block 400 in the first direction X.

In the case where the rear dehumidifying material wall 320 is close to the rear surface of the dehumidifying block 400 in the first direction X, the gap between the rear dehumidifying material wall 320 and the dehumidifying block 400 can be configured to be very small, for example, about 1 mm or less.

The rear dehumidifying material wall 320 can be configured to shield or seal the first path F11, which is the inner space 404 of the dehumidifying block 400, at the rear thereof in the first direction X.

The front dehumidifying material wall 330 extends upwards from the housing bottom plate 310. The front dehumidifying material wall 330 is positioned in front of the dehumidifying block 400 in the first direction X. In the state in which the dehumidifying block 400 is accommodated in the dehumidifying housing 300, the front dehumidifying material wall 330 is spaced forward apart from the dehumidifying block 400 and the vertical plate 722 in the first direction X. A housing outlet 331 through which the air in the second path F12 flows can be formed in the front dehumidifying material wall 330 so as to penetrate the same in the first direction X.

The left dehumidifying material walls 340a and 340b connect the rear dehumidifying material wall 320 and the front dehumidifying material wall 330 on the left side of the dehumidifying block 400 in the first direction X.

The right dehumidifying material walls 350a and 350b connect the rear dehumidifying material wall 320 and the front dehumidifying material wall 330 on the right side of the dehumidifying block 400 in the first direction X.

In the case where a pair of dehumidifying blocks 400 is provided in the shoe care device 1, the dehumidifying housing 300 can be configured to accommodate the pair of dehumidifying blocks 400 in separate spaces.

In some examples, the dehumidifying housing 300 can be configured to include a housing bottom plate 310, a rear dehumidifying material wall 320, a front dehumidifying material wall 330, a first left dehumidifying material wall 340a, a first right dehumidifying material wall 350a, a second left dehumidifying material wall 340b, and a second right dehumidifying material wall 350b.

Any one of the dehumidifying blocks 400 can be accommodated between the first left dehumidifying material wall 340a and the first right dehumidifying material wall 350a, and the other dehumidifying block 400 can be accommodated between the second left dehumidifying material wall 340b and the second right dehumidifying material wall 350b.

In the shoe care device 1, the first right dehumidifying material wall 350a and the second left dehumidifying material wall 340b can be formed separately from each other, or can be formed integrally with each other.

In the state in which the dehumidifying blocks 400 are accommodated in the dehumidifying housing 300, the inner surfaces of the left dehumidifying material walls 340a and 340b can face the outer surfaces of the first side walls 402 while being spaced apart from each other. Accordingly, predetermined gaps are formed between the left dehumidifying material walls 340a and 340b and the first side walls 402, and these gaps configure portions of the second path F12.

In addition, in the state in which the dehumidifying blocks 400 are accommodated in the dehumidifying housing 300, the inner surfaces of the right dehumidifying material walls 350a and 350b can face the outer surfaces of the second side walls 403 while being spaced apart from each other. Accordingly, predetermined gaps are formed between the right dehumidifying material walls 350a and 350b and the second side walls 403, and these gaps configure portions of the second path F12.

In addition, as described above, gaps are formed between the dehumidifying material cover 46 and the dehumidifying blocks 400, and these gaps configure the second path F12.

The space configuring the second path F12 communicates with the space between the vertical plate 722 and the front dehumidifying material wall 330, and the air in the second path F12 moves forward in the first direction X through the housing outlet 331 to flow into the damper housing 520.

In the shoe care device 1, based on the third direction Z opposite the direction of gravity, the dehumidifying block 400 is located at the same height as or at a higher position than the housing inlet 311, which is the inlet of the first path F11, and the first path F11 is formed upwards from the lower end of the dehumidifying block 400, and the second path F12 is formed upwards from the lower end of the dehumidifying block 400 so as to surround the first path F11.

In the first path F11, the air moves in a direction perpendicular to the first direction X while moving along the first direction X.

The pressure in the first path F11 is greater than the pressure in the second path F12, and the pressure at the rear of the first path F11 in the first direction X, in which the housing inlet 311 is formed, is greater than the front thereof. In addition, the pressure inside the dehumidifying housing 300 is greater than the pressure inside the damper housing 520.

Therefore, considering the direction of movement of air and the applied direction of pressure in the connection path F10, when the air in the first path F11 passes through the dehumidifying block 400 to flow to the second path F12, the air can pass and flow through entire portion of the dehumidifying material 430, enabling maximum utilization of the dehumidifying material 430.

In addition, when the heater 710 is operated in regeneration of the dehumidifying material 430, the air in the first path F11 can move more smoothly in the direction opposite the direction of gravity (the third direction Z), thereby effectively regenerating the dehumidifying material 430.

In the shoe care device 1, the dehumidifying housing 300 can be configured to include a first guide protrusion 360. A plurality of first guide protrusions 360 is provided in the dehumidifying housing 300.

The first guide protrusions 360 can be configured to protrude inwards from the respective inner surfaces of the left dehumidifying material walls 340a and 340b and the respective inner surfaces of the right dehumidifying material walls 350a and 350b so as to support the dehumidifying blocks 400.

As the first guide protrusions 360 are formed, predetermined gaps are stably formed between the left dehumidifying material walls 340a and 340b and the first side walls 402, and predetermined gaps are stably formed between the right dehumidifying material walls 350a and 350b and the second side walls 403. Accordingly, the dehumidifying block 400 is prevented from moving in the horizontal direction inside the dehumidifying housing 300 and the second path F12 is stably maintained.

In the shoe care device 1, the dehumidifying block 400 can be configured to include a second guide protrusion 480. A plurality of second guide protrusions 480 is provided in the dehumidifying block 400.

The second guide protrusions 480 can be configured to protrude outwards from the outer surface of the dehumidifying block 400. The second guide protrusions 480 are configured to protrude outwards from the outer surface of the first side wall 402 and the outer surface of the second side wall 403, respectively. Some second guide protrusions 480 can be in close contact with the inner surfaces of the left dehumidifying material wall 340a and 340b, and other second guide protrusions 480 can be in close contact with the inner surfaces of the right dehumidifying material wall 350a and 350b.

As the second guide protrusions 480 are formed, predetermined gaps are stably formed between the left dehumidifying material walls 340a and 340b and the first side walls 402, and predetermined gaps are stably formed between the right dehumidifying material walls 350a and 350b and the second side walls 403. Accordingly, the dehumidifying block 400 is prevented from moving in the horizontal direction inside the dehumidifying housing 300 and the second path F12 is stably maintained.

In the shoe care device 1, the first guide protrusion 360 and the second guide protrusion 480 can be formed selectively, or can be formed together.

In the shoe care device 1, the dehumidifying material cover 46 can be configured to include a third guide protrusion 46a.

The third guide protrusion 46a can be configured to protrude downwards from the bottom surface of the dehumidifying material cover 46 to support the dehumidifying block 400. A plurality of third guide protrusions 46a can be provided in the dehumidifying material cover 46.

As the third guide protrusions 46a are formed, a predetermined gap is stably formed between the dehumidifying material cover 46 and the ceiling part 401. Accordingly, the dehumidifying block 400 is prevented from moving in the vertical direction inside the dehumidifying housing 300, and the second path F12 is stably maintained.

In some implementations, if the configurations for stably maintaining the second path F12 (the first guide protrusions 360, the second guide protrusions 480, or the third guide protrusions 46a) are not provided, the dehumidifying block 400 can move inside the dehumidifying housing 300, and in some examples, the second path F12 is not stably maintained so that the volume of any portion of the second path F12 can become larger or smaller. In this case, the pressure, speed, etc. of the air flowing through the second path F12 can fall outside of the expected range, and efficiency of dehumidifying air by the dehumidifying block 400 and/or regenerating the dehumidifying material can be reduced.

Figure 20:
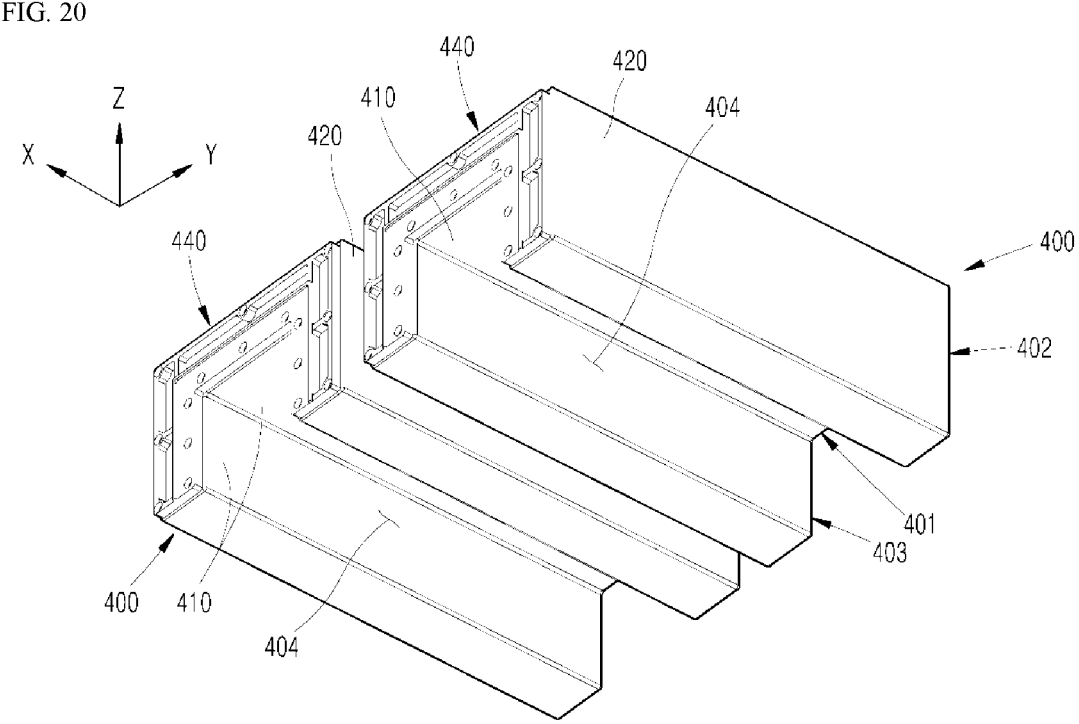
FIG. 20 is a perspective view illustrating an example of a pair of dehumidifying blocks shown in FIG. 11B.

FIG. 20 is a perspective view illustrating a pair of dehumidifying blocks 400 shown in FIG. 11B.

Figure 21A:
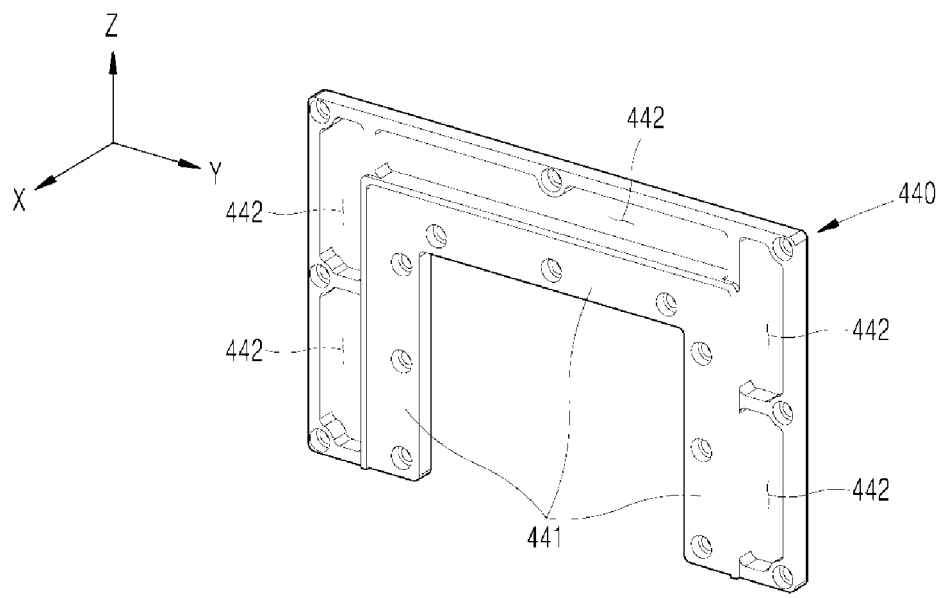
FIG. 21A is a perspective view illustrating an example of a first frame separated from the dehumidifying block in FIG. 20.
Figure 21B:
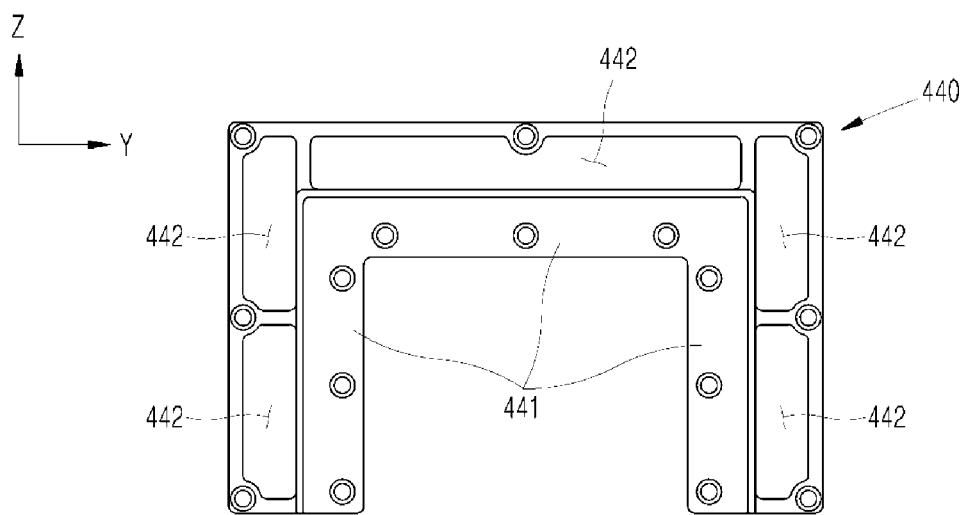
FIG. 21B is a front view illustrating the first frame in FIG. 21A.

FIG. 21A is a perspective view illustrating a first frame 440 separated from the dehumidifying block 400 in FIG. 20, and FIG. 21B is a front view illustrating the first frame 440 in FIG. 21A.

Figure 22A:
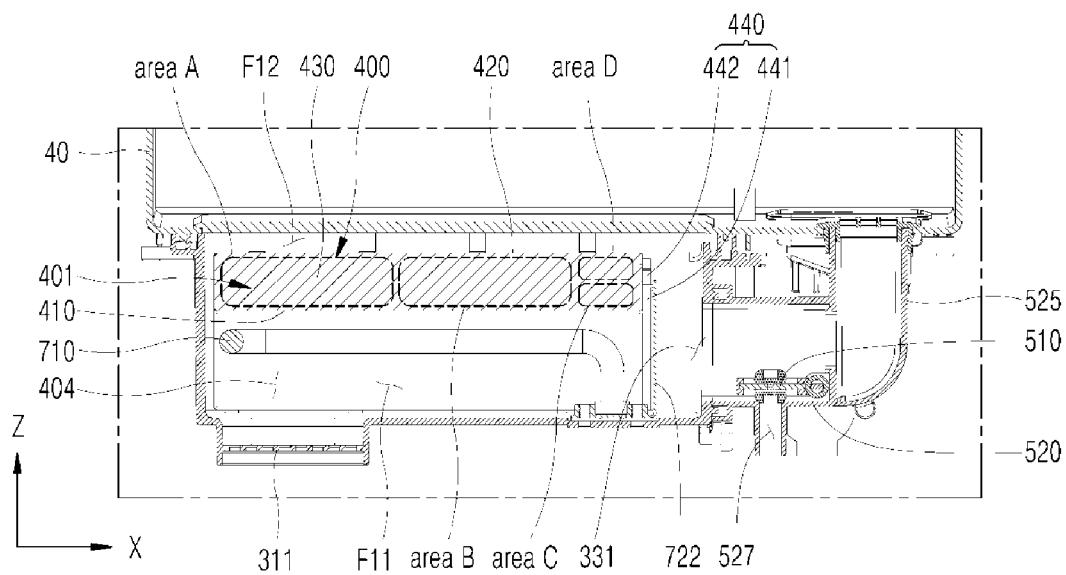
FIG. 22A is a cross-sectional view of the shoe care device and illustrates the flow of air around an example of a first frame.

FIG. 22A is a cross-sectional view of a shoe care device 1, which illustrates the flow of air around the first frame 440.

Figure 22B:
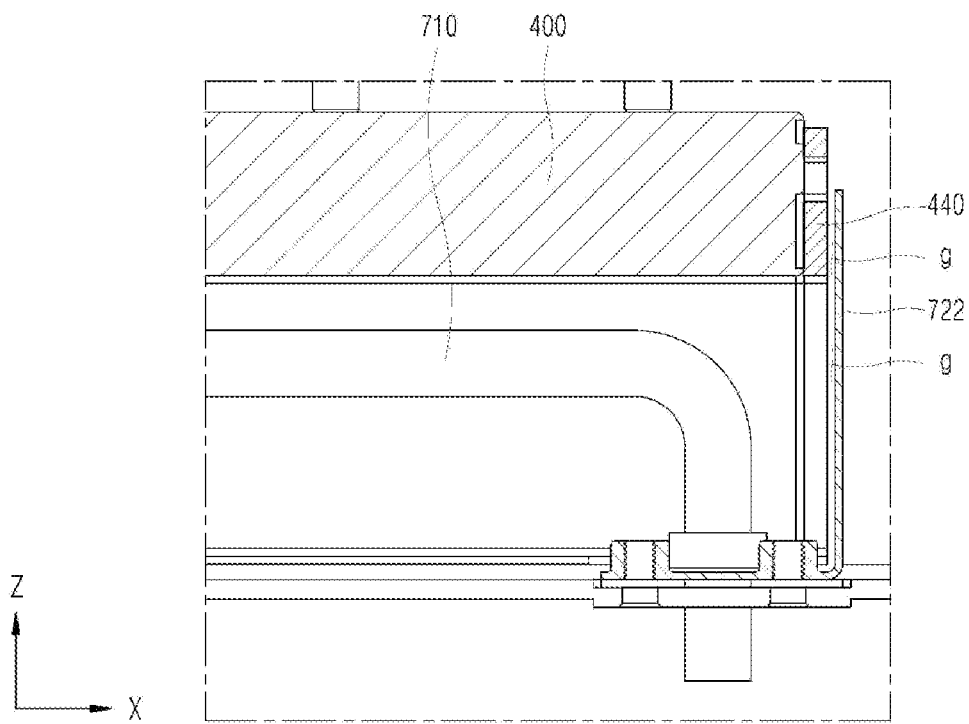
FIG. 22B is a cross-sectional view illustrating a portion of an example of a shoe care device.

FIG. 22B is a cross-sectional view of a portion of a shoe care device 1

The first frame 440 can configure a front surface of the dehumidifying block 400 in the first direction X. The first frame 440 can be configured in the form of a relatively hard plate, and can include a material such as metal, synthetic resin, ceramic, carbon fiber, or the like.

The first frame 440 can configure front surfaces of the ceiling part 401, the first side wall 402, and the second side wall 403 in the first direction X.

The first frame 440 is coupled along the edges of an inner mesh 410 and an outer mesh 420. The inner mesh 410 and the outer mesh 420 can be fixed to the first frame 440.

The inner mesh 410 and the outer mesh 420 are fixed to the first frame 440 so that the overall structure of the dehumidifying block 400 can be stably maintained, and the state in which the dehumidifying block 400 is filled with the dehumidifying material 430 can be stably maintained.

The first frame 440 can form a surface perpendicular to or inclined to the first direction X. The first frame 440 can form a surface parallel to the second direction Y and the third direction Z.

The first frame 440 can be configured to include a block member 441 and an opening 442.

The block member 441 is a portion that forms a blocked surface without a hole through which air moves in the first frame 440. In addition, the opening 442 is a portion corresponding to the hole through which air passes in the first frame 440.

The block member 441 configures a blocked surface to shield the dehumidifying material 430 in the first direction X. In particular, the block member 441 is located closer to the inner mesh 410 than the outer mesh 420 in the first direction X to form a blocked surface to shield the dehumidifying material 430.

The opening 442 configures a through-hole so as not to shield the dehumidifying material 430 in the first direction X. In particular, the opening 442 configures a through-hole on the side closer to the outer mesh 420 than the inner mesh 410 so as not to shield the dehumidifying material 430 in the first direction X.

A plurality of openings 442 can be provided in the first frame 440, and the openings 442 can be formed in all of the ceiling part 401, the first side wall 402, and the second side wall 403.

The air in the connection path F10 flows into the inner space of the dehumidifying block 400 from the rear thereof in the first direction X, and passes through the dehumidifying block 400 while moving forward in the first direction X.

Based on the first direction X, the pressure of the rear of the inner space (the first path F11) of the dehumidifying block 400 is greatest, and the pressure can be reduced toward the front.

A significant portion of the air in the inner space (the first path F11) of the dehumidifying block 400 can move to pass through the rear portion (an area A) and the middle portion (an area B) of the dehumidifying block 400 in the first direction X.

Unlike the present disclosure, if it is assumed that the openings 442 are not formed in the first frame 440, even if the air in the first path F11 flows into the dehumidifying block 400 in the portions (an area C and an area D) adjacent to the first frame 440, the air can flow very weakly or can be stagnant, so that the dehumidifying material 430 in the portions (the area C and the area D) adjacent to the first frame 440 is unable to be utilized.

Unlike this, in the present disclosure, since the openings 442 are formed in the first frame 440, the air in the first path F11 can pass through the dehumidifying block 400 through the openings 442, and the dehumidifying block 400 can be efficiently utilized in the foremost portions thereof (the area C and the area D) in the first direction X.

In particular, since the openings 442 are formed closer to the outer mesh 420 than the inner mesh 410, the air in the inner portion (the area C) can easily move to the outer portion (the area D), and the dehumidifying block 400 can be effectively utilized in all the foremost portions thereof (the area C and the area D) in the first direction X.

Figure 23:
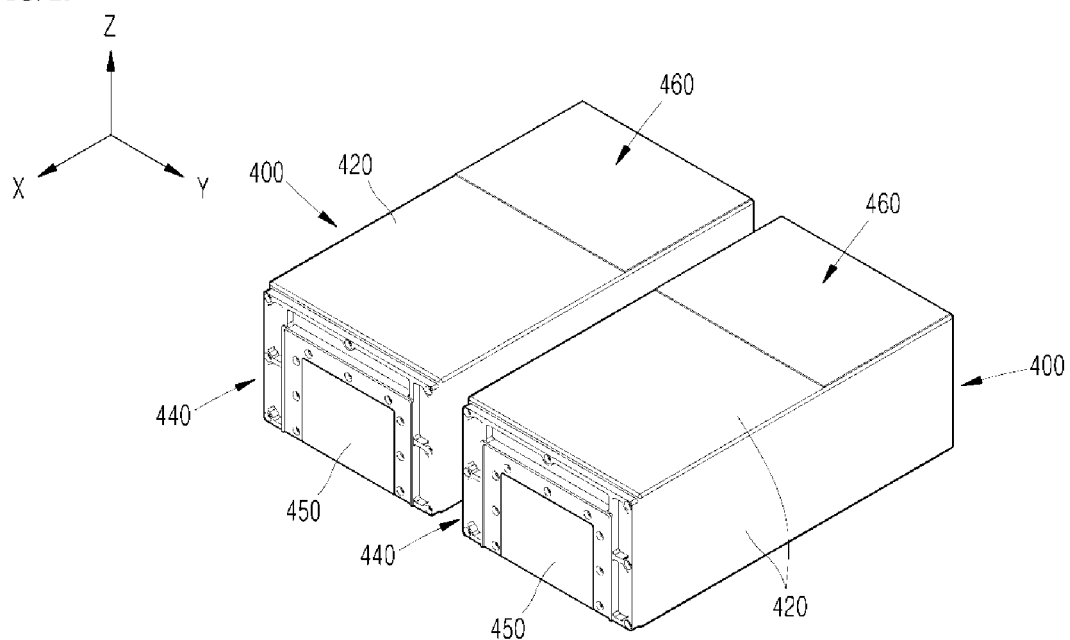
FIGS. 23, 24A, and 24B are perspective views respectively illustrating examples of dehumidifying blocks.
Figure 24A:
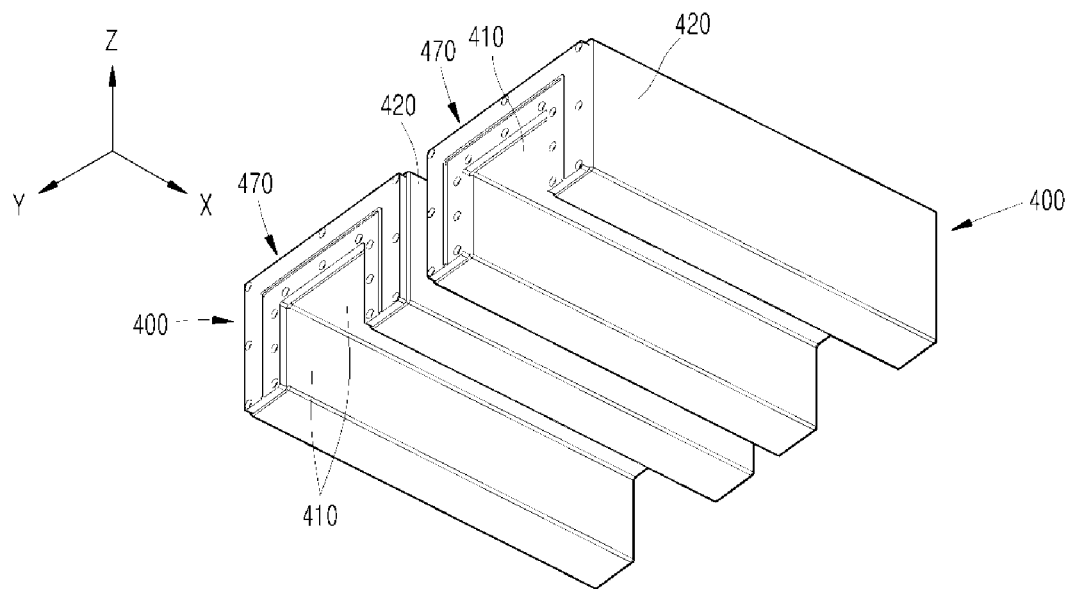
Figure 24B:
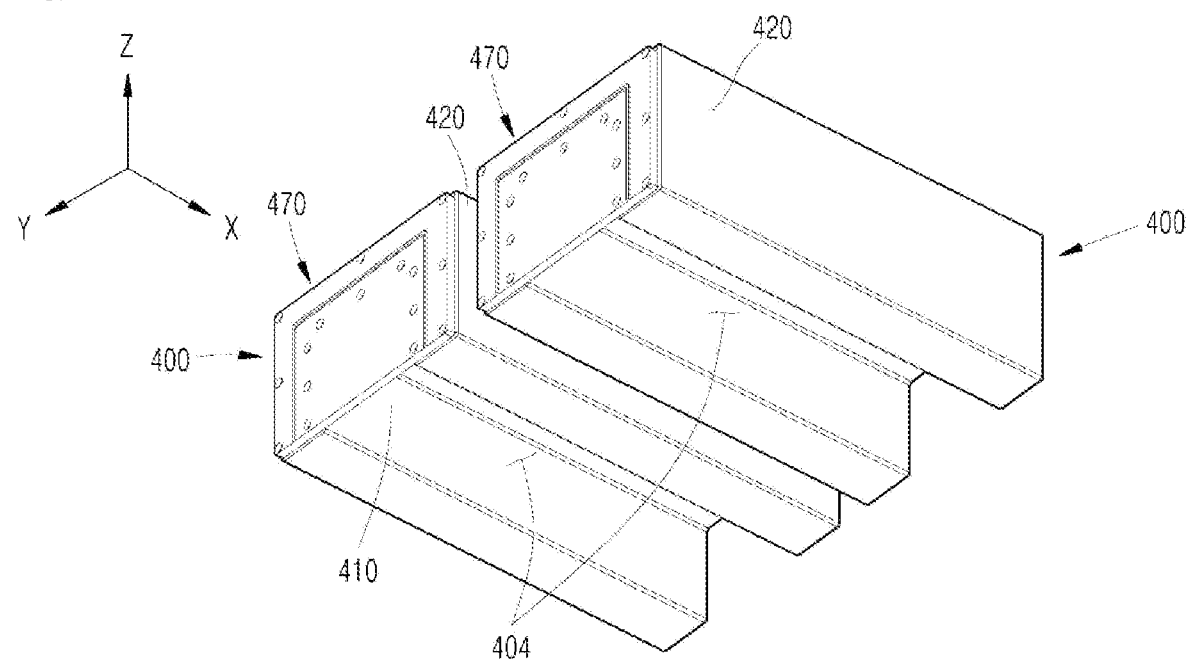
Figure 24C:
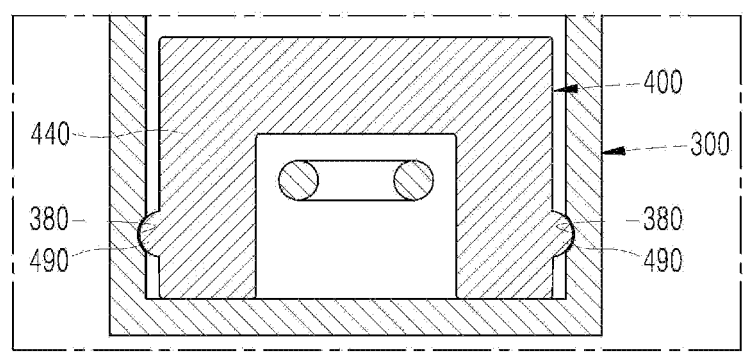
FIGS. 24C and 24D are cross-sectional views schematically illustrating examples of dehumidifying blocks accommodated in a dehumidifying housing.
Figure 24D:
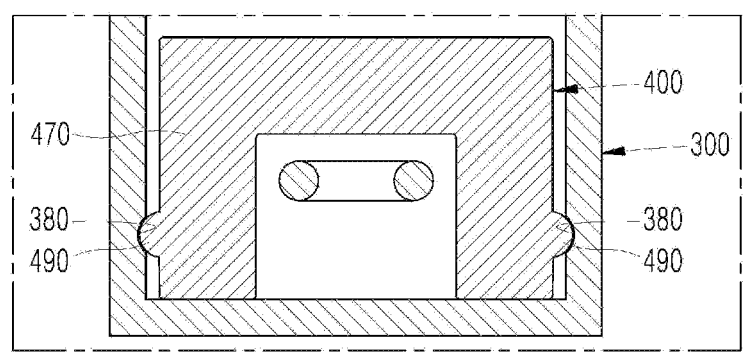

FIGS. 23, 24A, and 24B are perspective views respectively illustrating an example of a dehumidifying block 400. FIGS. 24C and 24D are cross-sectional views schematically illustrating an example of a dehumidifying block 400 accommodated in a dehumidifying housing 300, respectively.

The dehumidifying block 400 can be configured to include a second frame 450 and a third frame 460.

The dehumidifying block 400 can be configured to include a fourth frame 470.

The second frame 450 can be configured to shield the inner space (a first path F11) of the dehumidifying block 400 at the front thereof in the first direction X.

The second frame 450 can configure a front surface of the dehumidifying block 400 in the first direction X. The second frame 450 can be configured in the form of a relatively hard plate, and can be formed of metal, synthetic resin, or the like.

The second frame 450 can be connected to the first frame 440. The second frame 450 can be formed integrally with the first frame 440.

As the second frame 450 is formed in the dehumidifying block 400, the air in the first path F11 moves to pass through the dehumidifying block 400, instead of directly moving forward in the first direction X.

The third frame 460 can be configured in the form of a flat plate, and can be coupled to the outer mesh 420 of the dehumidifying block 400.

The third frame 460 can be coupled to the outer surface of the ceiling part 401. In particular, the third frame 460 can be coupled to the outer surface of the ceiling part 401 so as to be closer to the rear thereof in the first direction X.

The third frame 460 can be formed at a position corresponding to the housing inlet 311 in the vertical direction.

In the case where the third frame 460 is not formed, the air introduced into the inner space (the first path F11) of the dehumidifying block 400 in the upward direction through the housing inlet 311 can move most rapidly to pass through the rear portion (the area A) of the dehumidifying block 400 in the first direction X.

In the case where the third frame 460 is formed, the air introduced into the inner space (the first path F11) of the dehumidifying block 400 through the housing inlet 311 can flow into the rear portion (the area A) of the dehumidifying block 400 in the first direction X, and, in some examples, can collide with the third frame 460 to move to the adjacent portion, that is, the middle portion (the area B) of the dehumidifying block 400 in the first direction X and then pass through the dehumidifying block 400.

As described above, in the case where the third frame 460 is formed in the dehumidifying block 400, the air can sufficiently move to the middle portion (the area B) and the front portion (the area C and area D) of the dehumidifying block 400, as well as to the rear portion (the area A) of the dehumidifying block 400, in the first direction X, thereby enabling contact between the air and the dehumidifying material over the entire dehumidifying block 400 and effectively preventing some of the dehumidifying material from not being utilized.

The fourth frame 470 can configure a rear surface of the dehumidifying block 400 in the first direction X. The fourth frame 470 can be configured in the form of a relatively hard plate, and can be formed of metal, synthetic resin, or the like.

The fourth frame 470 can configure rear surfaces of the ceiling part 401, the first side wall 402, and the second side wall 403 in the first direction X.

The fourth frame 470 is coupled along the edges of the inner mesh 410 and the outer mesh 420. The inner mesh 410 and the outer mesh 420 can be fixed to the fourth frame 470.

Since the inner mesh 410 and the outer mesh 420 are fixed to the fourth frame 470, the overall structure of the dehumidifying block 400 can be stably maintained.

The fourth frame 470 can be configured to shield the inner space 404 (the first path F11) of the dehumidifying block 400 at the rear thereof in the first direction X (see FIG. 24B).

At least one of the first frame 440 and the fourth frame 470 can have a guide protrusion (the second guide protrusion 480) formed to protrude outwards and come into close contact with the inner surface of the dehumidifying housing 300, thereby supporting the same. That is, the above-described second guide protrusion 480 can be formed in the first frame 440 and/or the fourth frame 470.

A fixed protrusion 490 can be formed in at least one of the first frame 440 and the fourth frame 470 so as to protrude outwards. The fixed protrusion 490 can have a hemispherical shape. In addition, a fixed recess 380 that is a concave portion to receive the fixed protrusion 490 can be formed on the inner surface of the dehumidifying housing 300. A plurality of fixed protrusions 490 and a plurality of fixed recesses 380 can be provided, and the plurality of fixed protrusions 490 (or fixed recesses 380) can be formed in the positions facing each other. The fixed protrusion 490 and/or the fixed recess 380 can be made of an elastically deformable material. The protrusion height of the fixed protrusion 490 and/or the depression depth of the fixed recess 380 can be of several mm.

When the dehumidifying block 400 is accommodated and seated inside the dehumidifying housing 300, the fixed protrusion 490 is inserted into the fixed recess 380 to fix the dehumidifying block 400. Accordingly, the dehumidifying block 400 is prevented from moving inside the dehumidifying housing 300, and the second path F12 is stably maintained.

The heater 710 can be configured to be fixed to the machine room 50, and the dehumidifying block 400 can be configured to be replaceable.

The heater 710 can be configured as various devices and structures within a range capable of supplying heat to the dehumidifying material 430.

The heater 710 can be configured as an electric heater. In some implementations, the heater can include a heating element, and can be configured to supply heat to the surroundings while the heating element emits heat by the supplied electric energy. The heater can include a nichrome wire as a heating element.

The heater 710 can be configured to include a free end 711 and a fixed end 712.

The free end 711 can be formed along the first direction X. In the heater 710, the free end 711 is made of a heating element.

The fixed end 712 can be formed in a shape bent downwards from the free end 711 at the front in the first direction X.

The fixed end 712 can be electrically connected to a power source, and as electric energy is supplied to the free end 711 through the fixed end 712, the free end 711 can emit heat.

When the shoe care device 1 is viewed in the second direction Y, the heater 710 can be formed in a "⌐" shape. In addition, since the dehumidifying block 400 is configured to include the ceiling part 401, the first side wall 402, and the second side wall 403, and has a "⊓" shape in its cross-section, when the dehumidifying block 400 is seated inside the dehumidifying housing 300, the heater 710 is accommodated in the first path F11 that is the inner space 404 of the dehumidifying block 400.

Accordingly, the shoe care device 1 can include the heater 710 that is located in the inner space 404 of the dehumidifying block 400, where the dehumidifying block 400 can be easily attached and detached.

The shoe care device 1 can be configured to include a heater flange 720 to which the heater 710 is fixed.

The heater flange 720 can be made of metal.

The heater flange 720 can be configured to include a horizontal plate 721 and a vertical plate 722.

The horizontal plate 721 is configured in the form of a flat plate in the horizontal direction. The horizontal plate 721 can be fixed to the housing bottom plate 310 at the front in the first direction X.

In addition, the fixed end 712 of the heater 710 is fixed to the horizontal plate 721 of the heater flange 720.

The vertical plate 722 of the heater flange 720 extends upwards from the horizontal plate 721. The vertical plate 722 can be configured in a form bent from the horizontal plate 721. The vertical plate 722 can be configured to shield the inner space of the dehumidifying block 400. The vertical plate 722 can be configured to shield or seal the first path F11, which is the inner space 404 of the dehumidifying block 400, at the front in the first direction X.

The vertical plate 722 can be configured to be in close contact with or close to the front surface of the dehumidifying block 400 in the first direction X.

The vertical plate 722 can be spaced forward apart from the front surface of the dehumidifying block 400 in the first direction X to form a gap (g) between the vertical plate 722 and the dehumidifying block 400 (see FIG. 22B). In this case, the gap (g) between the vertical plate 722 and the dehumidifying block 400 can be configured to be very small. In the case where the dehumidifying block 400 is configured to include the first frame 440, the distance between the vertical plate 722 and the first frame 440 can be very small.

In some implementations, the distance between the vertical plate 722 and the dehumidifying block 400 (or the first frame 440) can be in the range of $1/10$ to $1/200$ of the width of the first path F11 (the distance between the first side wall 402 and the second side wall 403). For example, the distance between the vertical plate 722 and the dehumidifying block 400 (or the first frame 440) can be about 1 mm or less. When the heater 710 is operated, the heater flange 720 can be heated, and the gap (g) can prevent the heat of the vertical plate 722 from being directly transferred to the dehumidifying block 400 (particularly, the first frame 440), thereby preventing damage to the first frame 440 due to heat. In addition, a small amount of air among the air in the first path F11 can escape through the gap, and thus, it can be possible to help to prevent the pressure in the first path F11 from excessively increasing to an unintended level.

Figure 25:
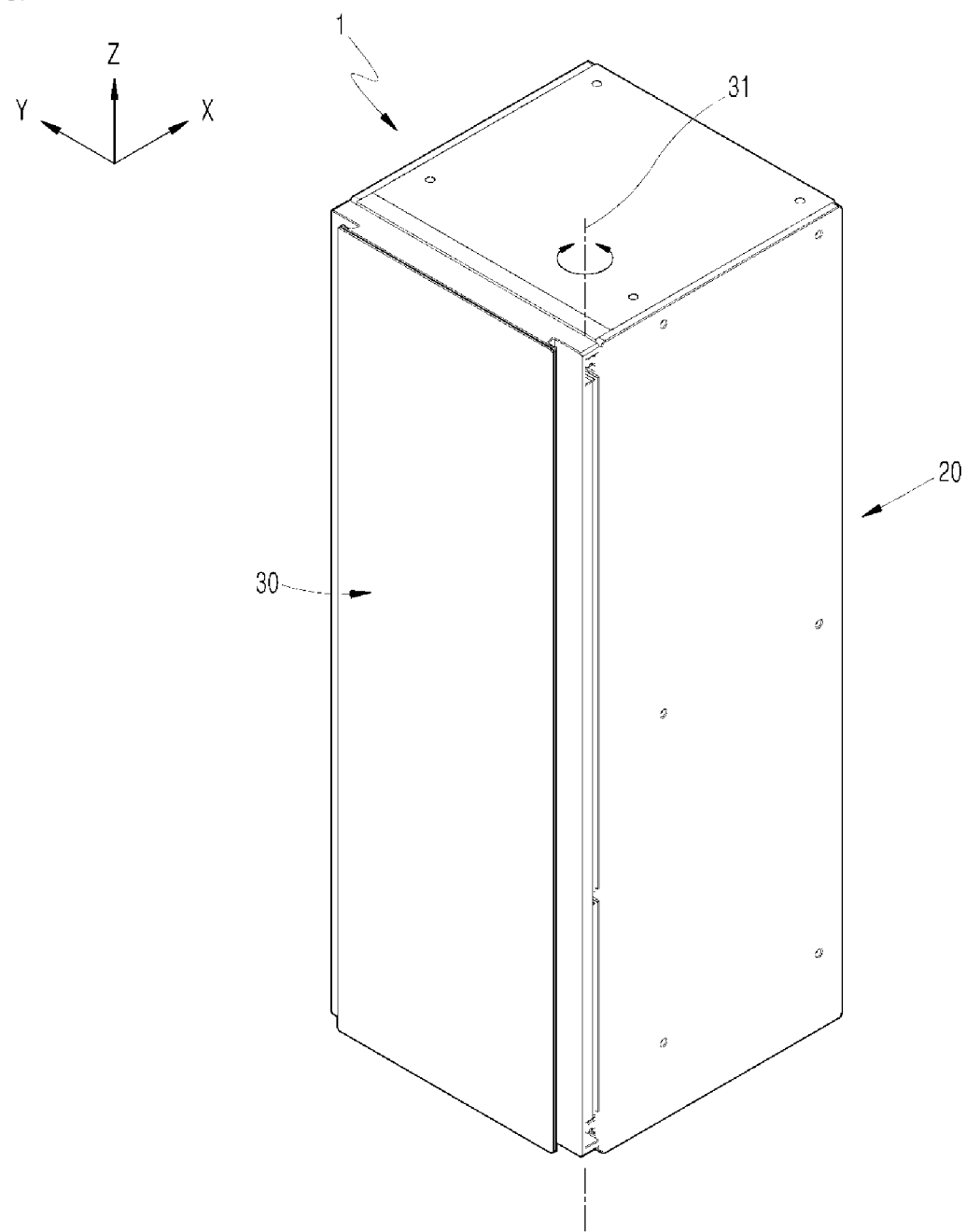
FIG. 25 is a perspective view illustrating an example of a shoe care device.

FIG. 25 is a perspective view illustrating a shoe care device 1.

Figure 26:
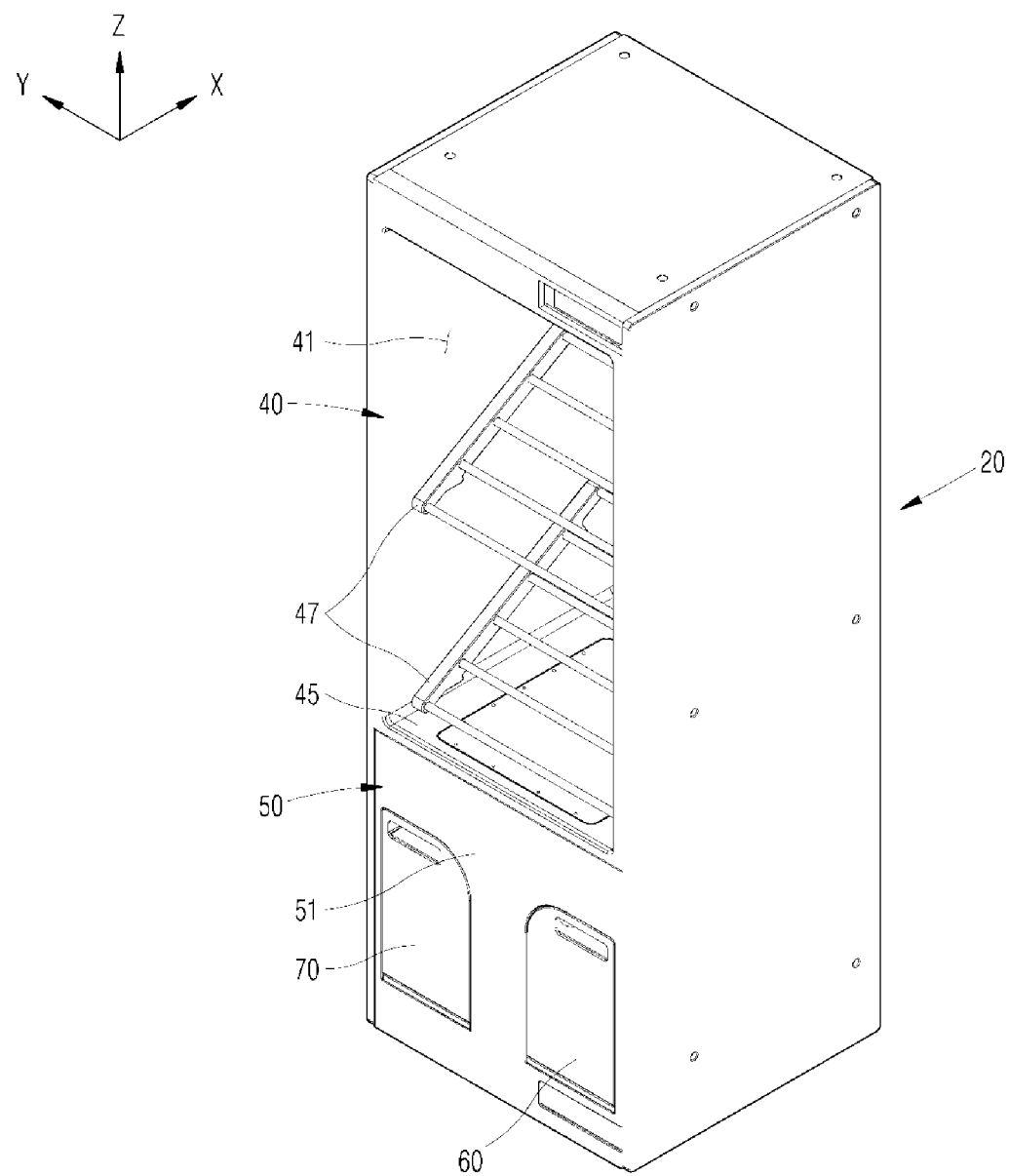
FIG. 26 is a perspective view illustrating the shoe care device in FIG. 25 without a door to show the inside thereof.

FIG. 26 is a perspective view illustrating the state in which a door 30 is removed from the shoe care device 1 in FIG. 25 to show the inside thereof.

Figure 27:
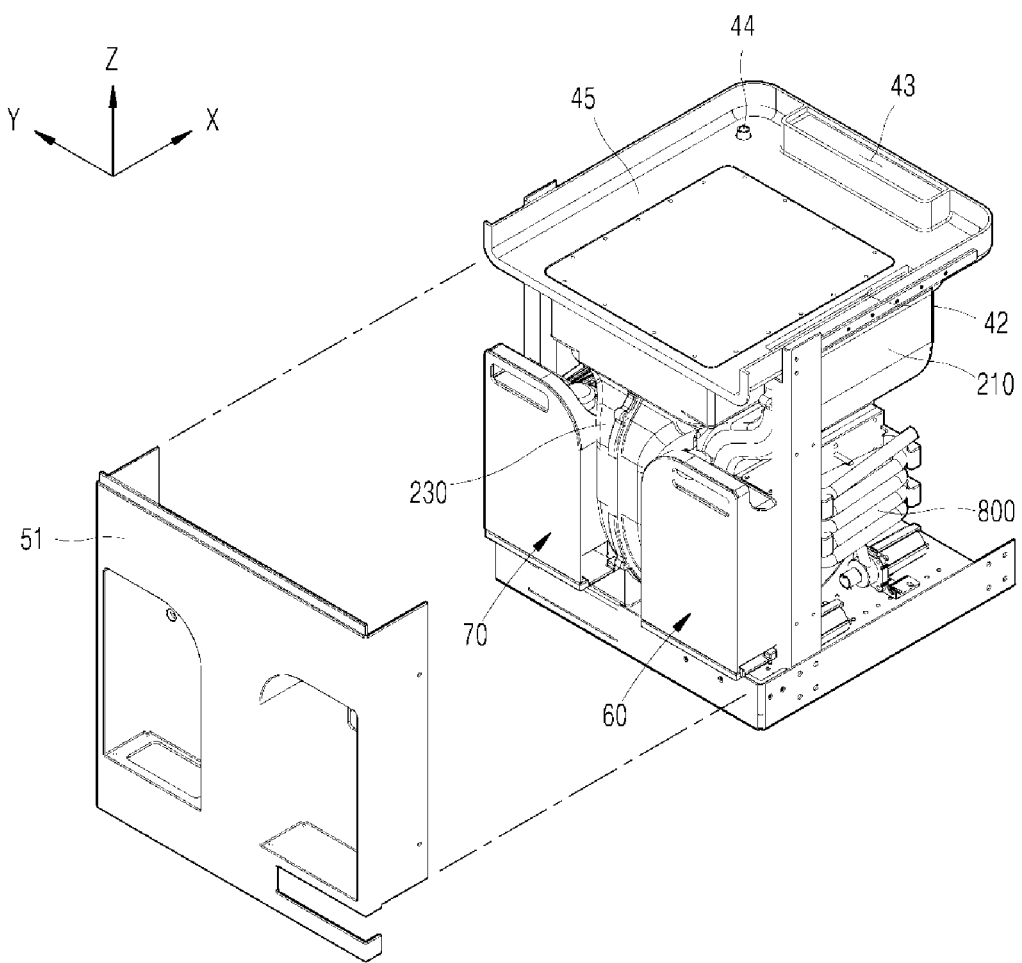
FIG. 27 is a perspective view illustrating an example of configurations provided in a machine room in FIG. 26.
Figure 28:
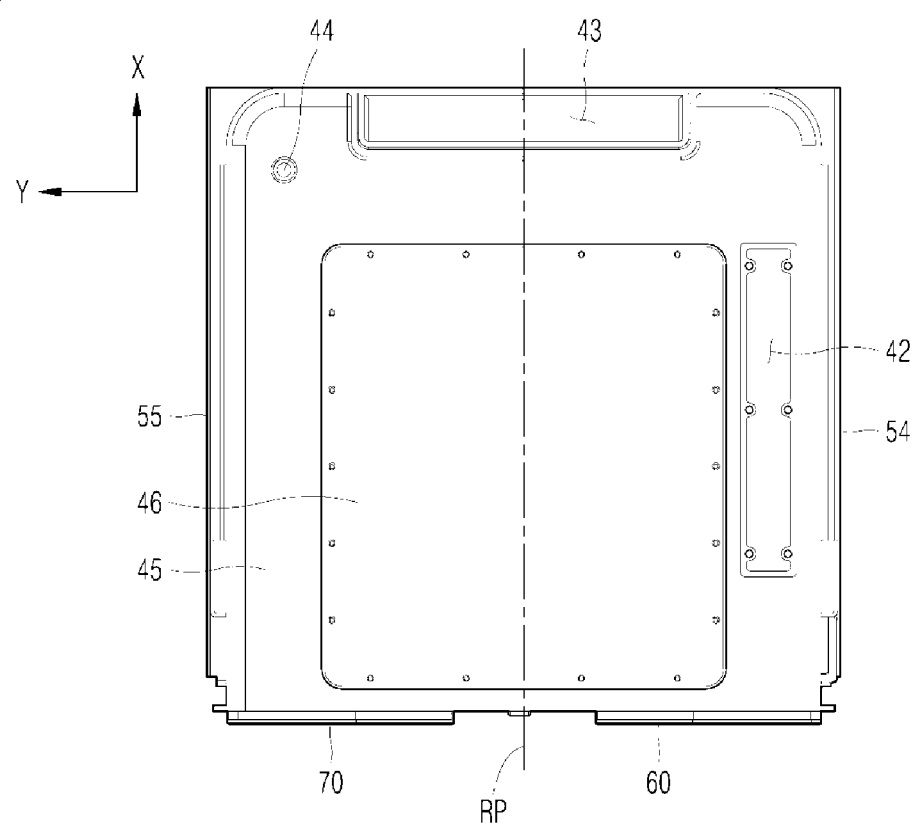
FIG. 28 is a view illustrating an example of a bottom of an inner cabinet of the shoe care device in FIG. 26.

FIG. 27 is a perspective view illustrating the configurations provided in the machine room 50 in FIG. 28.

FIG. 28 is a view illustrating a bottom of an inner cabinet 40 of the shoe care device 1 in FIG. 26.

Figure 29A:
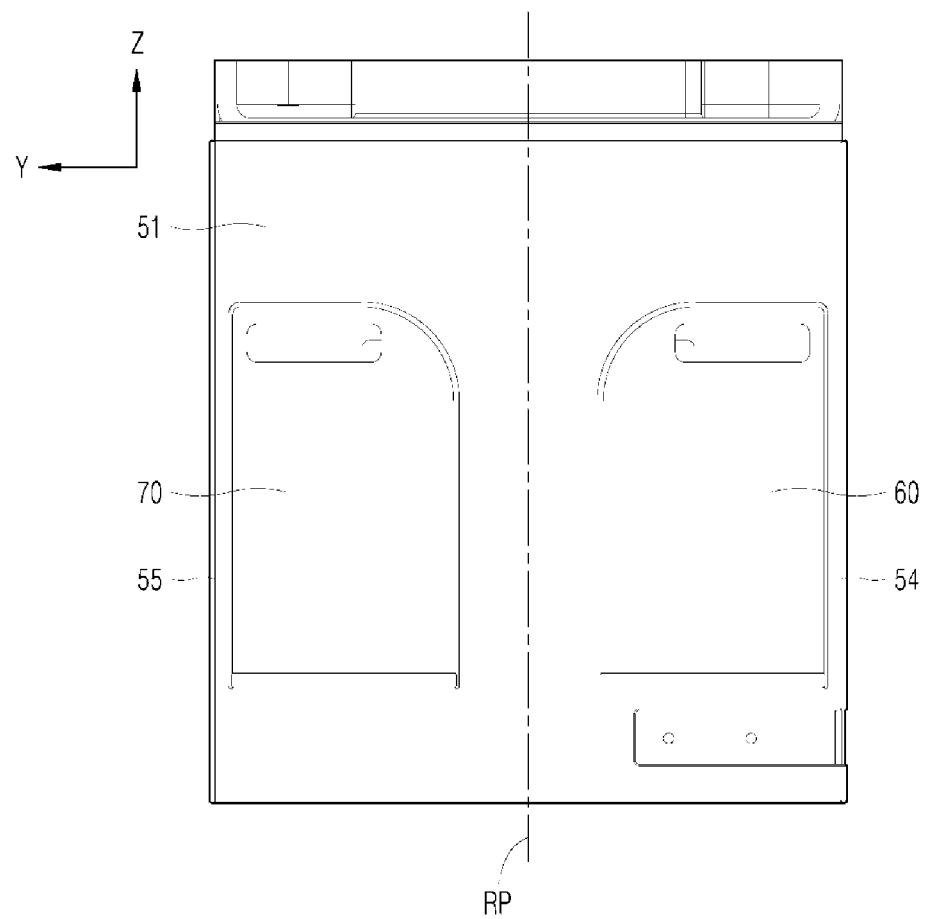
FIG. 29A is a view illustrating an example of a first wall in a shoe care device viewed from the front.
Figure 29B:
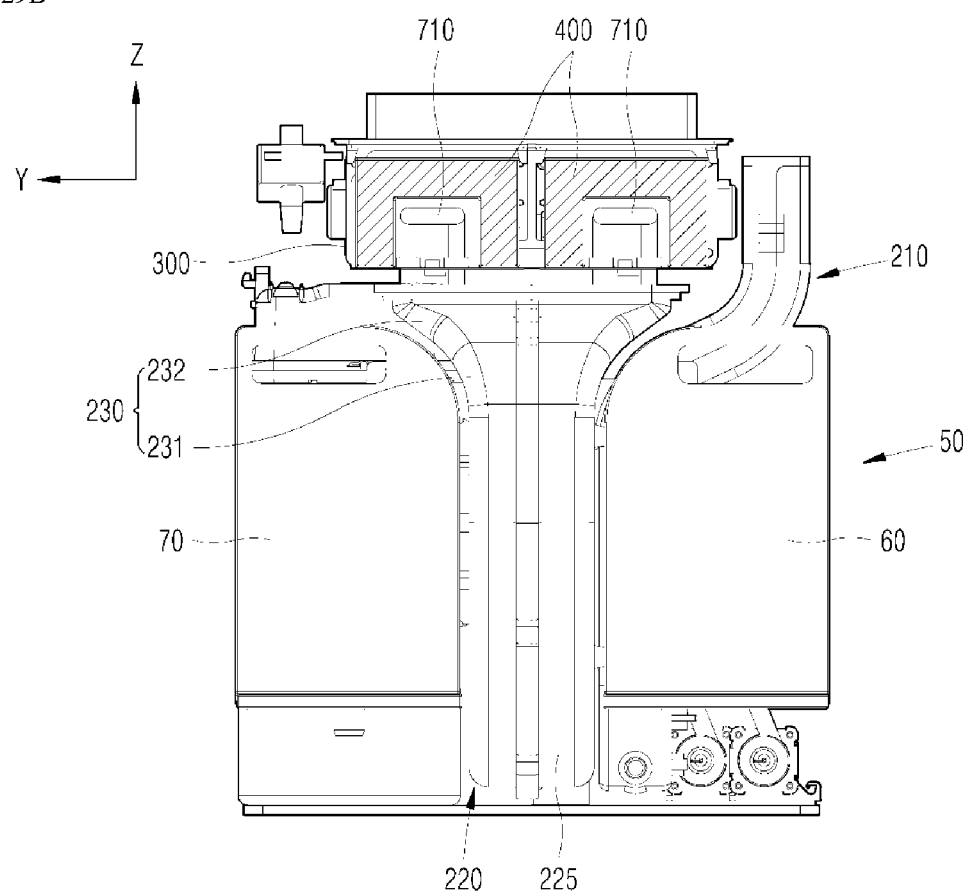
FIG. 29B is a view excluding the first wall from FIG. 29A.

FIG. 29A is a view of a first wall 51 in a shoe care device 1 viewed from the front, and FIG. 29B is a view excluding the first wall 51 from FIG. 29A.

The outlet 42 can be configured in the form of a long slot in the first direction X along the left edge of the cabinet bottom plate 45 or along the right edge of the cabinet bottom plate 45.

In addition, the inlet 43 can be formed along the rear edge of the cabinet bottom plate 45. That is, the inlet 43 can be located relatively far from the door 30 in the cabinet bottom plate 45.

The water supply tank 60 and the drain tank 70 can be disposed on both sides of a reference plane RP parallel to the vertical direction and parallel to the first direction X.

The blowing duct 230 can be disposed on the reference plane RP.

Figure 30A:
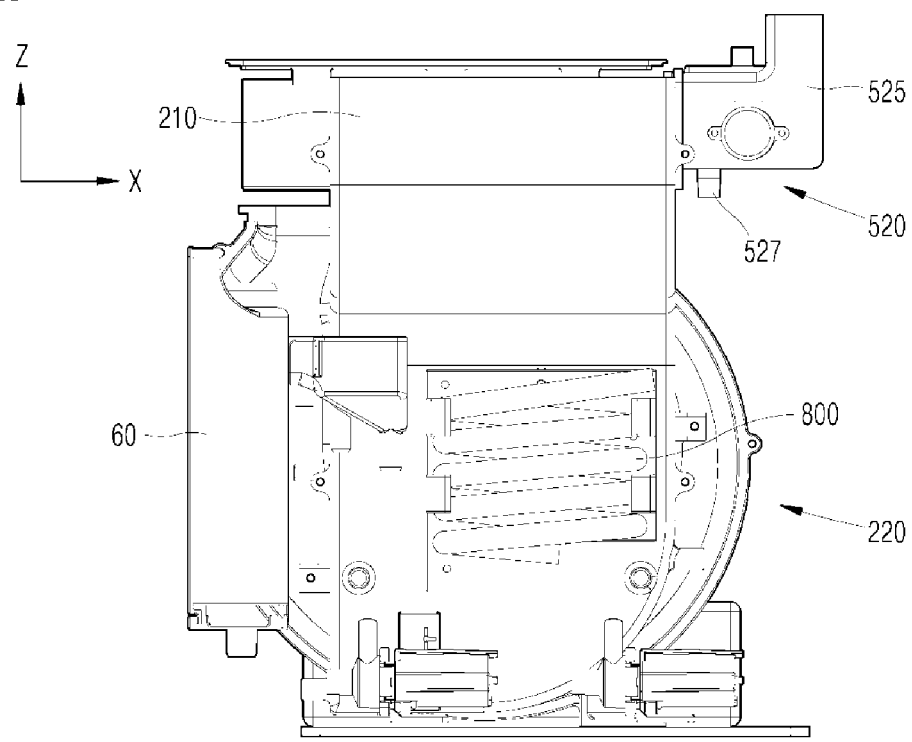
FIGS. 30A and 30B are views illustrating an example of a machine room of the shoe care device shown in FIG. 29B when viewed from opposite sides.
Figure 30B:
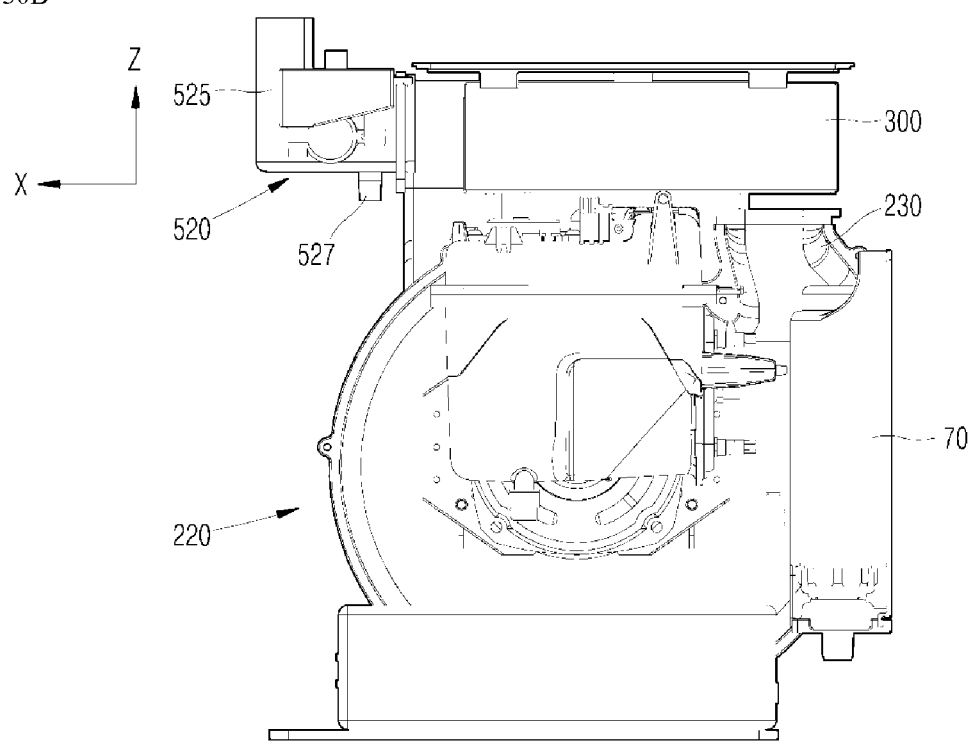

FIGS. 30A and 30B are views illustrating a machine room 50 of the shoe care device 1 shown in FIG. 29B when viewed from opposite sides.

Figure 31A:
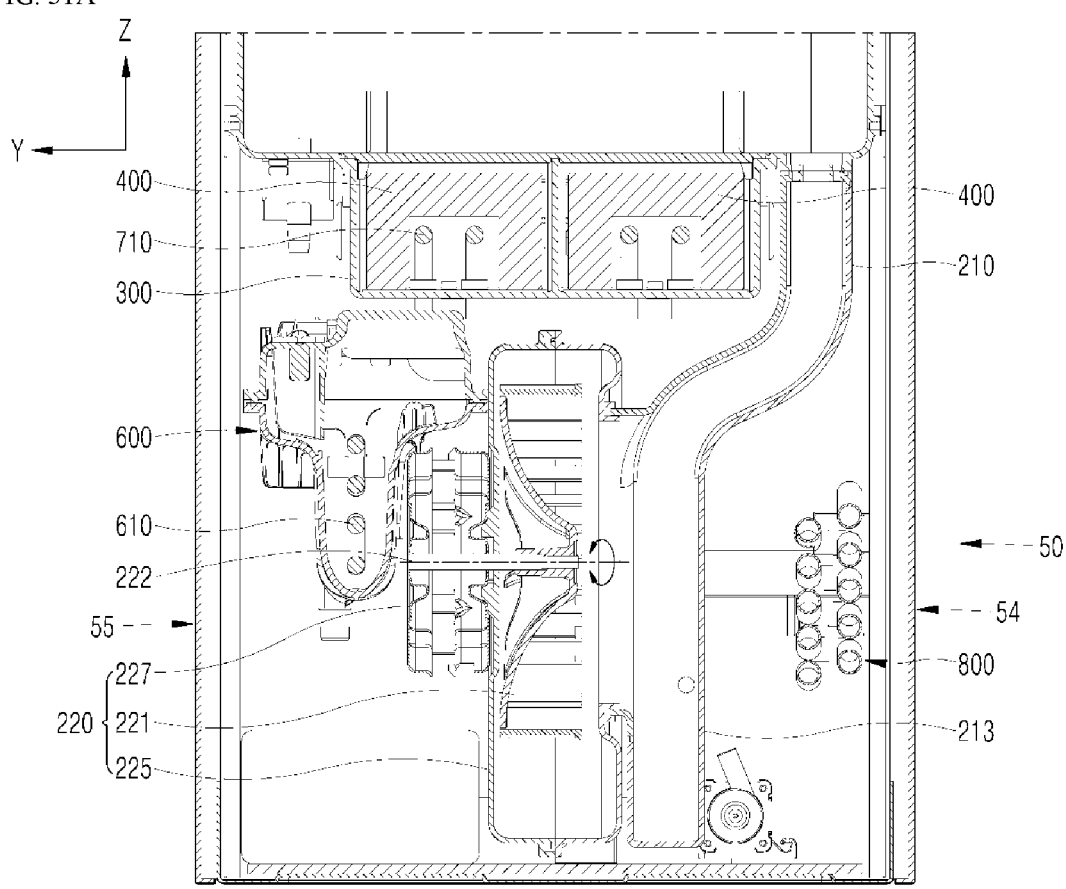
FIGS. 31A and 31B are cross-sectional views illustrating the shoe care device shown in FIG. 25.
Figure 31B:
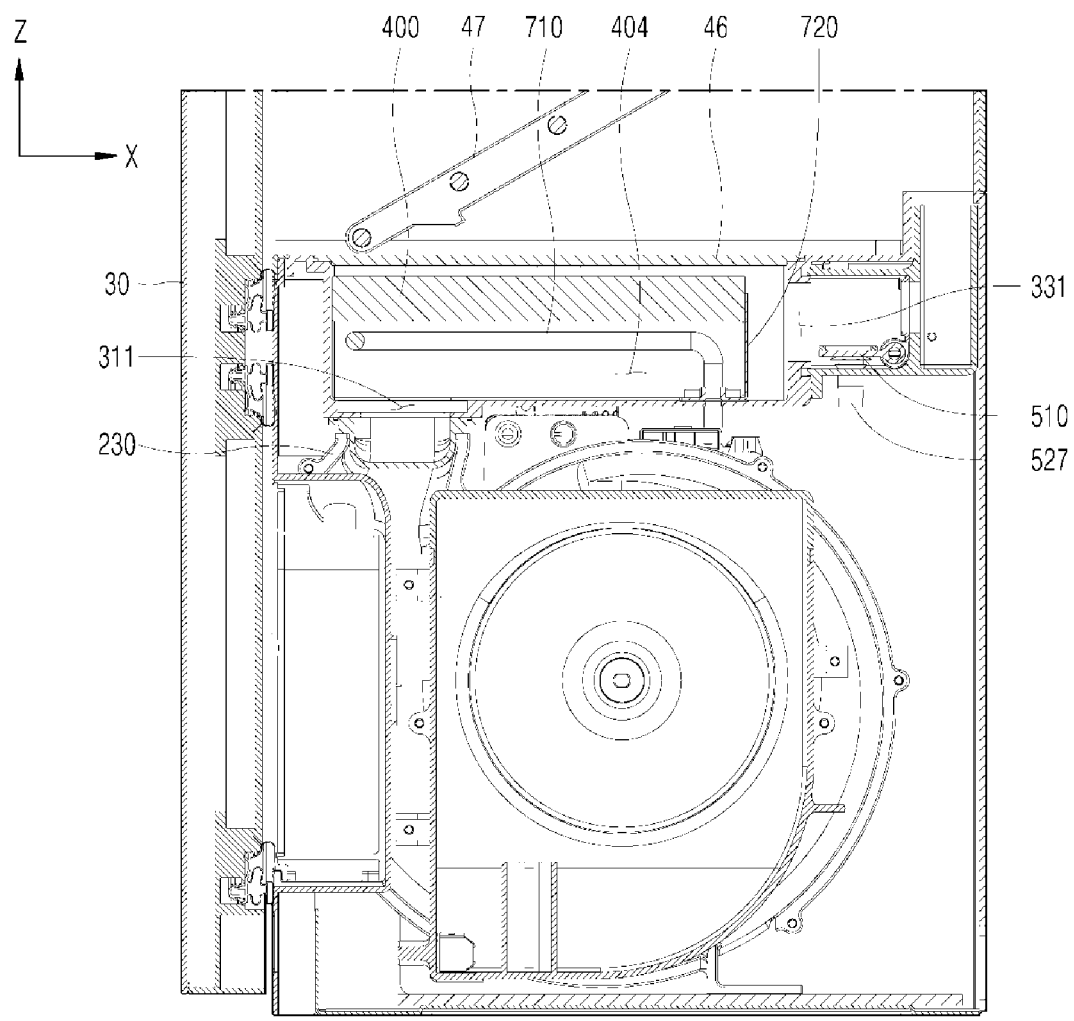

FIGS. 31A and 31B are cross-sectional views illustrating the shoe care device 1 shown in FIG. 25.

The machine room 50 can be configured to include a second wall 54 and a third wall 55. The second wall 54 and the third wall 55 configure both wall surfaces facing each other in the machine room 50. The second wall 54 and the third wall 55 can be erected in the vertical direction, or can be erected in the substantially vertical direction.

In the case where the first wall 51 configures the front wall of the machine room 50, the second wall 54 can configure the left wall of the machine room 50, and the third wall 55 can configure the right wall of the machine room 50.

In some implementations, the condenser 800 can be in close contact with the inner surface of the left or right wall of the machine room 50. That is, the condenser 800 can be in close contact with the inner surface of the second wall 54 or can be in close contact with the inner surface of the third wall 55.

The second wall 54 and the third wall 55 can be made of a metal having excellent thermal conductivity. In the case where the condenser 800 is coupled to the second wall 54 to be in close contact therewith, the second wall 54 can be made of metal having excellent thermal conductivity, and in the case where the condenser 800 is coupled to the third wall 55 to be in close contact therewith, the third wall 55 can be made of a metal having excellent thermal conductivity.

Accordingly, condensing of water vapor moving through the condenser 800 can be effectively performed.

Figure 32:
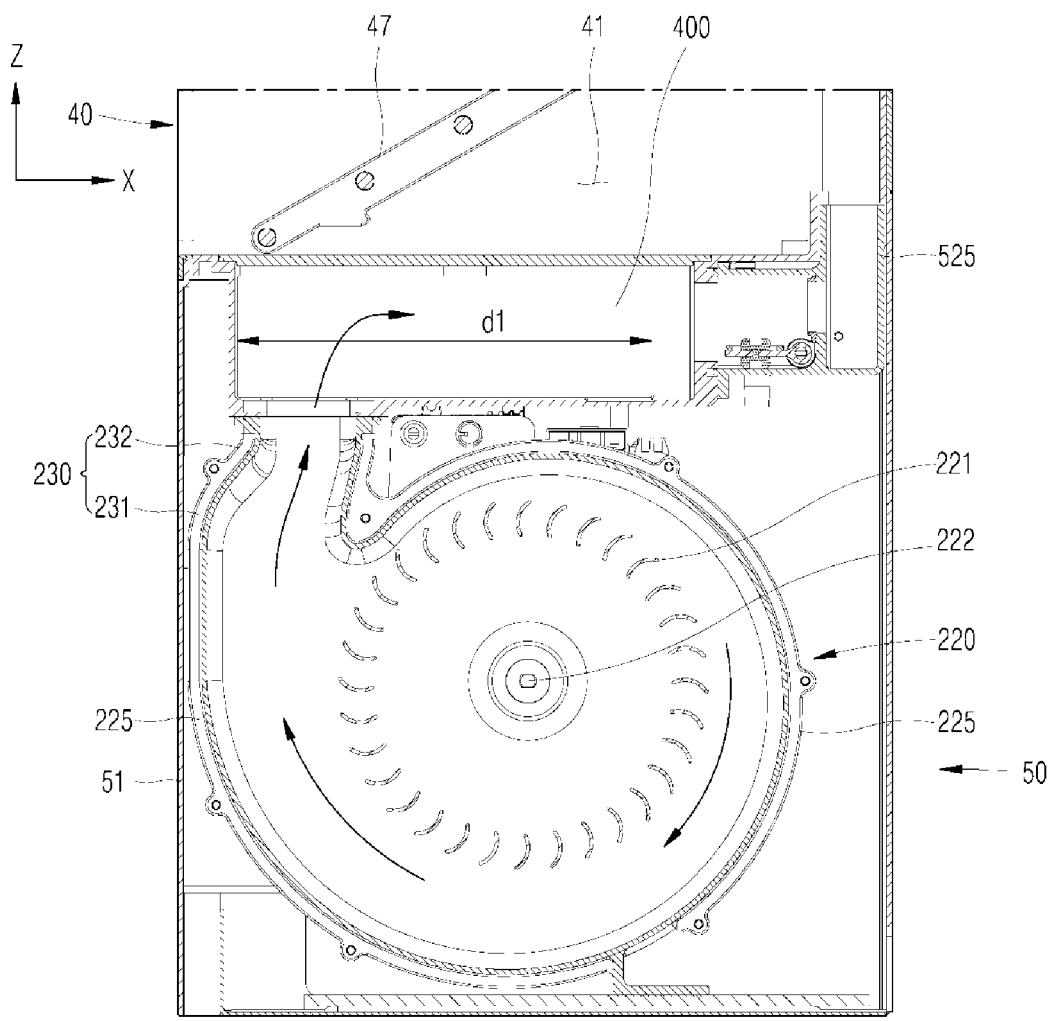
FIG. 32 is a cross-sectional view illustrating the shoe care device shown in FIG. 26.

FIG. 32 is a cross-sectional view illustrating the shoe care device 1 shown in FIG. 26.

The blowing duct 230 can have a structure that is convex backwards in the first direction X.

The blowing duct 230 can be configured to be located between the water supply tank 60 and the drain tank 70 under the dehumidifying block 400.

Accordingly, the blowing duct 230 can be positioned in the rearmost portion of the machine room 50 in the first direction X, and the diameter of the blowing housing 225 can be configured as large as possible, and furthermore, the diameter of the blowing fan 221 provided inside the blowing housing 225 can be configured to be large.

Therefore, it can be possible to provide the blower 220 having a sufficiently large output, and to provide the blowing housing 225 having a relatively large diameter even though the thickness thereof is relatively small, and a sufficient amount of air moving the connection path F10 per unit time can be secured.

In addition, it can be possible to prevent occurrence of an unintentional path resistance when the air in the connection path F10 passes through the dehumidifying block 400.

In addition, since the blowing duct 230 is positioned between the water supply tank 60 and the drain tank 70 under the dehumidifying block 400, it can be possible to configure a shoe care device 1 having the following structure.

As the length d1 of the dehumidifying block 400 and the first path F11 becomes longer in the first direction X, the size of the dehumidifying block 400 and the size of the first path F11 can increase, and the dehumidifying capacity of the dehumidifying material per unit time can also be improved.

Accordingly, the length of the dehumidifying block 400 and the first path F11 in the first direction X needs to be greater than or equal to a predetermined length.

In the case where the blowing duct 230 is located between the water supply tank 60 and the drain tank 70, based on the first direction X, the inner surface of the rear end of the blowing duct 230 and/or the inner surface of the rear end of the blowing housing 225 can be configured to be located at the same position as the rear end of the first path F11 or further behind than the same while securing the length d1 of the dehumidifying block 400 and the first path F11 in the first direction X.

In this case, the air can naturally flow through the blowing housing 225, the blowing duct 230, and the first path F11 in sequence, and the air in the first path F11 can effectively pass through the dehumidifying block 400 over the entire length d1 of the dehumidifying block 400 (the length of the dehumidifying block 400 in the first direction X).

As described above, the blowing duct 230 can be divided into a lower blowing duct 231 and an upper blowing duct 232.

Based on the first direction X, the width of the lower blowing duct 231 can be configured to be greater than the width of the upper blowing duct 232, and the rear end of the lower blowing duct 231 can be configured to be located behind the rear end of the upper blowing duct 232.

In addition, the width of the blowing housing 225 can be configured to be equal to or less than the width of the lower blowing duct 231 in the second direction Y.

Accordingly, even if the width of the blowing housing 225 is configured to be small in the second direction Y, the air inside the blowing housing 225 can be transferred into the blowing duct 230 at a stable flow rate. In addition, the air sequentially transferred into the blowing housing 225, the blowing duct 230, and the dehumidifying block 400 (the first path F11) moves to correspond to the rotational direction of the blowing fan 221, thereby obtaining stable air flow in the connection path F10.

Figure 33A:
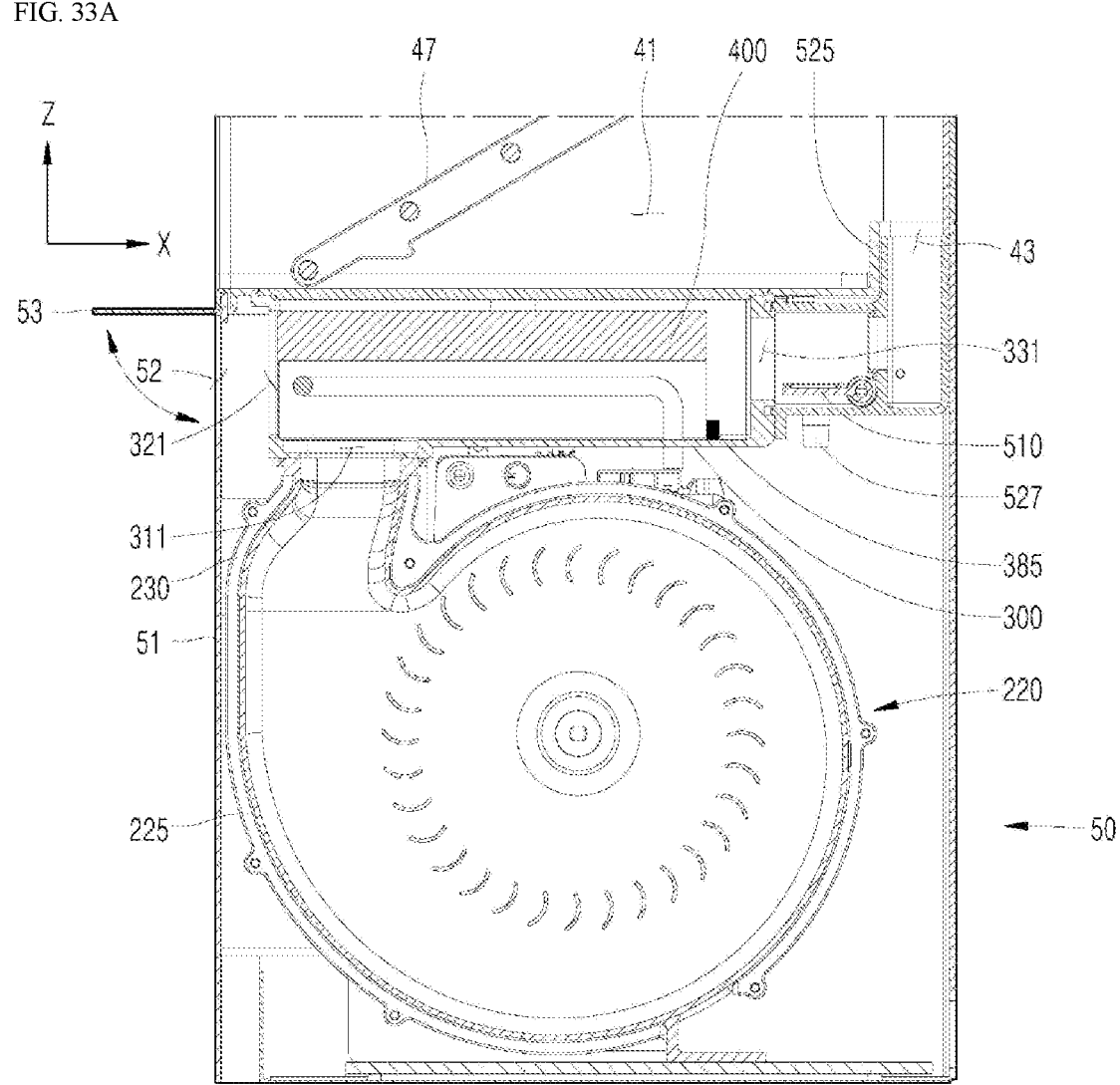
FIGS. 33A and 33B are cross-sectional views respectively illustrating an example of a shoe care device.
Figure 33B:
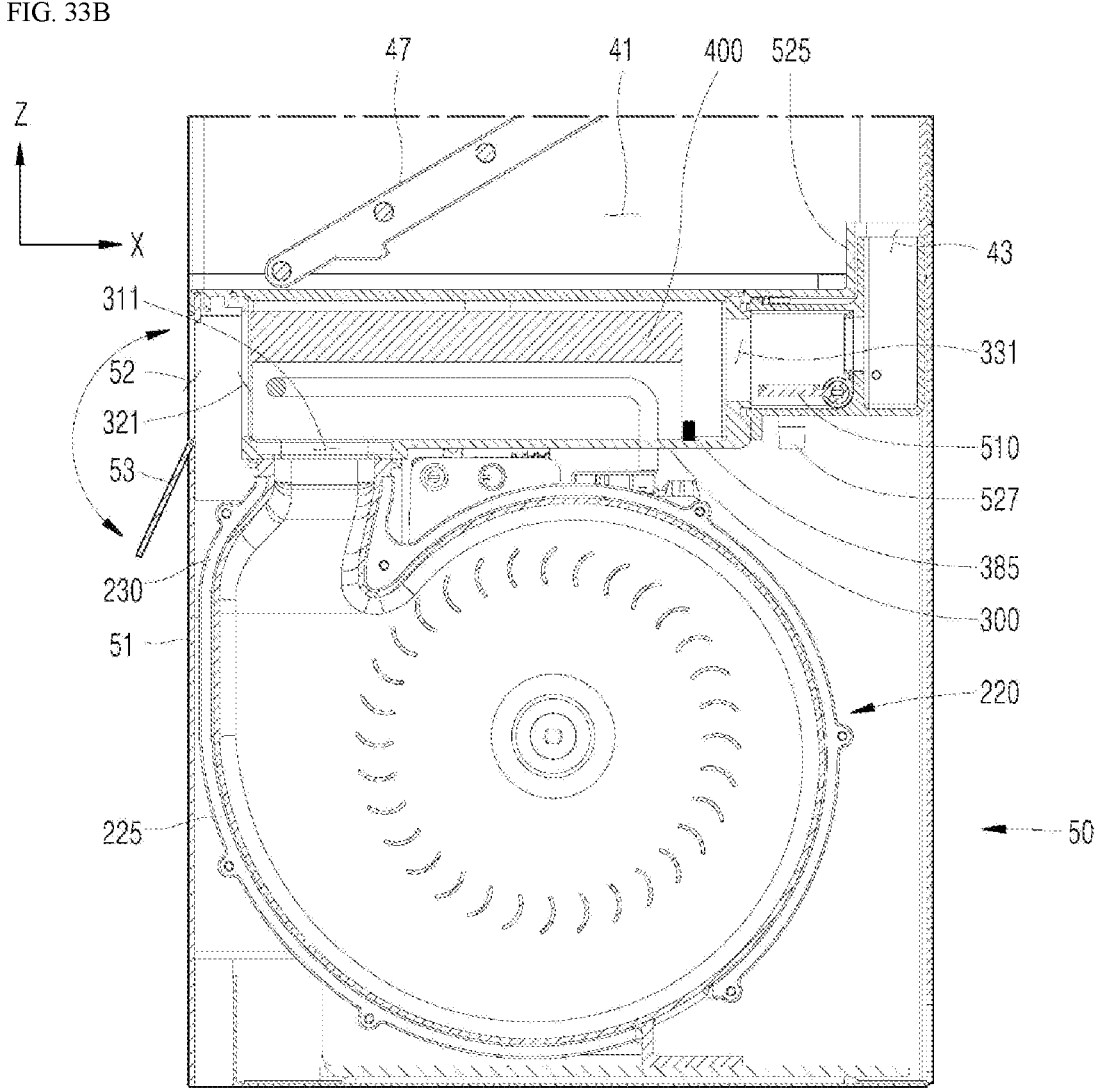

FIGS. 33A and 33B are cross-sectional views respectively illustrating a shoe care device 1.

Figure 33C:
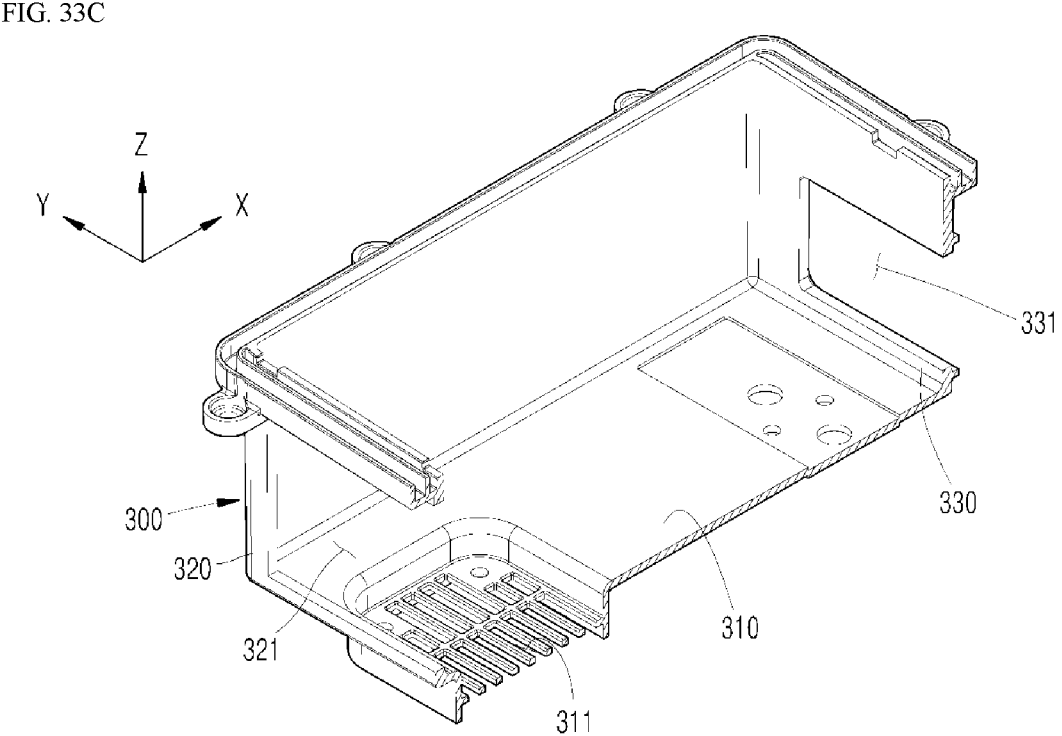
FIG. 33C is a cross-sectional perspective view illustrating an example of a dehumidifying housing provided in the shoe care device in FIGS. 33A and 33B.

FIG. 33C is a cross-sectional perspective view illustrating a dehumidifying housing 300 provided in the shoe care device 1 in FIGS. 33A and 33B.

A replacement hole 52 can be formed in the first wall 51. The replacement hole 52 configures a through-hole in the first wall 51 such that the dehumidifying block 400 can be inserted or taken out therethrough in a direction parallel to the first direction X.

The shoe care device 1 can be configured to include a replacement door 53.

The replacement door 53 can be configured to open and close the replacement hole 52. The replacement door 53 can be coupled to the first wall 51 in various ways making it possible to open and close the replacement hole 52.

The replacement door 53 can be slidably coupled to the machine room 50, or the replacement door 53 can be coupled to the machine room 50 by a hinge.

When the replacement door 53 is coupled to the machine room 50 by a hinge, the rotation axis of the replacement door 53 can be configured in the horizontal direction, or can be configured in the vertical direction.

In the case where a plurality of dehumidifying blocks 400 is provided, a plurality of replacement holes 52 and a plurality of replacement doors 53 can be provided. In the case where a pair of dehumidifying blocks 400 is provided, a pair of replacement holes 52 and a pair of replacement doors 53 can also be provided.

A pair of dehumidifying blocks 400, a pair of replacement holes 52, and a pair of replacement doors 53 can be disposed on both sides of the reference plane RP, and can be disposed above the water supply tank 60 and the drain tank 70.

In the case where the replacement hole 52 and the replacement door 53 are provided in the shoe care device 1, a rear hole 321, which is a through-hole through which the dehumidifying block 400 can move, is formed in the rear dehumidifying material wall 320 of the dehumidifying housing 300.

In some implementations, when the dehumidifying block 400 is inserted into and drawn out of the shoe care device 1 in a direction parallel to the first direction X, the dehumidifying block 400 can slide in the first direction X.

The dehumidifying housing 300 can have a stopper 385 formed thereon. The stopper 385 can be formed to protrude inward from the inner surface of the dehumidifying housing 300. In some implementations, the stopper 385 can be configured to protrude upwards from the housing bottom plate 310. The stopper 385 limits the movement of the dehumidifying block 400 inserted into the dehumidifying housing 300 such that the dehumidifying block 400 moves only to a predetermined point in the first direction X. That is, the stopper 385 prevents continuous movement of the dehumidifying block 400 in the first direction X. In some implementations, the stopper 385 can be configured such that the dehumidifying block 400 moves only to a predetermined point where the dehumidifying block 400 is spaced apart from the front dehumidifying material wall 330.

In the case where the replacement hole 52 and the replacement door 53 are provided in the shoe care device 1, the aforementioned dehumidifying material cover 46 may not be provided. In this case, the distance between the cabinet bottom plate 45 and the dehumidifying block 400 can be constantly maintained, and the second path F12 can be stably maintained.

In addition, when the dehumidifying block 400 is replaced in the shoe care device 1, the replacement hole 52 can be opened to replace the dehumidifying block 400, instead of opening the inner cabinet 40.

The shoe care device 1 can be configured to include an inner cabinet 40, an outlet 42, an inlet 43, an air supplier 10, and a controller 80.

The inner cabinet 40 has an accommodation space 41 formed to accommodate shoes, and the outlet 42 and the inlet 43 can be formed therein.

The outlet 42 is formed on one portion of the inside of the inner cabinet 40 to suck the air from the accommodation space 41, and the air in the inner cabinet 40 can flow to the connection path F10 through the outlet 42.

The inlet 43 can be formed on the opposite portion of the inside of the inner cabinet 40 to supply air to the accommodation space 41, and the air passing through the connection path F10 can flow back into the inner cabinet 40 through the inlet 43.

The air supplier 10 blows the air in the accommodation space 41, and a pair of dehumidifying materials 430 can be disposed to be separated from each other on the path of the blown air, and the pair of dehumidifying materials 430 can be heated by the same.

In this case, as the dehumidifying material 430 is heated, the moisture adsorbed onto the dehumidifying material 430 is separated so that the dehumidifying material 430 can be regenerated into the state capable of performing a dehumidifying function.

Figure 34:
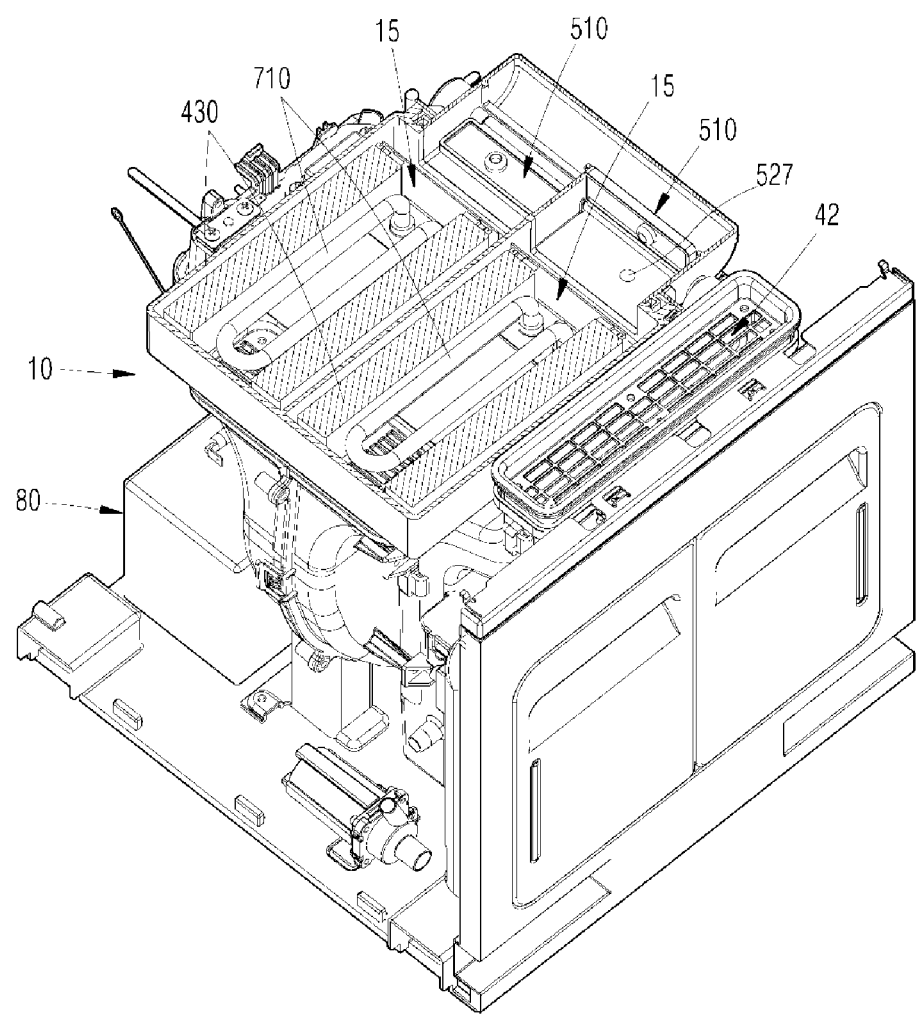
FIG. 34 is a perspective view illustrating an air supplier of the shoe care device shown in FIG. 2A.

In some examples, as shown in FIG. 34, the air supplier 10 can be configured to include a duct, a blower 220, a dehumidifying housing 300, a heater 710, a damper housing 520, and a damper 510, which are disposed inside the machine room 50.

In particular, in the air supplier 10, a connection path F10 through which air circulates between the outlet 42 and the inlet 43 and a regeneration path F20 through which the air passing through the dehumidifying material 430 is blown to a portion other than the inlet 43 can be formed to correspond to the respective dehumidifying materials 430.

Accordingly, the air in the accommodation space 41 can be blown by the air supplier 10 to flow to the connection path F10 or the regeneration path F20, respectively, while passing through the respective separated dehumidifying materials 430.

The controller 80 can control the air supplier 10 such that the connection path F10 and the regeneration path F20 are selectively opened and closed depending on whether or not each dehumidifying material 430 is heated.

That is, the connection path F10 and the regeneration path F20 can be selectively opened and closed by the controller 80 depending on whether or not the dehumidifying material 430 is in the state of being regenerated.

As described above, in the shoe care device 1, the dehumidifying material 430 can be disposed in the air supplier 10 to capture moisture and bacteria in the blown air, and the dehumidifying material 430 can be heated to regenerate in the air supplier 10, thereby adequately maintaining the performance for processing shoes.

In addition, in the shoe care device 1, since the connection path F10 through which the air circulates is formed between the outlet 42 and the inlet 43 that are formed inside the inner cabinet 40, it can be possible to help to prevent the user from being exposed to the air used in dehumidification and deodorization of shoes.

In addition, in the shoe care device 1, a pair of dehumidifying materials 430 can be disposed in the air supplier 10, and the connection path F10 and the regeneration path F20 can be respectively formed in the dehumidifying materials 430, and the connection path F10 and the regeneration path F20 can be selectively opened and closed according to the need for a dehumidifying mode and a regeneration mode, so the shoe care device 1 can be operated in an optimal state depending on the situation, thereby further improving the efficiency of processing shoes.

Specifically, in the shoe care device 1, the air supplier 10 can be configured to include a chamber 15, a heater 710, a drying path hole 529, a regeneration path hole 527, and a damper 510, and can further include a condenser 800.

A pair of chambers 15 can be provided as separated spaces on the connection path F10 to separately accommodate the respective dehumidifying materials 430. This chamber 15 can be configured to include a portion of a dehumidifying housing 300 and a portion of a damper housing 520, as shown in FIG. 34.

The heater 710 can be installed in each chamber 15 to heat the dehumidifying material 430, and can be disposed in the connection path F10 so as to be adjacent to the dehumidifying material 430.

Figure 36:
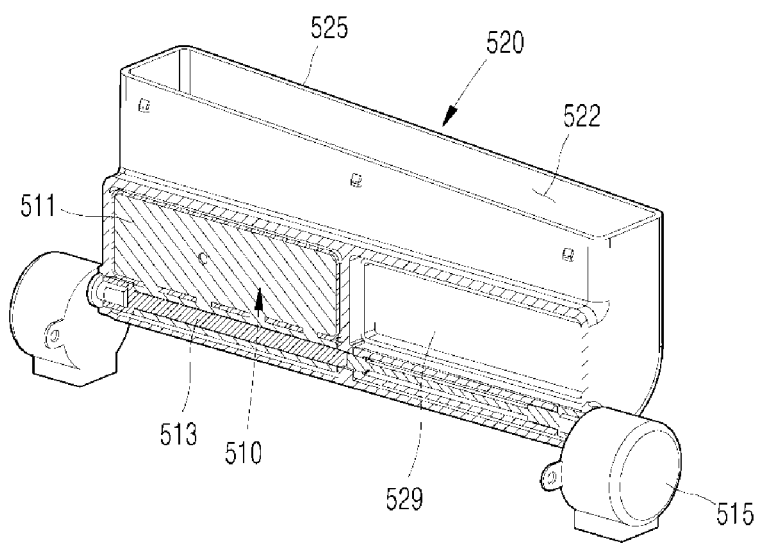
FIG. 36 is a cross-sectional view illustrating an example of a damper that is disposed in the damper housing shown in FIG. 35.
Figure 37:
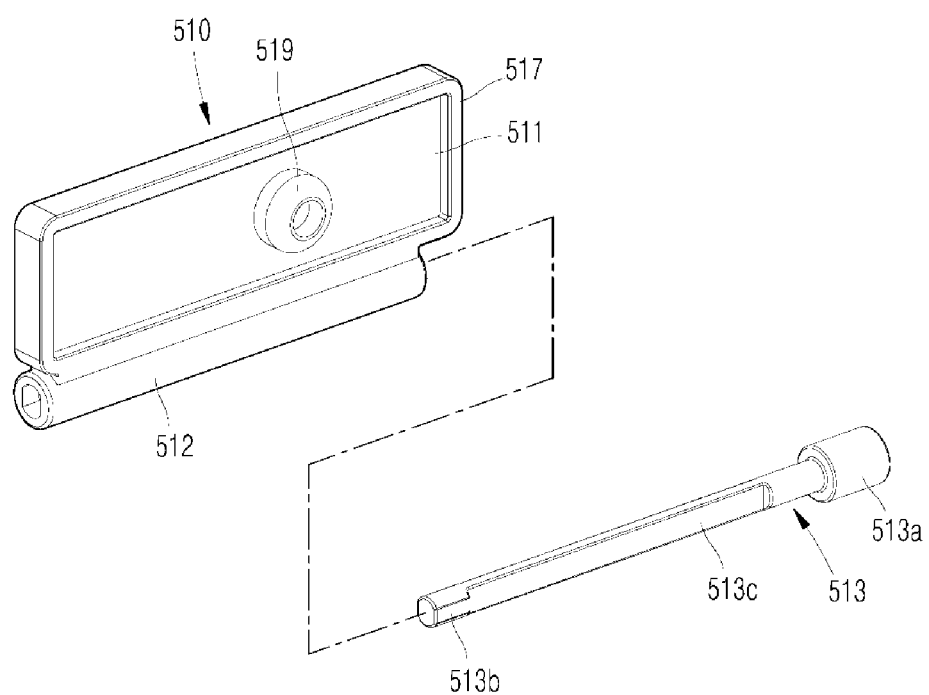
FIG. 37 is an exploded perspective view illustrating the damper in FIG. 35 in more detail.

The drying path hole 529 can be formed in each chamber 15 to discharge the air passing through the dehumidifying material 430 toward the inlet 43, and, as shown in FIG. 36, can be formed in the discharge duct 525 of the damper housing 520 to be opened and closed by the damper 510.

Figure 35:
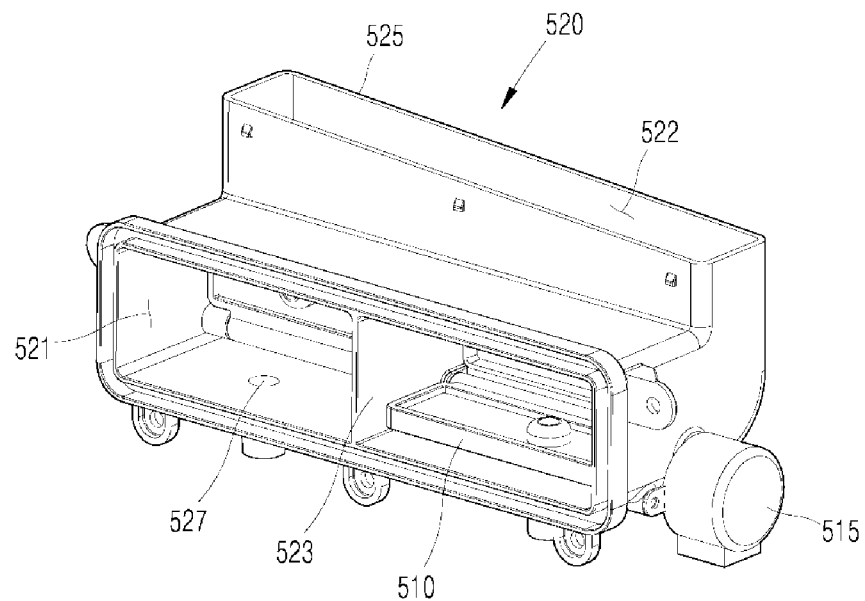
FIG. 35 is a perspective view illustrating the damper housing in FIG. 4A.

The regeneration path hole 527 can be formed in each chamber 15 separately from the drying path hole 529 to discharge the air passing through the dehumidifying material 430 in a direction other than the direction to the inlet 43, and, as shown in FIG. 35, can be formed on the bottom surface of the damper housing 520 to be opened and closed by the damper 510.

The damper 510 can be installed in each chamber 15 to selectively open and close the drying path hole 529 and the regeneration path hole 527, and can be installed in the damper housing 520 as shown in FIG. 35.

In this case, the controller 80 can control the damper 510 to selectively open and close the drying path hole 529 and the regeneration path hole 527 depending on whether or not each heater 710 operates.

As described above, in the shoe care device 1, since the air supplier 10 includes the chamber 15, the heater 710, the drying path hole 529, the regeneration path hole 527, and the damper 510, the controller 80 can control the damper 510 to selectively execute the dehumidifying mode and the regeneration mode.

The condenser 800 can be connected to the regeneration path hole 527 and condense moisture in the air discharged through the regeneration path hole 527, and can constitute a part of the regeneration path F20 so that the condensate water condensed in the condenser 800 can flow through the regeneration path F20.

As described above, in the shoe care device 1, since the air supplier 10 further includes the condenser 800, it can be possible to condense moisture generated during the regeneration process of the dehumidifying material 430.

The shoe care device 1 can further include a steam generator 600 for supplying steam to the accommodation space 41.

That is, since steam can be supplied to the inner cabinet 40 to perform steam treatment on the shoes, it can be possible to exert the effect of sterilization by the high temperature steam and the refreshing effect by inflating the material of the shoes.

Hereinafter, the module including a pair of dehumidifying material 430 (the chamber, the dehumidifying material, the heater, the drying path hole, the regeneration path hole, and the damper) will be described by configuring the same as a drying module A and a drying module B, respectively, in more detail with reference to FIG. 6.

First, the controller 80 can control the shoe care device 1 in a first operation mode in which while one dehumidifying material 430 is heated, the connection path F10 corresponding thereto is closed and the regeneration path F20 thereof is opened, and in which the connection path F10 corresponding to the remaining dehumidifying material 430 is opened and the regeneration path F20 thereof is closed.

In particular, the controller 80 can control the damper 510 such that while one heater 710 is operating, the drying path hole 529 corresponding thereto is closed and the regeneration path hole 527 thereof is opened, and such that the drying path hole 529 corresponding to the remaining heater 710 is opened and the regeneration path hole 527 thereof is closed.

That is, each of the drying module A and the drying module B can be individually operated in a dehumidifying mode or a regeneration mode depending on the opening/closing direction of the damper 510 and whether or not the heaters 710 operate.

As described above, in the case where the damper 510 opens the drying path hole 529 and closes the regeneration path hole 527 so that air is blown into the discharge duct 525, the corresponding drying module can be operated in the dehumidifying mode. In this case, the heater 710 may not be operated.

In some examples, in the case where the damper 510 closes the drying path hole 529 and opens only the regeneration path hole 527 so that air is blown into the regeneration path hole 527, the corresponding module can be operated in the regeneration mode. In this case, the heater 710 needs to be operated to heat the dehumidifying material 430.

Accordingly, the optimization mode of the shoe care device 1 according to the situation will be described by way of example as follows.

First, even if the dehumidifying mode is implemented only in one of the drying module A and the drying module B, moisture can be removed from the air, so control can be performed such that the drying module A is in the dehumidifying mode and the drying module B is in the regeneration mode.

In some examples, the controller 80 can control the damper 510 of the drying module A to open the drying path hole 529 and close the regeneration path hole 527. In addition, the controller 80 can control the damper 510 of the drying module B to close the drying path hole 529 and open only the regeneration path hole 527. In addition, the heater 710 of the drying module B can be controlled to operate.

Accordingly, some of the air inside the inner cabinet 40 can be dehumidified while passing through the drying module A, and the dehumidified air can pass through the damper 510 again to be resupplied into the inner cabinet 40.

At the same time, regeneration of the dehumidifying material 430 can be conducted in the drying module B, and the remaining portion of the air inside the inner cabinet 40 can flow to the condenser 800 together with the moisture separated from the dehumidifying material 430 by passing through the drying module B, and then the moisture can be condensed.

As described above, in the shoe care device 1, since dehumidification is performed through one dehumidifying material 430 among the pair of dehumidifying materials 430, and since the one remaining dehumidifying material 430 is regenerated, the dehumidifying mode and the regeneration mode can be simultaneously performed in the shoe care device 1.

In this case, in the shoe care device 1, the controller 80 can control the first operation mode such that one dehumidifying material 430 and the one remaining dehumidifying material 430 are alternately heated.

In particular, the controller 80 can perform control such that one heater 710 and the remaining heater 710 are alternately operated.

That is, if dehumidification is performed in the drying module A and if regeneration is performed in the drying module B through the above-described process, moisture can be adsorbed onto the dehumidifying material 430 of the drying module A, thereby lowering the dehumidification efficiency over time.

Accordingly, when a predetermined state is established (after a configured time has elapsed or after measurement through a sensor, etc.), control can be performed such that the drying module A is in the regeneration mode and such that the drying module B is in the dehumidifying mode.

That is, the opening and closing directions of the dampers 510 and the operation states of the heaters 710 of the drying module A and the drying module B can be reversely controlled.

Accordingly, some of the air inside the inner cabinet 40 can be dehumidified while passing through the drying module B, and the dehumidified air can pass through the damper 510 again to be resupplied into the inner cabinet 40.

At the same time, regeneration of the dehumidifying material 430 can be conducted in the drying module A, and the remaining portion of the air inside the inner cabinet 40 can flow to the condenser 800 together with the moisture separated from the dehumidifying material 430 by passing through the drying module A, and then the moisture can be condensed.

As described above, since the shoe care device 1 alternately performs dehumidification and regeneration by one of the pair of dehumidifying materials 430 and the remaining one thereof, refreshing of shoes can be performed continuously without interruption in the shoe care device 1.

In the shoe care device 1, the controller 80 can control distribution of air in the first operation mode such that the amount of air blown to the heated dehumidifying material 430 is smaller than the amount of air blown to the unheated dehumidifying material 430.

In particular, the controller 80 can control distribution of air such that the amount of air blown into the chamber 15 in which the heater 710 is operated is smaller than the amount of air blown into the chamber 15 in which the heater 710 is not operated.

That is, the amount of air distributed from the inner cabinet 40 to the drying module A and the drying module B can be controlled to be different from each other. In particular, since a larger amount of air can be supplied in the dehumidifying mode, the amount of air supplied to the drying module in the dehumidifying mode can be controlled to be larger than the amount of air supplied to the drying module in the regeneration mode.

As described above, in the shoe care device 1, since the amount of air blown to any one dehumidifying material 430 that performs dehumidification is larger than the amount of air blown to the one remaining dehumidifying material 430 that is regenerated, it can be possible to help to prevent the dehumidification efficiency from being lowered even during regeneration.

In this case, in the shoe care device 1, the open area of the regeneration path hole 527 can be configured to be smaller than the open area of the drying path hole 529.

That is, even if the amount of distributed air is not separately controlled by the controller 80, as described above, the size of the regeneration path hole 527 can be configured to be relatively small compared to the open area of the drying path hole 529, so that the amount of air supplied to the drying module in the dehumidifying mode can be larger than the amount of air supplied to the drying module in the regeneration mode.

As described above, in the shoe care device 1, since the open area of the regeneration path hole 527 is configured to be smaller than the open area of the drying path hole 529, it can be possible to help to prevent the dehumidification efficiency from being lowered during regeneration even though the amount of distributed air is not separately controlled by the controller 80.

In some examples, more powerful dehumidification can be provided because a large amount of moisture is contained in the shoes accommodated inside the inner cabinet 40.

Accordingly, the controller 80 can control the shoe care device 1 in a second operation mode in which all the connection paths F10 are opened and in which all the regeneration paths F20 are closed in the state in which all of the pair of dehumidifying materials 430 are not heated.

In particular, the controller 80 can control the damper 510 such that all the drying path holes 529 are opened and such that all the regeneration path holes 527 are closed while all the heaters 710 are not operated.

That is, the controller 80 can control the dampers 510 to open the drying path hole 529 and close the regeneration path hole 527 both in the drying module A and in the drying module B.

Accordingly, the air inside the inner cabinet 40 can pass through both the drying module A and the drying module B to be dehumidified. In addition, the dehumidified air can be supplied back to the inner cabinet 40 to refresh the shoes more quickly.

As described above, in the shoe care device 1, since dehumidification can be simultaneously performed through all of the pair of dehumidifying materials 430, the shoe care device 1 can refresh the shoes more quickly.

In some examples, the dehumidifying materials 430 of both the drying module A and the drying module B can deteriorate in the dehumidifying function thereof depending on the long-term use of the dehumidifying materials 430, the external environment, and the like.

Accordingly, the controller 80 can control the shoe care device 1 in a third operation mode in which all the connection paths F10 are closed and in which all the regeneration paths F20 are opened in the state in which all of the pair of dehumidifying materials 430 are heated.

In particular, the controller 80 can control the damper 510 such that all the drying path holes 529 are closed and such that all the regeneration path holes 527 are opened while all the heaters 710 are operated.

That is, the controller 80 can control the dampers 510 such that the drying path holes 529 are closed and such that only the regeneration path holes 527 are opened both in the drying module A and in the drying module B. In addition, the heaters 710 of both the drying module A and the drying module B can be controlled to operate.

Accordingly, regeneration of the dehumidifying material 430 can be performed both in the drying module A and in the drying module B, and if a predetermined state is obtained (after a configured time has elapsed or after measurement through a sensor, etc.), the drying module A and the drying module B can switch to the dehumidifying mode.

As described above, in the shoe care device 1, since regeneration can be simultaneously performed on all of the pair of dehumidifying materials 430, the dehumidifying materials 430 can remain in the state suitable for dehumidification in the shoe care device 1.

The shoe care device 1 can further include a control panel 33 to which an operation signal can be input by a user, and if an operation signal is input to the control panel 33, the controller 80 can perform control such that the third operation mode is conducted for a configured time.

In particular, if an operation signal is input to the control panel 33, the controller 80 can control all the heaters 710 to be operated for a configured time.

In this case, the situation in which an operation signal is input to the control panel 33 can be the case in which the user inputs a command to use the shoe care device 1 after an idle period in which the shoe care device 1 is not operated for a predetermined time.

Accordingly, since the shoe care device 1 regenerates all the dehumidifying materials 430 for a configured time during the initial operation after the idle period, the dehumidifying materials 430 can remain in the state suitable for dehumidification prior to the operation of the shoe care device 1 for refreshing shoes.

In addition, the shoe care device 1 can further include a sensor unit 90 capable of measuring the amount of moisture adsorbed onto the dehumidifying material 430, and the controller 80 can perform control such that the third operation mode is performed until the amount of moisture measured by the sensor unit 90 becomes less than or equal to a configured value.

In particular, the controller 80 can control all the heaters 710 to operate until the amount of moisture measured by the sensor unit 90 becomes less than or equal to a configured value.

In this case, the sensor unit 90 can include a moisture sensor that is installed adjacent to the dehumidifying material 430 and measures the amount of moisture adsorbed onto the dehumidifying material 430 as shown in FIG. 6, and the type and number thereof can be configured in various ways.

As described above, if it is detected that the amount of moisture adsorbed onto the dehumidifying material 430 exceeds a reference value, the shoe care device 1 can regenerate all the dehumidifying materials 430 until the amount of moisture becomes less than or equal to the reference value, thereby maintaining the dehumidifying material 430 in an appropriate state for dehumidification even during the operation of the shoe care device 1 for refreshing shoes.

The shoe care device 1 can be configured to include an inner cabinet 40, an outlet 42, an inlet 43, a connection path F10, a blowing fan 221, a heater 710, and a regeneration path F20.

The connection path F10 is a portion in which air circulates between the outlet 42 and the inlet 43 so that the outlet 42 configures the entrance to the connection path F10 and the inlet 43 configures the exit of the connection path F10.

That is, the connection path F10 can be an air path through which the air is sucked into the air supplier 10 from the inside of the inner cabinet 40, blown to be dehumidified by passing through the dehumidifying material 430, and then supplied back to the inside of the inner cabinet 40.

The blowing fan 221 can be installed on the connection path F10 to blow air from the outlet 42 to the inlet 43. The air can be sucked from the inner cabinet 40 by the operation of the blowing fan 221, and the sucked air can be blown through the connection path F10.

The regeneration path F20 can be a portion through which the air passing through the dehumidifying material 430 is blown to a portion other than the inlet 43 while the dehumidifying material 430 is being heated, and can branch off from the connection path F10 to form a path through which the air passing through the dehumidifying material 430 and/or condensate water flows.

That is, the regeneration path F20 can be a path through which air moves in the process of heating and regenerating the dehumidifying material 430 when the dehumidifying function is not effectively performed due to excessive moisture adsorbed onto the dehumidifying material 430.

Dehumidification of the air is not performed while the dehumidifying material 430 is being regenerated. On the contrary, moisture separated from the dehumidifying material 430 in the regeneration process is contained in the air passing through the dehumidifying material 430, resulting in higher humidity.

Therefore, it is inappropriate to supply air with high humidity back to the inner cabinet 40, so the air can be blown to the regeneration path F20 separated from the connection path F10.

As described above, in the shoe care device 1, the connection path F10 and the regeneration path F20 through which air flows can be provided in the shoe care device 1, and the air passing through the dehumidifying material 430 moves to the regeneration path F20 while the dehumidifying material 430 is being heated, so that the air can flow through the most efficient path depending on the dehumidifying mode and the regeneration mode.

The shoe care device 1 can further include a dehumidifying housing 300 disposed on the connection path F10 and having the dehumidifying material 430 accommodated therein and the heater 710 installed therein.

Specifically, the inner space of the dehumidifying housing 300 can configure a portion of the connection path F10, and the dehumidifying material 430 can be located inside the dehumidifying housing 300. In this case, the heater 710 can be disposed in the connection path F10 to be adjacent to the dehumidifying material 430, thereby heating the dehumidifying material 430.

As described above, since the shoe care device 1 further includes the dehumidifying housing 300 in which the dehumidifying material 430 is accommodated, the dehumidifying material 430 can be stably accommodated to appropriately execute a function thereof.

The shoe care device 1 can further include a suction duct 210 connected between the outlet 42 and the blowing fan 221 to guide the blown air and a blowing duct 230 connected between the blowing fan 221 and the dehumidifying housing 300 to guide the blown air.

Specifically, the suction duct 210 can configure a portion of the connection path F10, and the suction duct 210 can be connected to the outlet 42 to suck air from the inner cabinet 40.

The blowing duct 230 can be connected to one side of the dehumidifying housing 300 accommodating the dehumidifying material 430 so that the air blown through the blowing duct 230 can come into contact with the dehumidifying material 430.

As described above, since the shoe care device 1 further includes the suction duct 210 and the blowing duct 230, the air can stably and effectively flow between the outlet 42 and the dehumidifying housing 300.

The shoe care device 1 can further include a damper housing 520 that is connected between the dehumidifying housing 300 and the inlet 43 to guide the blown air.

Specifically, dry air blown into the damper housing 520 can flow back into the inner cabinet 40 through the inlet 43 to refresh the shoes.

As described above, since the shoe care device 1 further includes the damper housing 520 installed between the dehumidifying housing 300 and the inlet 43, the air can stably and effectively flow between the dehumidifying housing 300 and the inlet 43.

In the shoe care device 1, the damper housing 520 can include a drying path hole 529 formed to discharge the air passing through the dehumidifying material 430 toward the inlet 43 and a regeneration path hole 527 formed to discharge the air passing through the dehumidifying material 430 in a direction other than the direction to the inlet 43.

Specifically, the drying path hole 529 can be formed in the damper housing 520 to discharge the air passing through the dehumidifying material 430 toward the inlet 43, and, as shown in FIG. 36, can be formed in a portion of the discharge duct 525 of the damper housing 520 to be opened and closed by the damper 510.

The regeneration path hole 527 can be formed in the damper housing 520 separately from the drying path hole 529 to discharge the air passing through the dehumidifying material 430 in a direction other than the direction to the inlet 43, and, as shown in FIG. 35, can be formed on the bottom surface of the damper housing 520 to be opened and closed by the damper 510.

As described above, in the shoe care device 1, since the damper housing 520 includes the drying path hole 529 and the regeneration path hole 527, the connection path F10 and regeneration path F20 can be properly separated based on the damper housing 520.

The shoe care device 1 can further include a damper 510 installed on the damper housing 520 to selectively open and close the drying path hole 529 and the regeneration path hole 527.

Specifically, the damper 510 can be installed on the air blowing path to selectively open and close the drying path hole 529 and the regeneration path hole 527, and, as shown in FIG. 35, can be installed in the damper housing 520.

As described above, since the shoe care device 1 further includes the damper 510 installed in the damper housing 520, it can be possible to selectively perform a dehumidifying mode or a regeneration mode by controlling the damper 510.

In this case, the damper 510 can close the drying path hole 529 and open the regeneration path hole 527 when the dehumidifying material 430 is heated. That is, when the dehumidifying material 430 is heat for regeneration thereof, the air passing through the dehumidifying material 430 can be discharged together with the moisture separated from the dehumidifying material 430 through the regeneration path hole 527.

As described above, in the shoe care device 1, when the dehumidifying material 430 is regenerated, the damper 510 can close the drying path hole 529 and open the regeneration path hole 527, so that the moisture separated from the dehumidifying material 430 can be discharged through the regeneration path F20.

The shoe care device 1 can further include a condenser 800 that is connected to the regeneration path hole 527 and condenses moisture in the air discharged through the regeneration path hole 527.

That is, the condenser 800 can be connected to the regeneration path hole 527 to configure a portion of the regeneration path F20, and condensate water condensed in the condenser 800 can flow through the regeneration path F20.

As described above, since the shoe care device 1 further includes the condenser 800 connected to the regeneration path hole 527, the moisture generated during the regeneration process of the dehumidifying material 430 can be condensed.

In the shoe care device 1, the condenser 800 can be disposed at a lower position than the regeneration path hole 527.

That is, since the regeneration path F20 is formed such that the height thereof is gradually reduced from the regeneration path hole 527 to the condenser 800, the condensate water can be smoothly discharged along the slope between the regeneration path hole 527 and the condenser 800.

In the shoe care device 1, the suction duct 210 can include a sump hole 215 that is connected to the condenser 800 and is formed such that the air passing through the condenser 800 is introduced thereinto.

That is, since the air passing through the condenser 800 is reintroduced into the suction duct 210 through the sump hole 215 formed in the suction duct 210, the regeneration path F20 can also have an air circulation structure.

In the shoe care device 1, the sump hole 215 can be disposed at a lower position than the condenser 800.

That is, since the regeneration path F20 is formed such that the height thereof is gradually reduced from the condenser 800 to the sump hole 215, the condensate water can be smoothly discharged along the slope between the condenser 800 and the sump hole 215.

In the shoe care device 1, the suction duct 210 can have a sump 214 formed therein to collect condensate water under the sump hole 215.

That is, since condensate water in the air reintroduced into the suction duct 210 through the sump hole 215 is collected in the sump 214 in the lower portion of the suction duct 210, it can be possible to easily separate the moisture from the air passing through the regeneration path F20 and discharge the same.

In the shoe care device 1, a pair of dehumidifying materials 430 can be disposed to be separate on the branching connection paths F10, and the heater 710 can be installed to heat each of the pair of dehumidifying materials 430.

That is, since a pair of dehumidifying materials 430 is disposed inside the shoe care device 1 and since the connection path F10 and the regeneration path F20 are provided in each dehumidifying material 430, the shoe care device 1 can be operated in an optimal state depending on the situation, thereby further improving the efficiency of processing the shoes.

In this case, the shoe care device 1 can further include a dehumidifying housing 300 that is disposed on the connection path F10 to separately accommodate the respective dehumidifying materials 430 and has heaters 710 installed therein, and a damper housing 520 connected between the dehumidifying housing 300 and the inlet 43 to guide the blown air.

In addition, the damper housing 520 can include a pair of drying path holes 529 formed to discharge the air passing through each dehumidifying material 430 toward the inlet 43 and a pair of regeneration path holes 527 formed to discharge the air passing through each dehumidifying material 430 in a direction other than the direction to the inlet 43.

In addition, the shoe care device 1 can further include a damper 510 installed in the damper housing 520 to selectively open and close the drying path hole 529 and the regeneration path hole 527 corresponding to each dehumidifying material 430.

In addition, the shoe care device 1 can further include a condenser 800 that is connected to the pair of regeneration path holes 527 to condense moisture in the air discharged through the regeneration path holes 527.

The shoe care device 1 can be configure to include an inner cabinet 40, an outlet 42, an inlet 43, and an air supplier 10.

The air supplier 10 can be disposed in the lower portion of the inner cabinet 40 to blow the air in the accommodation space 41, and a connection path F10 through which the air circulates is formed between the outlet 42 and the inlet 43, and a dehumidifying material 430 can be installed on the connection path F10.

In this case, the dehumidifying material 430 can be disposed on the upper end of the air supplier 10 so that the upper surface of the dehumidifying material 430 can be exposed through the bottom of the inner cabinet 40. That is, in the state in which the dehumidifying material 430 is disposed in the upper portion of the machine room 50, the upper surface of the dehumidifying material 430 can be positioned on the bottom of the inner cabinet 40.

Specifically, as described above, since the dry air and steam supplied to the accommodation space 41 of the inner cabinet 40 tend to rise, the machine room 50 can be located in the lower portion of the inner cabinet 40.

In addition, since dehumidification of the air can be performed through the air supplier 10 disposed inside the machine room 50, the dehumidifying material 430 also needs to be disposed inside the machine room 50.

In addition, in the case where the moisture separated from the dehumidifying material 430 is separately discharged through the regeneration path F20 when the dehumidifying material 430 is regenerated, it can be effective for movement of condensate water without a separate pressurization transfer that the moisture moves downwards by its own weight.

In some examples, where the dehumidifying material 430 is disposed in the machine room 50, for condensing efficiency, the dehumidifying material 430 can be disposed in the uppermost portion of the machine room 50.

However, as the process of adsorbing moisture in the air and separating the moisture through regeneration is repeated, the performance of the dehumidifying material 430 can gradually deteriorate, and the dehumidifying material 430 can give off a bad odor, as well as degradation of the performance, due to contamination by foreign substances.

In some examples, where the dehumidifying material 430 is configured to be replaceable, the user can configure the dehumidifying material 430 to be easily replaced without the help of an expert in the process of using the shoe care device 1.

In this case, if the dehumidifying material 430 is simply placed inside the machine room 50, the user needs to open the machine room 50 for replacement of the dehumidifying material 430. However, the machine room 50 has a relatively complicated structure therein, and it can be very difficult for a non-expert user to handle respective configurations inside the machine room 50.

Accordingly, in order for the user to easily replace the dehumidifying material 430 without opening the machine room 50, the dehumidifying material 430 can be replaced through the inner cabinet 40 that has a relatively simple structure therein.

That is, if the upper surface of the dehumidifying material 430 disposed inside the machine room 50 is exposed through the bottom of the inner cabinet 40, the user can easily replace the dehumidifying material 430 without opening the machine room 50.

As described above, in the shoe care device 1, since the dehumidifying material 430 is disposed in the upper portion of the air supplier 10 so that the upper surface of the dehumidifying material 430 is exposed through the bottom of the inner cabinet 40, the function of the dehumidifying material 430 can be effectively executed, and the inspection and replacement of the dehumidifying material 430 can be easy.

In the shoe care device 1, the inner cabinet 40 can include a cabinet bottom plate 45 defining a bottom surface of the accommodation space 41, and the cabinet bottom plate 45 can be opened to correspond to the planar shape of the dehumidifying material 430.

That is, an opening having a size corresponding to the planar shape of the dehumidifying material 430 can be formed in the cabinet bottom plate 45 to solve the problem with an opening that is too large or small to use.

As described above, in the shoe care device 1, since the inner cabinet 40 includes a cabinet bottom plate 45 that is opened to correspond to the planar shape of the dehumidifying material 430, an appropriate opening for inspection and replacement of the dehumidifying material 430 can be formed.

In the shoe care device 1, the dehumidifying material 430 can be installed to be replaceable through the open portion of the cabinet bottom plate 45. That is, the dehumidifying material 430 can be inserted into or drawn out of the machine room 50 through the open portion of the cabinet bottom plate 45.

As described above, in the shoe care device 1, since the dehumidifying material 430 can be replaced through the open portion of the cabinet bottom plate 45, the user can easily replace the dehumidifying material 430 without opening the machine room 50.

In the shoe care device 1, the inner cabinet 40 can further include a dehumidifying material cover 46 installed to open and close the open portion of the cabinet bottom plate 45.

That is, the dehumidifying material cover 46 can configure a portion of the cabinet bottom plate 45, which is the bottom of the inner cabinet 40, and the dehumidifying material cover 46 can be attached to and detached from the cabinet bottom plate 45 of the inner cabinet 40.

As described above, since the shoe care device 1 further includes the dehumidifying material cover 46 installed in the open portion of the cabinet bottom plate 45 of the inner cabinet 40, the dehumidifying material 430 may not be exposed through the bottom of the inner cabinet 40 when the dehumidifying material 430 is not replaced.

In the shoe care device 1, the air supplier 10 can include a dehumidifying housing 300 disposed in the upper portion thereof to accommodate the dehumidifying material 430, and the dehumidifying material cover 46 can be coupled to the upper surface of the dehumidifying housing 300.

That is, when the dehumidifying material cover 46 is removed from the cabinet bottom plate 45, the dehumidifying housing 300 positioned below the same can be exposed so that the dehumidifying material 430 can be placed inside or separated from the dehumidifying housing 300.

As described above, since the shoe care device 1 includes the dehumidifying housing 300 and since the dehumidifying material cover 46 can be coupled to the upper surface of the dehumidifying housing 300, the dehumidifying material 430 can be stably accommodated to properly implement its function.

In the shoe care device 1, the transverse cross-sectional area of the dehumidifying housing 300 can be greater than the longitudinal cross-sectional area thereof.

In order to minimize interference of the dehumidifying material 430 and the dehumidifying housing 300 for accommodating the same with other elements inside the machine room 50, the dehumidifying material 430 and the dehumidifying housing 300 for accommodating the same can be widely disposed in the transverse direction in the uppermost portion of the machine room 50.

If the dehumidifying housing 300 is disposed long in the longitudinal direction, the remaining elements inside the machine room 50 can be disposed to avoid the dehumidifying housing 300, which can make the structure thereof more complicated and undesirable.

As described above, in the shoe care device 1, since the dehumidifying housing 300 is widely disposed in the transverse direction, it can be possible to minimize interference between the dehumidifying housing 300 and other elements inside the machine room 50.

In the shoe care device 1, the air supplier 10 can have a regeneration path F20, further including a heater 710 installed in the dehumidifying housing 300 to heat the dehumidifying material 430, through which the air passing through the dehumidifying material 430 is blown to a portion other than the inlet 43 while the dehumidifying material 430 is being heated.

As described above, since the air has relatively high humidity while the dehumidifying material 430 is being regenerated, the air can be blown to the regeneration path F20 separated from the connection path F10, instead of being supplied back to the inner cabinet 40.

As described above, since the shoe care device 1 can heat the dehumidifying material 430 using the heater 710 and since the regeneration path F20 through which air flows according thereto can be provided, it can be possible to help to prevent the air from moving into the inner cabinet 40 in the regeneration mode.

In the shoe care device 1, a pair of dehumidifying materials 430 can be disposed to be separate on the branching connection paths F10.

In this case, the air supplier 10 can have a regeneration path F20, including a dehumidifying housing 300 disposed in the upper portion to separately accommodate the respective dehumidifying materials 430 and heater 710 installed in the dehumidifying housing 300 to heat each of the pair of dehumidifying materials 430, through which the air passing through the dehumidifying material 430 is blown to a portion other than the inlet 43 while the dehumidifying material 430 is being heated.

The shoe care device 1 can be configured to include an inner cabinet 40, an outlet 42, an inlet 43, a connection path F10, a blowing fan 221, and a dehumidifying material 430.

In this case, the outlet 42 and the inlet 43 can be disposed so as not to face each other on the inner plane of the inner cabinet 40.

Specifically, in consideration of only the air circulation efficiency, it can be advantageous that the outlet 42 and the inlet 43 formed on the bottom surface of the inner cabinet 40 are disposed side by side on a plane.

Accordingly, in the case of a clothing care device that mainly processes clothes, an inlet and an outlet can be disposed side by side on a plane.

However, in the case of the shoe care device 1 that mainly processes shoes, since the inner space of the inner cabinet 40 is smaller than that of the clothing care device, the outlet 42 and the inlet 43 may not be disposed side by side on a plane.

In some cases, considering the dehumidifying efficiency by the dehumidifying material 430 in the shoe care device 1, it can be disadvantageous that the outlet 42 and the inlet 43 are disposed side by side on a plane.

In this regard, in order to improve the dehumidifying efficiency by the dehumidifying material 430, the shoe care device can allow the moisture-containing air to contact and collide with the dehumidifying material 430 on the longest possible path.

Therefore, the dehumidifying material 430 needs to be formed as thin as possible to maximize the cross-sectional area and minimize path resistance thereof. In some examples, the dehumidifying material 430 can have an elongated shape extending along the movement path of air.

In some examples, a long dehumidifying material 430 can be disposed in a shape capable of connecting the housing inlet 311 formed on one side of the dehumidifying housing 300 and the housing outlet 331 formed on the opposite side thereof.

In this case, if the outlet 42 and the inlet 43 are disposed side by side on a plane, and if the dehumidifying material 430 is disposed in the longitudinal direction to connect the outlet 42 and the inlet 43, the length of the dehumidifying material 430 can become smaller, thereby lowering the dehumidifying efficiency.

As described above, in the shoe care device 1, since the outlet 42 and the inlet 43 are disposed so as not to face each other on the inner plane of the inner cabinet 40, the dehumidifying efficiency of the dehumidifying material 430 can be further improved.

In the shoe care device 1, the dehumidifying material 430 can be disposed in a shape extending along the first direction X on the plane of the dehumidifying housing 300, and the air can be blown in the first direction X on the connection path F10.

As described above, for dehumidifying efficiency, the air can come into contact and collide with the dehumidifying material 430 on the longest possible path. Accordingly, in some examples, the air can be blown along the extended longitudinal direction of the dehumidifying material 430.

As described above, in the shoe care device 1, since the dehumidifying material 430 is disposed to extend in one direction and since the air is blown along the extension direction of the dehumidifying material 430, the air can come into contact and collide with the dehumidifying material 430 on the longest possible path.

In the shoe care device 1, any one of the outlet 42 and the inlet 43 can be disposed at one end of the dehumidifying material 430 in the first direction X, and the remaining one of the outlet 42 and the inlet 43 can be disposed on the side of the dehumidifying material 430 in the first direction X.

If the outlet 42 and the inlet 43 are disposed side by side on a plane and if the dehumidifying material 430 is disposed in the longitudinal direction parallel to the connection direction of the outlet 42 and the inlet 43, the air blowing path can become relatively complicated, thereby reducing the dehumidification efficiency as well.

That is, in this case, the suction duct 210 and the discharge duct 525 are disposed at one end and the opposite end of the dehumidifying material 430, so the blowing duct 230 may not be disposed to be connected to one end of the dehumidifying material 430.

In particular, the arrangement of the machine room 50 may be difficult because the arrangement of the damper housing 520 can be difficult and because the structure can become complicated.

As described above, in the shoe care device 1, since the outlet 42 is disposed on any one of the one end and the side of the dehumidifying material 430 and since the inlet 43 is disposed on the remaining one thereof, it can be possible to relatively simplify the air blowing path and enable appropriate arrangement of the machine room 50 according thereto.

In the shoe care device 1, the inlet 43 can be disposed at the rear end of the dehumidifying material 430 in the first direction X, and the outlet 42 can be disposed on the side of the dehumidifying material 430 in the first direction X.

As described above, in the case where any one of the outlet 42 and the inlet 43 is to be disposed at one end of the dehumidifying material 430 in the first direction X and where the remaining one of the outlet 42 and the inlet 43 is to be disposed on the side of the dehumidifying material 430 in the first direction X, the inlet 43 can be disposed at the rear end of the dehumidifying material 430 in the first direction X in consideration of air circulation efficiency.

The circulated air can flow smoothly only if the air passing through the dehumidifying material 430 quickly flows into the inner cabinet 40.

Therefore, the inlet 43 can be disposed at the rear end of the dehumidifying material 430, so that the air passing through the dehumidifying material 430 can quickly flow into the inner cabinet 40 when blowing air along the extended longitudinal direction of the dehumidifying material 430.

As described above, in the shoe care device 1, since the inlet 43 is disposed at the rear end of the dehumidifying material 430 and since the outlet 42 is disposed on the side of the dehumidifying material 430, the discharge pressure of air can be appropriately maintained in the inlet 43.

In the shoe care device 1, the first direction X can indicate the direction in which both sides of the inner cabinet 40 are connected, and the outlet 42 can be disposed on the side of the dehumidifying material 430 corresponding to the front portion of the inner cabinet 40.

That is, as shown in FIGS. 3A and 3B, the outlet 42 can be disposed on the front portion of the inner cabinet 40.

In the process of using the shoe care device 1, condensate water can also be generated inside the inner cabinet 40, and this condensate water can flow down along the inner surfaces of the inner cabinet 40 to gather on the bottom surface of the inner cabinet 40.

If the condensate water gathered above can leak to the outside of the inner cabinet 40, the user can feel inconvenience, causing problems in usability.

In particular, since the door 30 is installed in the front portion of the inner cabinet 40, the shoe case device can be configured to help to prevent leakage of condensate water through the gap of the door 30.

Accordingly, in the shoe care device 1, since the outlet 42 is disposed in the front portion of the inner cabinet 40, the condensate water condensed inside the inner cabinet 40 can be discharged through the outlet 42, instead of leaking to the outside.

In the shoe care device 1, a pair of dehumidifying materials 430 can be disposed on the connection path F10, and the dehumidifying housing 300 can accommodate the pair of dehumidifying materials 430 to be separated from each other and to respectively extend along the first direction X.

In this case, the shoe care device 1 can further include a damper housing 520 connected between the dehumidifying housing 300 and the inlet 43 to guide the blown air, and the damper housing 520 can have a pair of drying path holes 529 each formed to discharge the air passing through each dehumidifying material 430 to the inlet 43.

In addition, the inlet 43 can be connected to the pair of drying path holes 529 to supply the blown air to the accommodation space 41.

The shoe care device 1 can be configured to include an inner cabinet 40, an outlet 42, an inlet 43, a connection path F10, a blowing fan 221, a dehumidifying material 430, and a dehumidifying housing 300.

In this case, the dehumidifying material 430 can be disposed to extend along the first direction X on the plane of the dehumidifying housing 300, and air can be blown in the first direction X on the connection path F10.

Specifically, the dehumidifying material 430 can be accommodated in the dehumidifying housing 300. That is, the dehumidifying housing 300 can be installed in the upper portion of the machine room 50, and the dehumidifying material 430 can be accommodated in the dehumidifying housing 300, thereby executing dehumidification and regeneration functions.

In particular, as described above, in order to optimize the disposition of the dehumidifying material 430, the dehumidifying housing 300 can also be located at the bottom of the inner cabinet 40. In addition, the dehumidifying material cover 46 can be coupled to the upper surface of the dehumidifying housing 300 to cover the dehumidifying material 430.

In some implementations, a portion of the dehumidifying housing 300, in which the dehumidifying material 430 is accommodated, can be widely disposed in the transverse direction in the uppermost portion of the machine room 50.

One side of the dehumidifying housing 300 accommodating the dehumidifying material 430 can be connected to the blowing duct 230 to supply air toward the dehumidifying material 430.

In addition, the air supplied to the inside of the dehumidifying housing 300 can come into contact with the dehumidifying material 430, and can then be blown toward the connection path F10 or the regeneration path F20. In some examples, the opposite side of the dehumidifying housing 300 can be connected to the damper housing 520 so that the air passing through the inside can be blown toward the damper housing 520.

In some implementations, for dehumidifying efficiency, the air can come into contact and collide with the dehumidifying material 430 on the longest possible path. Accordingly, the air can be blown along the extended longitudinal direction of the dehumidifying material 430.

In some implementations, the dehumidifying material 430 can be accommodated in the dehumidifying housing 300 so as to extend along one direction on the plane, and the air can be blown in the extension direction of the dehumidifying material 430, so the dehumidifying material 430 can be stably accommodated to properly implement the function thereof.

In some implementations, the dehumidifying housing 300 can include a housing inlet 311, formed at the rear in the first direction X, to which the blowing duct 230 is coupled and a housing outlet 331, formed at the front in the first direction X, to which the damper housing 520 is coupled.

In order to allow the air passing through the interior of the dehumidifying housing 300 to further come into contact and collide with the dehumidifying material 430, the air movement path inside the dehumidifying housing 300 can be maximized.

Accordingly, the housing inlet 311 and the housing outlet 331 can be disposed on opposite sides on the plane of the dehumidifying housing 300.

As described above, in the shoe care device 1, since the dehumidifying housing 300 includes the housing inlet 311 and the housing outlet 331, the air can stably and effectively pass through the interior of the dehumidifying housing 300 accommodating the dehumidifying material 430.

In the shoe care device 1, the dehumidifying housing 300 can further include a housing bottom plate 310 configuring a bottom surface, a rear dehumidifying material wall 320 configuring a rear surface in the first direction X, a front dehumidifying material wall 330 configuring a front surface in the first direction X, and left dehumidifying material walls 340a and 340b and right dehumidifying material walls 350a and 350b configuring side surfaces connected between the rear dehumidifying material wall 320 and the front dehumidifying material wall 330.

The rear dehumidifying material wall 320, the front dehumidifying material wall 330, the left dehumidifying material walls 340a and 340b, and the right dehumidifying material walls 350a and 350b can configure wall surfaces erected in the vertical direction, respectively. Based on the first direction X, the rear dehumidifying material wall 320 can configure a rear wall surface, the front dehumidifying material wall 330 can configure a front wall surface, the left dehumidifying material walls 340a and 340b can configure left wall surfaces, and the right dehumidifying material walls 350a and 350b can configure right wall surfaces in the dehumidifying housing 300.

As described above, in the shoe care device 1, since the dehumidifying housing 300 further includes the housing bottom plate 310, the rear dehumidifying material wall 320, the front dehumidifying material wall 330, the left dehumidifying material walls 340a and 340b, and the right dehumidifying material walls 350a and 350b, a space for accommodating the dehumidifying material 430 can be stably partitioned.

In the shoe care device 1, the dehumidifying housing 300 can be disposed such that the upper surface thereof is positioned at the bottom of the inner cabinet 40.

In this case, the dehumidifying material cover 46 can be coupled to the upper surface of the dehumidifying housing 300.

As described above, in the shoe care device 1, since the upper surface of the dehumidifying housing 300 is positioned at the bottom of the inner cabinet 40, the function of the dehumidifying material 430 can be effectively executed, and it is easy to check and replace the dehumidifying material 430.

In the shoe care device 1, the housing inlet 311 can be formed on the housing bottom plate 310, and the housing outlet 331 can be formed on the front dehumidifying material wall 330.

Since the dehumidifying material 430 and the dehumidifying housing 300 are disposed at the uppermost portion of the machine room 50, a connection of the blowing duct 230 to the dehumidifying housing 300 can facilitate blowing and minimize interference between members.

Accordingly, the housing inlet 311 can be formed on the lower surface of one side of the dehumidifying housing 300.

In some case where the air passing through the dehumidifying housing 300 is immediately introduced into the inner cabinet 40, it may be impossible to selectively blow the air to the connection path F10 or the regeneration path F20, so the housing outlet 331 can be formed on the side surface of the dehumidifying housing 300, instead of on the upper surface thereof.

Accordingly, the housing outlet 331 can be formed on the side surface opposite the portion where the housing inlet 311 is formed on the plane.

As described above, in the shoe care device 1, since the housing inlet 311 is formed on the housing bottom plate 310 and since the housing outlet 331 is formed on the front dehumidifying material wall 330, it can be possible to effectively blow the air and minimize interference between members.

In the shoe care device 1, the dehumidifying housing 300 can further include an inlet connector 390, formed on one side of the upper surface, to which the outlet 42 is coupled.

In this case, the inlet connector 390 can be a medium member to enable the outlet 42 to be coupled to one surface thereof and the discharge duct 525 to be coupled to the opposite surface thereof.

The dehumidifying housing 300 can be made of a synthetic resin material capable of injection molding, and the dehumidifying housing 300 can be made to be combined with the inlet connector 390 when taking into consideration that the outlet 42 is also disposed at the bottom of the inner cabinet 40.

As described above, in the shoe care device 1, since the dehumidifying housing 300 further includes the inlet connector 390, the upper structure of the machine room 50 can be simplified, thereby facilitating assembly and providing an advantage in productivity.

In the shoe care device 1, the heater 710 can include a fixed end 712 installed on the housing bottom plate 310 and a free end 711 that extends along the first direction X from the fixed end 712.

In this case, the fixed end 712 can be electrically connected to a power source, and the free end 711 can generate heat while electric energy is supplied to the free end 711 through the fixed end 712.

As described above, in the shoe care device 1, since the heater 710 includes the fixed end 712 and the free end 711, the heater 710 can be effectively installed in the dehumidifying housing 300.

In some examples, in order to prevent the dehumidifying housing 300 from being thermally deformed or damaged by the heater 710, a separate heat insulating member can be disposed at a portion where the heater 710 is disposed.

In addition, in the case where a pair of dehumidifying materials 430 is disposed on the connection path F10, a pair of left dehumidifying material walls 340a and 340b and a pair of right dehumidifying material walls 350a and 350b can be formed, in which any one dehumidifying material 430 can be accommodated between a first left dehumidifying material wall 340a and a first right dehumidifying material wall 350a and in which the remaining dehumidifying material 430 can be accommodated between a second left dehumidifying material wall 340b and a second right dehumidifying material wall 350b.

In this case, the shoe care device 1 can further include heaters 710 that are respectively installed between the first left dehumidifying material wall 340a and the first right dehumidifying material wall 350a and between the second left dehumidifying material wall 340b and the second right dehumidifying material wall 350b to heat the pair of dehumidifying material 430, respectively.

The shoe care device 1 can be configured to include an inner cabinet 40, an outlet 42, an inlet 43, a connection path F10, a blowing fan 221, a dehumidifying material 430, a heater 710, a regeneration path F20, and a damper housing 520.

As described above, the shoe care device 1 can guide the air passing through the dehumidifying material 430 to the connection path F10 or the regeneration path F20 in the damper housing 520, so the air can stably and effectively move through each of the connection path F10 and the regeneration path F20.

The shoe care device 1 can further include a dehumidifying housing 300 disposed on the connection path F10 to accommodate the dehumidifying material 430 and having the heater 710 installed therein, and the damper housing 520 can be connected between the dehumidifying housing 300 and the inlet 43.

In particular, the damper housing 520 can be coupled to the front of the dehumidifying housing 300 in the first direction X.

Specifically, the damper housing 520 can be coupled to a housing outlet 331 formed in the dehumidifying housing 300 so that air passing through the dehumidifying material 430 can be blown to the damper housing 520. In addition, the air can be blown to the connection path F10 or the regeneration path F20 depending on the opening/closing direction of the damper 510 installed in the damper housing 520.

In this case, since the housing outlet 331 is formed on the side surface of the dehumidifying housing 300 as described above, one side surface of the damper housing 520 coupled with the housing outlet 331 can be configured to be open.

In addition, in the case where the air introduced into the damper housing 520 flows through the connection path F10, the air may be blown into the inner cabinet 40 through the discharge duct 525 and the inlet 43, so the opposite side of the damper housing 520 can be connected to the inlet 43 (or the discharge duct 525).

As described above, since the shoe care device 1 further includes the dehumidifying housing 300 in which the dehumidifying material 430 is accommodated, the dehumidifying material 430 can be stably accommodated to appropriately implement the function thereof.

In the shoe care device 1, the damper housing 520 can further include a damper entrance 521, formed at the rear in the first direction X, to which the dehumidifying housing 300 is coupled and a damper exit 522 formed at the front in the first direction X to be connected to the inlet 43.

That is, the damper entrance 521 can be connected to the housing outlet 331, and the damper exit 522 can be connected to the inlet 43 (or the discharge duct 525).

As described above, in the shoe care device 1, since the damper housing 520 further includes the damper entrance 521 and the damper exit 522, the air can stably and effectively pass through the space between the dehumidifying housing 300 and the inlet 43.

In the shoe care device 1, the drying path hole 529 can be formed in the longitudinal cross-section of the damper housing 520 between the damper entrance 521 and the damper exit 522, and the regeneration path hole 527 can be formed on the bottom surface of the damper housing 520 between the damper entrance 521 and the damper exit 522.

As described above, since the inlet 43 is disposed at the bottom of the inner cabinet 40, the discharge duct 525 connected to the inlet 43 can be installed to be open along the longitudinal direction. Accordingly, the damper exit 522 connected to the discharge duct 525 can be formed to be open on the side or upper surface thereof.

Accordingly, the drying path hole 529 formed between the damper entrance 521 and the damper exit 522 can be defined in the longitudinal cross-section of the damper housing 520.

In addition, in the case where the air introduced into the damper housing 520 flows through the regeneration path F20, the air may be blown to the condenser 800 through the regeneration path hole 527, so the regeneration path hole 527 can be connected between the damper entrance 521 and the damper exit 522.

In some examples, the path from the regeneration path hole 527 to the sump hole 215, which are disposed on the regeneration path F20, can be inclined such that the height thereof is reduced along the path for the effective drainage of condensate water, so the regeneration path hole 527 can be defined on the bottom surface of the damper housing 520.

As described above, in the shoe care device 1, since the drying path hole 529 is formed on the longitudinal cross-section of the damper housing 520 and since the regeneration path hole 527 is formed on the bottom surface of the damper housing 520, condensate water can be effectively discharged through the regeneration path.

In some examples, the damper housing 520 can be made of a synthetic resin material capable of injection molding, and in some cases, the damper housing 520 can be manufactured to be combined with at least one of the discharge duct 525 and the regeneration path hole 527.

In the shoe care device 1, the damper 510 can rotate about the hinge shaft 512 to selectively open and close the longitudinal cross-section and the bottom surface of the damper housing 520.

As described above, one side surface of the damper housing 520 can be opened and coupled with the housing outlet 331 of the dehumidifying housing 300, and the opposite side surface or top surface can be opened and coupled with the discharge duct 525, and the regeneration path hole 527 can be connected to the bottom surface thereof.

Accordingly, the damper 510 for selectively opening and closing the discharge duct 525 and the regeneration path hole 527 can be disposed between the opposite side and the bottom surface of the damper housing 520.

Accordingly, in the case where the damper 510 is installed to be hinge-rotatable around one end thereof, the degree of opening the discharge duct 525 can be adjusted according to the standing angle with respect to the bottom surface of the damper housing 520.

That is, in the case where the damper 510 hinge-rotates to be parallel to the bottom surface of the damper housing 520, the discharge duct 525 can be maximally opened so that air can be smoothly blown through the connection path F10.

In this case, in the case where the damper 510 covers the bottom surface of the damper housing 520, the discharge duct 525 can be maximally opened, and at the same time, the regeneration path hole 527 formed on the bottom surface of the damper housing 520 can be closed.

In some examples, when the damper 510 hinge-rotates to be perpendicular to the bottom surface of the damper housing 520, the discharge duct 525 can be closed.

In this case, since the damper 510 does not cover the bottom surface of the damper housing 520, the regeneration path hole 527 can be opened so that air can be blown along the regeneration path F20.

As described above, in the shoe care device 1, since the damper 510 rotates around the hinge shaft 512 to selectively open and close the connection path F10 and the regeneration path F20, the connection path F10 and the regeneration path F20 can be easily opened and closed while further simplifying the structure of the damper 510.

In some examples, in the case where a pair of dehumidifying materials 430 is disposed on the connection path F10, the damper housing 520 can further include a damper separation wall 523 for separating the air passing through the respective dehumidifying materials 430, and the drying path hole 529 and the regeneration path hole 527 can be respectively formed on both sides of the damper separation wall 523.

The shoe care device 1 can be configured to include an inner cabinet 40, an outlet 42, an inlet 43, a connection path F10, a blowing fan 221, a dehumidifying material 430, a heater 710, a regeneration path F20, a damper housing 520, and a damper 510.

As described above, in the shoe care device 1, since the damper 510 installed in the damper housing 520 selectively opens and closes the connection path F10 and the regeneration path F20, selective opening and closing of the connection path F10 and the regeneration path F20 can be stably and effectively performed.

In the shoe care device 1, the damper 510 can include an opening/closing plate 511 that is hinge-rotatable about a hinge shaft 512 formed on one side, a shaft 513 coupled to the hinge shaft 512 of the opening/closing plate 511 to transmit rotational force, and an actuator 515 coupled to the shaft 513 to provide rotational force.

Specifically, the damper 510 can include an opening/closing plate 511 in the shape of a plate protruding in one direction from the hinge shaft 512. The opening/closing plate 511 can be configured to correspond to the shape of the drying path hole 529 formed in the damper housing 520, and when the damper 510 hinge-rotates, the opening/closing plate 511 can cover the drying path hole 529.

A shaft 513 can be coupled to the hinge shaft 512 of the damper 510. Specifically, a fastening hole can be formed in a portion of the hinge shaft 512, and a fastening portion 513*b* of the shaft 513 can be engaged with the fastening hole.

Accordingly, when the shaft 513 rotates, the fastening portion 513b can press the fastening hole so that the hinge shaft 512 of the damper 510 can rotate. The shaft 513 can be coupled to an actuator 515 to transfer the rotational force supplied from the actuator 515 to the hinge shaft 512 of the damper 510.

As described above, in the shoe care device 1, since the damper 510 includes the opening/closing plate 511, the shaft 513, and the actuator 515, the damper 510 can be precisely and effectively controlled through an electrical signal.

In the shoe care device 1, the open area of the regeneration path hole 527 can be configured to be smaller than the open area of the drying path hole 529, and the opening/closing plate 511 can be configured to have a planar shape correspond to the open area of the drying path hole 529.

As described above, since the regeneration path hole 527 can be smaller than the drying path hole 529, the opening/closing plate 511, which is configured to correspond to the shape of the drying path hole 529, can hinge-rotate, thereby covering the regeneration path hole 527.

As described above, in the shoe care device 1, since the opening/closing plate 511 is configured to correspond to the open area of the drying path hole 529, it can be possible to respectively close the connection path F10 and the regeneration path F20 using one opening/closing plate 511.

In particular, as described above, in the case where the drying path hole 529 is formed on the longitudinal cross-section of the damper housing 520 and where the regeneration path hole 527 is formed on the bottom surface of the damper housing 520, the opening/closing plate 511 can rotate about the hinge shaft 512 so that one side thereof can cover the drying path hole 529 and so that the opposite side thereof can cover the regeneration path hole 527.

In the shoe care device 1, the damper 510 can further include a first sealing member 517 made of an elastic material, which is continuously installed along the edge of one surface of the opening/closing plate 511, and a second sealing member 519 made of an elastic material, which is installed to correspond to the open area of the drying path hole 529 on the opposite surface of the opening/closing plate 511.

That is, the first sealing member 517 can be formed along the edge of the opening/closing plate 511, and the first sealing member 517 can be made of an elastic material, thereby improving sealing force when the opening/closing plate 511 covers the drying path hole 529.

In some examples, as described above, since the regeneration path hole 527 is formed smaller than the drying path hole 529, the entire area of the opening/closing plate 511 in a plate-like structure may not evenly seal the regeneration path hole 527.

Accordingly, the second sealing member 519 can be formed in a portion of the opening/closing plate 511, which corresponds to the position of the regeneration path hole 527. The second sealing member 519 can also be made of an elastic material to improve sealing force when the opening/closing plate 511 covers the regeneration path hole 527.

As described above, in the shoe care device 1, since the damper 510 further includes the first sealing member 517 and the second sealing member 519, it can be possible to further improve sealing force when closing the connection path F10 and the regeneration path F20.

In the shoe care device 1, at least one of the first sealing member 517 and the second sealing member 519 can be formed with the opening/closing plate 511 by insert molding.

Insert molding is a method of inserting two or more different materials together into a mold for injection. The opening/closing plate 511 can be made of an injection-molded synthetic resin material, and at least one of the first sealing member 517 and the second sealing member 519 can be made of an elastic material such as rubber, fiber, or the like.

As described above, in the shoe care device 1, since the damper 510 is made by insert molding, the damper 510 can be easily and effectively manufactured.

In the shoe care device 1, the shaft 513 can include an actuator coupling portion 513a formed at one end thereof in the axial direction and coupled to the actuator 515, a fastening portion 513b formed at the opposite end thereof in the axial direction and coupled to the hinge shaft 512 of the opening/closing plate 511 so as to transfer rotational force thereto, and a deformable portion 513c connected between the actuator coupling portion 513a and the fastening portion 513b so as not to transfer rotational force to the hinge shaft 512 of the opening/closing plate 511.

In some examples, only the fastening portion 513b of the shaft 513 can be fastened to engage with the fastening hole of the damper 510, so that only the fastening portion 513b can be constrained by the rotation of the damper 510, and the remaining portions may not be constrained by the rotation of the hinge shaft 512.

That is, the deformable portion 513c of the shaft 513 can be coupled to the hinge shaft 512 so as not to engage therewith, which enables idle rotation in a certain portion even when the hinge shaft 512 rotates.

As described above, in the shoe care device 1, since the shaft 513 includes the actuator coupling portion 513a, the fastening portion 513b, and the deformable portion 513c, the rotational force of the actuator 515 can be efficiently transferred to the opening/closing plate 511.

The deformable portion 513c can be made of a material capable of elastic deformation against torsion.

Specifically, the shaft 513 can be made of a material that is elastically deformable to a certain extent, such as a synthetic resin material. Accordingly, even in the state in which the opening/closing plate 511 of the damper 510 can no longer rotate inside the damper housing 520, the deformable portion 513c of the shaft 513 can be twisted and deformed to a certain extent.

According to this, the rotational force supplied from the actuator 515 can be further applied to the shaft 513 even when the rotation of the opening/closing plate 511 is stopped, so that the deformable portion 513c can be twisted to further pressurize the opening/closing plate 511.

Therefore, even if the rotational force supplied from the actuator 515 is shut off in the state in which the opening/closing plate 511 of the damper 510 covers the drying path hole 529 or the regeneration path hole 527, the opening/closing plate 511 can remain in close contact with the drying path hole 529 or the regeneration path hole 527 by the pressure caused by the torsion of the deformable portion 513c.

If a gap is formed between the opening/closing plate 511 and the drying path hole 529 or the regeneration path hole 527 due to reaction or the like when the supply of the rotational force from the actuator 515 is shut off, air can flow in unintended directions through the gap.

In particular, in order to block moisture or odor generated during the regeneration process of the dehumidifying material 430 from flowing into the inner cabinet 40, sealing force can be increased through the structure of the damper 510 and the shaft 513 described above.

As described above, in the shoe care device 1, since the deformable portion 513c made of an elastic material is twistable and deformable, it can be possible to maintain the contact force with the drying path hole 529 or the regeneration path hole 527 to a certain extent even in the state in which the operation of the actuator 515 is stopped.

Figure 38:
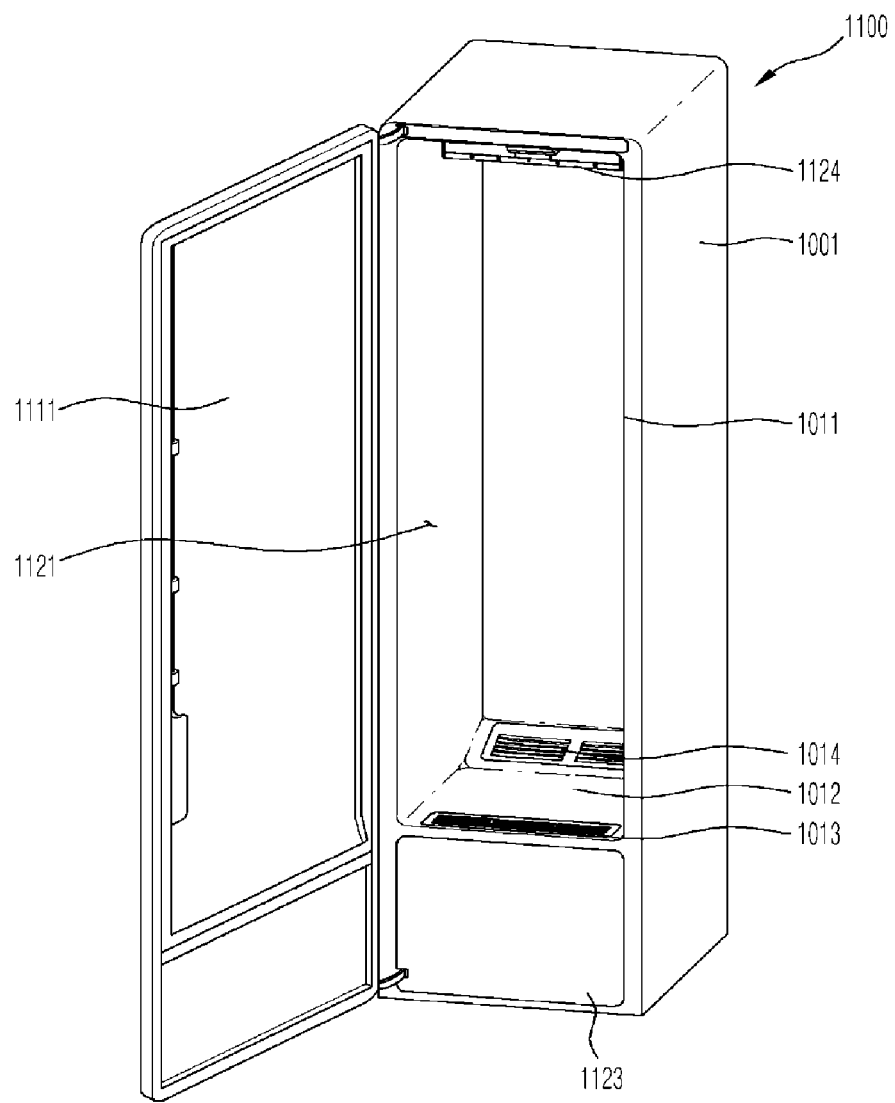
FIG. 38 illustrates an example of a drying apparatus.

As shown in FIG. 38, the drying apparatus 1100 can be configured to include a cabinet 1001 having a first chamber 1121 (a drying chamber) and a second chamber 1122 (a device chamber) (see FIG. 39) that are separated by a partition 1012.

The first chamber 1121 can be configured to communicate with the outside of the cabinet 1001 through an opening 1011 (a first chamber opening) provided on the front surface of the cabinet 1001, and the second chamber 1122 can be configured to communicate with the outside of the cabinet through a second chamber opening formed on the front surface of the cabinet.

The second chamber opening can be configured to be opened and closed by a chamber door 123 detachably coupled to the cabinet 1001, and the opening 1011 can be configured to be opened and closed by a door 1111 rotatably coupled to the cabinet 1001.

The first chamber 1121 can be equipped with a support 1124 on which a drying object (clothes, etc.) is mounted, and FIG. 38 shows an example in which the support 1124 is configured as a bar on which a hanger is supported. The support 1124 can be provided on any one of an upper surface, both side surfaces, and a rear surface of the first chamber 1121, and FIG. 38 shows an example in which the support 1124 is provided on the upper surface of the first chamber 1121.

The partition 1012 can be provided to configure a bottom surface of the first chamber (an upper surface of the second chamber), and the partition 1012 can have a discharge hole 1013 and a supply hole 1014 provided therein. The discharge hole 1013 can be a means for discharging air from the first chamber 1121 to the second chamber 1122, and the supply hole 1014 can be a means for supplying air to the first chamber 1121.

Figure 39:
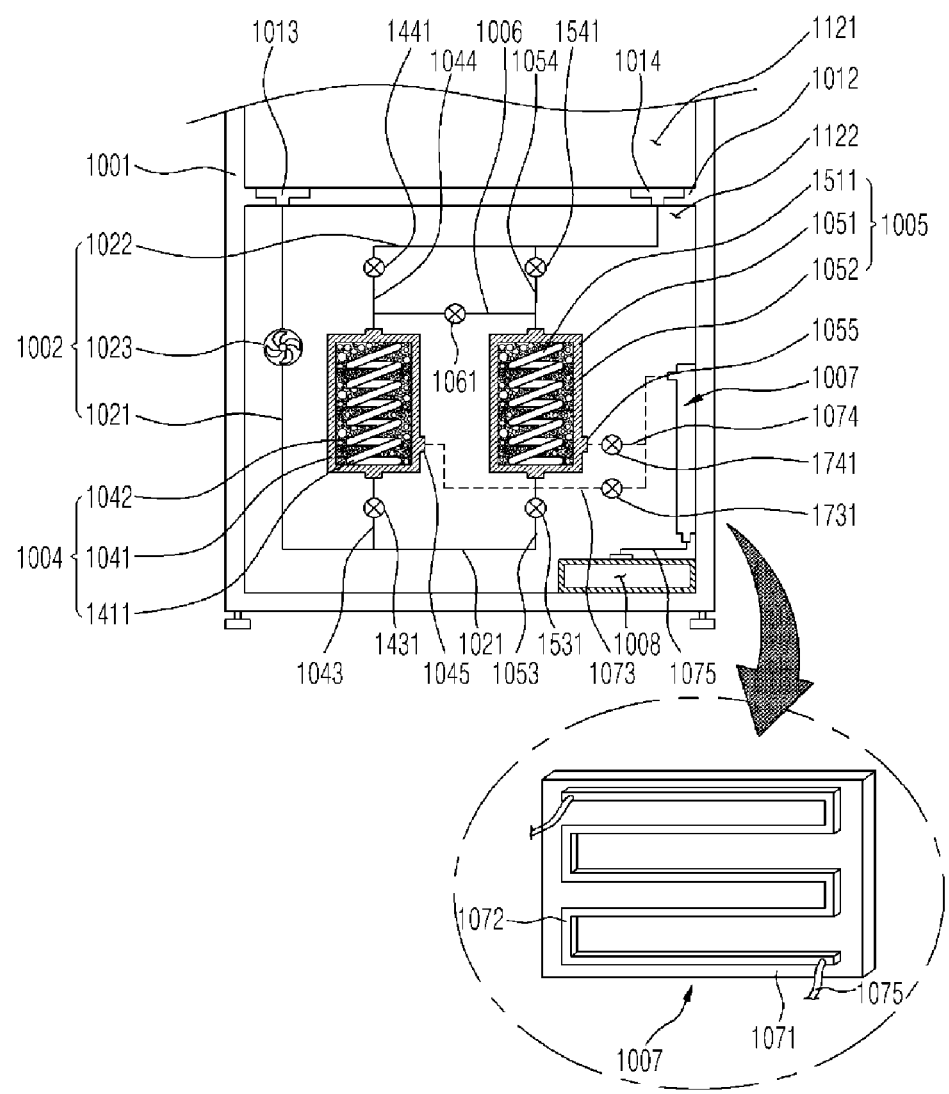
FIG. 39 illustrates an example of a dehumidifying unit.

As shown in FIG. 39, a dehumidifying unit 1002, 1004, 1005, and 1006 for removing moisture from the air discharged from the first chamber 1121 is provided in the second chamber 1122.

The dehumidifying unit can be configured to include ducts 1002 that configure paths connected to the first chamber 1121, a first dehumidifier 1004 and a second dehumidifier 1005 for removing moisture from the air moving along the ducts 1002, and a communicating pipe 1006 connecting the discharge paths of the dehumidifiers 1004 and 1005.

The ducts 1002 can be configured to include a first duct 1021 connected to the discharge hole 1013 to guide the air inside the first chamber 1121 to the second chamber 1122, and a second duct 1022 connected to the supply hole 1014 to supply air to the first chamber. A fan 1023 can be provided in any one of the first duct 1021 and the second duct 1022, and FIG. 39 illustrates an example in which the fan 1023 is provided in the first duct 1021.

The first dehumidifier 1004 can be configured to include a first housing 1041 positioned inside the second chamber 1122, a first dehumidifying material 1042 provided inside the first housing 1041 to absorb moisture contained in air, and a first heater 1411 provided inside the first housing 1041 to remove moisture absorbed by the first dehumidifying material 1042.

Figure 40:
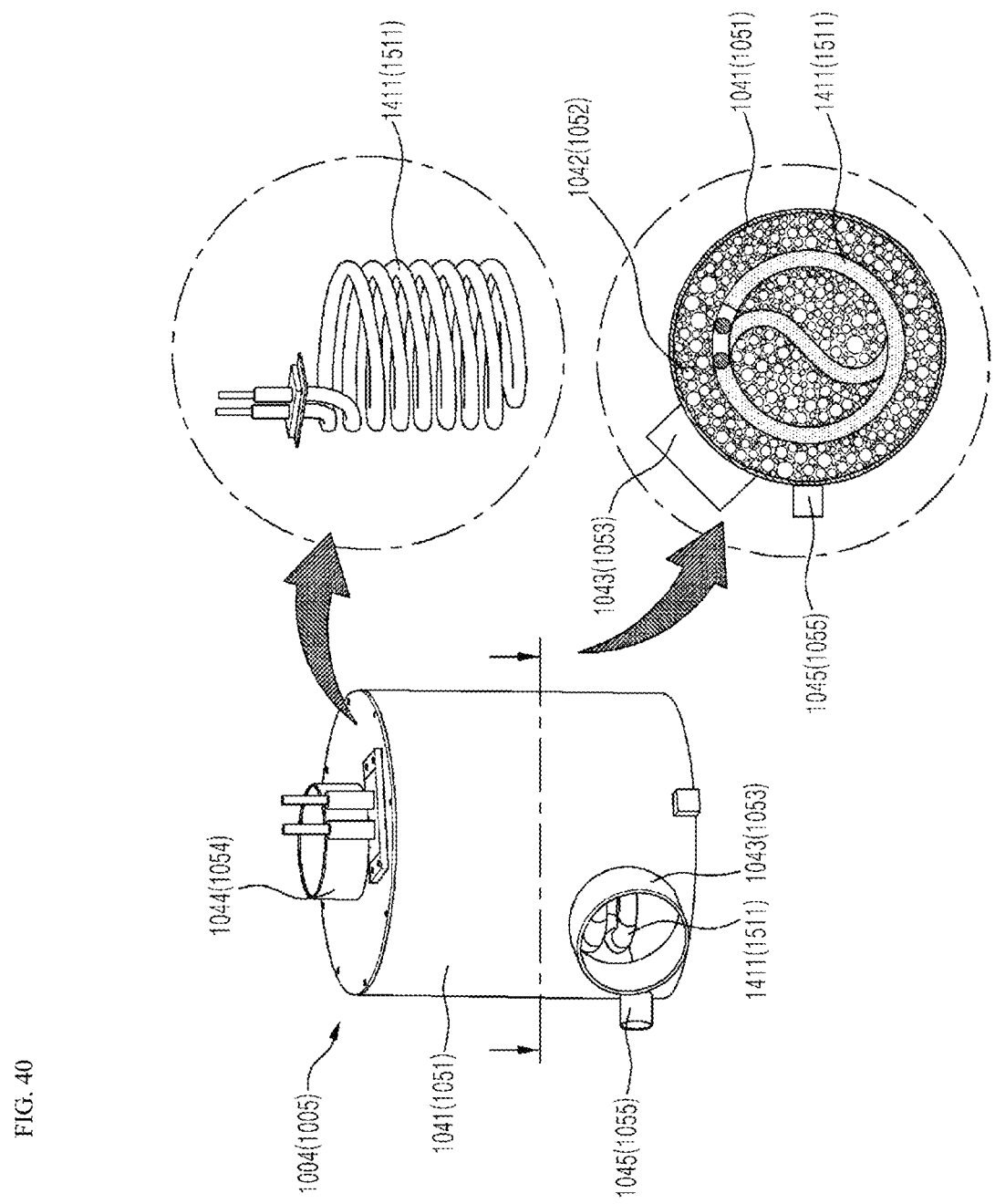
FIGS. 40 and 41 illustrate examples of a first dehumidifier and a second dehumidifier.

The first housing 1041 can have any shape as long as it is able to accommodate the first heater 1411 and the first dehumidifying material 1042, and FIG. 40 shows an example in which the first housing 1041 is configured in a hollow cylindrical shape and in which the first heater 1411 is provided as a heating wire in a coil shape. Unlike the drawings, the first heater 1411 can be configured as a ring-shaped heating wire.

The first dehumidifying material 1042 can be formed of a microporous material capable of adsorbing and removing moisture from the air, such as desiccant or zeolite. Moisture and odor particles contained in the air can be absorbed into the space formed between the materials constituting the first dehumidifying material 1042, and the moisture and the like absorbed into the first dehumidifying material can be released from the first dehumidifying material when heat is supplied from the outside.

As shown in the drawings, the first dehumidifying material 1042 can be provided inside the first housing 1041 to be positioned both in the inner space of the first heater 1411 (the space corresponding to the center of the ring-shaped or coil-shaped first heater) and in the outer space thereof (the outer space of the ring-shaped or coil-shaped first heater). That is, the diameter of the first heater 1411 can be configured to be smaller than the diameter of the first housing 1041. The configuration in which the first dehumidifying material 1042 is positioned both in the inner space and in the outer space of the first heater 1411 is intended to quickly transfer the heat emitted from the first heater 1411 to the first dehumidifying material 1042.

As shown in FIG. 39, the first housing 1041 can be connected to the first duct 1021 through first supply path 1043 and valve 1431, and can be connected to the second duct 1022 through first discharge path 1044 and valve 1441. That is, the first dehumidifier 1004 can have a first supply path 1043 for connecting the first duct 1021 to the first housing 1041, and a first discharge path 1044 for connecting the first housing 1041 to the second duct 1022.

A first supply valve 1431 can be provided in the first supply path 1043, and a first discharge valve 1441 can be provided in the first discharge path 1044. The first supply valve 1431 can be configured to open or close the first supply path 1043 according to a control signal of a controller, and the first discharge valve 1441 can be configured to open or close the first discharge path 1044 according to a control signal of the controller.

The second dehumidifier 1005 can be configured to include a second housing 1051 positioned inside the second chamber 1122, a second dehumidifying material 1052 provided inside the second housing 1051 to absorb moisture contained in the air, and a second heater 1511 provided inside the second housing 1051 to remove moisture absorbed into the second dehumidifying material 1052.

The second housing 1051 can be configured in a hollow cylindrical shape, and the second heater 1511 can be configured as a ring-shaped or coil-shaped heating wire. Like the first dehumidifying material 1042, the second dehumidifying material 1052 can be formed of a microporous material (desiccant, zeolite, etc.) capable of adsorbing and removing moisture from the air.

As shown in FIG. 40, the second dehumidifying material 1052 can be configured to be positioned both in the inner space of the second heater 1511 (the space corresponding to the center of the ring-shaped or coil-shaped second heater) and in the outer space thereof (the outer space of the ring-shaped or coil-shaped second heater). The diameter of the second heater 1511 can be configured to be smaller than the diameter of the second housing 1051.

The configuration in which the second dehumidifying material 1052 is positioned both in the inner space and in the outer space of the second heater 1511 is intended to quickly transfer the heat emitted from the second heater 1511 to the second dehumidifying material 1052.

As shown in FIG. 39, the second housing 1051 can be connected to the first duct 1021 through second supply path 1053 and valve 1531, and can be connected to the second duct 1022 through second discharge path 1054 and valve 1541. That is, the second dehumidifier 1005 can have a second supply path 1053 for connecting the first duct 1021 to the second housing 1051, and a second discharge path 1054 for connecting the second housing 1051 to the second duct 1022, and a second supply valve 1531 can be provided in the second supply path 1053, and a second discharge valve 1541 can be provided in the second discharge path 1054. The second supply valve 1531 can be configured to open and close the second supply path 1053 according to a control signal of the controller, and the second discharge valve 1541 can be configured to open and close the second discharge path 1054 according to a control signal of the controller.

The first discharge path 1044 and the second discharge path 1054 can be connected to each other through a communicating pipe 1006, and the communicating pipe 1006 can further include a connection valve 1061. The connection valve 1061 can be configured to control the opening and closing of the communicating pipe 1006 according to a control signal of the controller.

Figure 41:
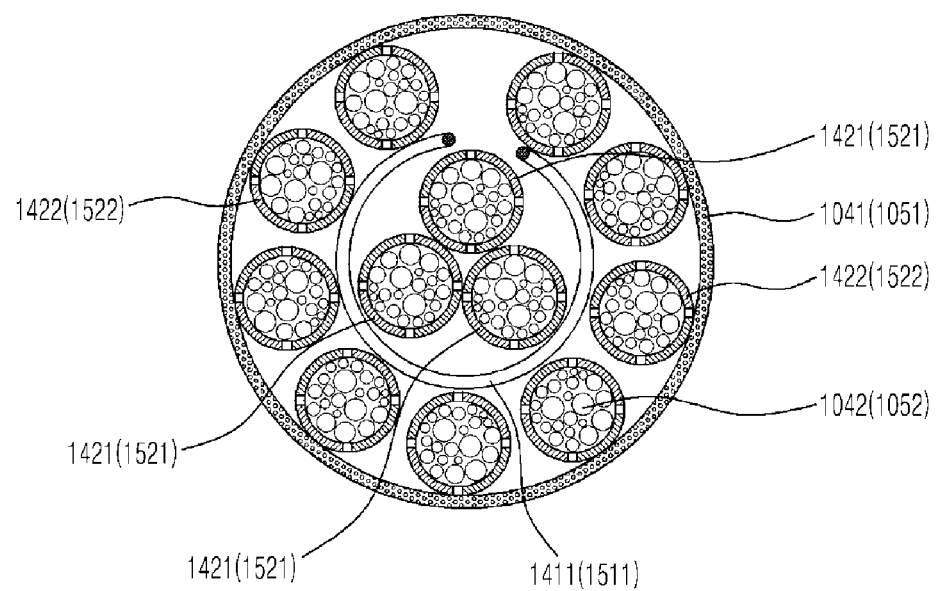

To make it easier for the heat emitted from the first heater 1411 to be transferred to the first dehumidifying material 1042, the first dehumidifier 1004 can further include a first dehumidifying material-first mesh 1421 and a first dehumidifying material-second mesh 1422. As shown in FIG. 41, the first dehumidifying material-first mesh 1421 can be configured as a mesh in a cylindrical or spherical shape to provide a space in which the first dehumidifying material 1042 is stored, and the first dehumidifying material-second mesh 1422 can be configured as a mesh to provide a space in which the first dehumidifying material 1042 is stored. In this case, the first dehumidifying material-first mesh 1421 can be located in the inner space of the first heater 1411, and the first dehumidifying material-second mesh 1422 can be located in the outer space of the first heater 1411.

Similarly, the second dehumidifier 1005 can further include a second dehumidifying material-first mesh 1521 and a second dehumidifying material-second mesh 1522. The second dehumidifying material-first mesh 1521 can be configured as a mesh to provide a space in which the second dehumidifying material 1052 is stored, and can be positioned in the inner space of the second heater 1511 (the inner space formed by the second heater), and the second dehumidifying material-second mesh 1522 can be configured as a mesh to provide a space in which the second dehumidifying material 1052 is stored, and can be positioned in the outer space of the second heater 1511 (the space formed between the second heater and the second housing).

In the case where the first dehumidifying material 1042 and the second dehumidifying material 1052 are stored in the meshes 1421, 1422, 1521, and 1522 and are respectively provided in the inner spaces and the outer spaces of the respective heaters, air can easily move to the spaces formed between the meshes, thereby providing the effect of facilitating heat exchange between the heat emitted from the heaters 1411 and 1511 and the dehumidifying materials stored inside the respective meshes (shortening regeneration time and minimizing energy for regeneration).

In order to prevent moisture released from the dehumidifying materials from being discharged to the outside of the drying apparatus 1100 or being supplied to the first chamber 1121 when the dehumidifying materials 1042 and 1052 are regenerated, the second chamber 1122 can further have a condensing unit 1007 and a condensate water storage unit 1008.

As shown in FIG. 39, the condensing unit 1007 can be configured to include a radiation body 1071 provided in the second chamber 1122 and a condensing path 1072 provided in the radiation body to configure a movement path of air.

The radiation body 1071 can be made of a metal material having high thermal conductivity, and the condensing path 1072 can be configured as a metal pipe forming a zigzag path along the surface of the radiation body 1071. The first housing 1041 can be connected to the condensing path 1072 through a first connection pipe 1073, and the second housing 1051 can be connected to the condensing path 1072 through a second connection pipe 1074.

In this case, the first connection pipe 1073 can be configured to connect a drain 1045 (a first drain) of the first housing and the condensing path 1072, and the second connection pipe 1074 can be configured to connect a drain 1055 (a second drain) of the second housing and the condensing path 1072.

The first connection pipe 1073 can be provided with a first connection valve 1731 for opening and closing the first connection pipe 1073 according to a control signal of the controller, and the second connection pipe 1074 can be provided with a second connection valve 1741 for opening and closing the second connection pipe 1074 according to a control signal of the controller.

The condensate water storage unit 1008 can be connected to the condensing path 1072 through a drainage path 1075, and the condensate water storage unit 1008 can be configured as a storage tank that is detachable from the second chamber 1122.

Figure 42:
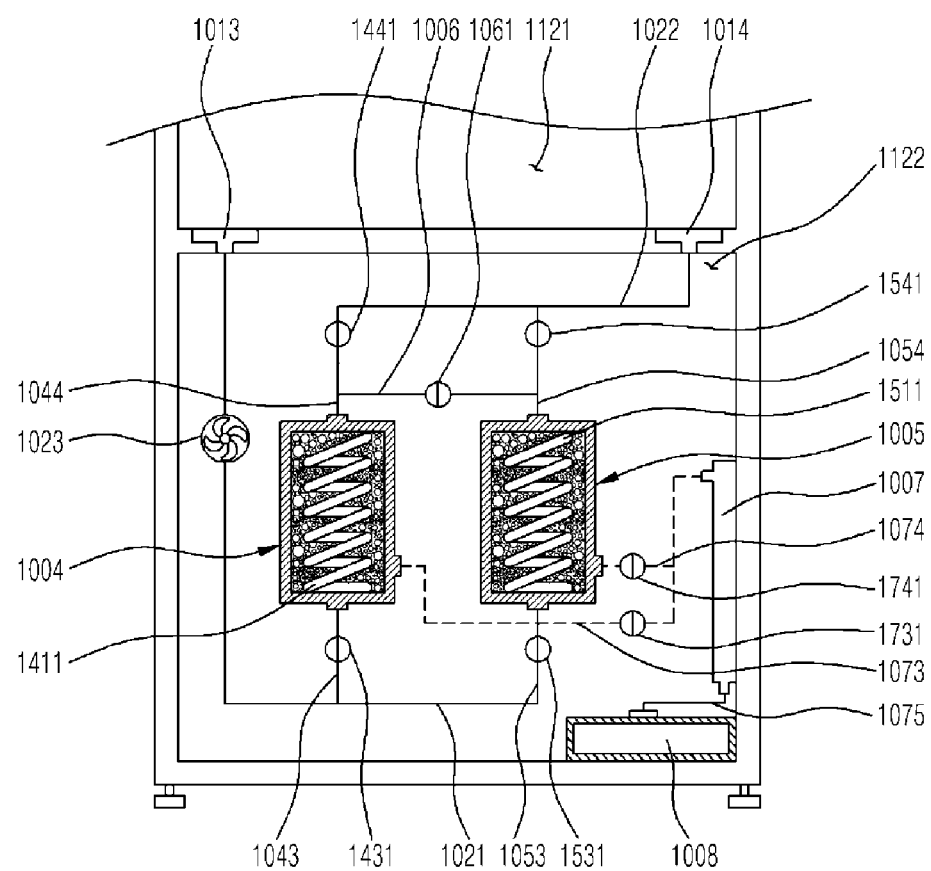
FIGS. 42, 43, and 44 illustrate an example of an operation process of a dehumidifying unit.

FIG. 42 shows a first mode in which both the first dehumidifier 1004 and the second dehumidifier 1005 perform a dehumidification cycle (a cycle for absorbing moisture from air).

In the first mode, the controller can control the first supply valve 1431, the second supply valve 1531, the first discharge valve 1441, and the second discharge valve 1541 such that the first supply path 1043, the first discharge path 1044, the second supply path 1053, and the second discharge path 1054 are opened. In the first mode, the controller can close the communicating pipe 1006, the first connection pipe 1073, and the second connection pipe 1074 through the connection valve 1061, the first connection valve 1731, and the second connection valve 1741, and may not operate the first heater 1411 and the second heater 1511.

If the fan 1023 is operated in the above-described state, the air in the first chamber 1121 can flow into the first duct 1021 through the discharge hole 1013, and then flow to the first housing 1041 and the second housing 1051. The air supplied to the first housing 1041 can move to the first discharge path 1044 by passing through the first dehumidifying material 1042, and the air supplied to the second housing 1051 can move to the second discharge path 1054 by passing through the second dehumidifying material 1052.

The air passing through the first dehumidifying material 1042 and the second dehumidifying material 1052 can move to the second duct 1022 through the first discharge path 1044 and the second discharge path 1054, and the air inside the second duct 1022 can be supplied to the first chamber 1121 through the supply hole 1014. Accordingly, the drying apparatus can remove moisture from the drying object received in the first chamber 1121 in the first mode.

Figure 43:
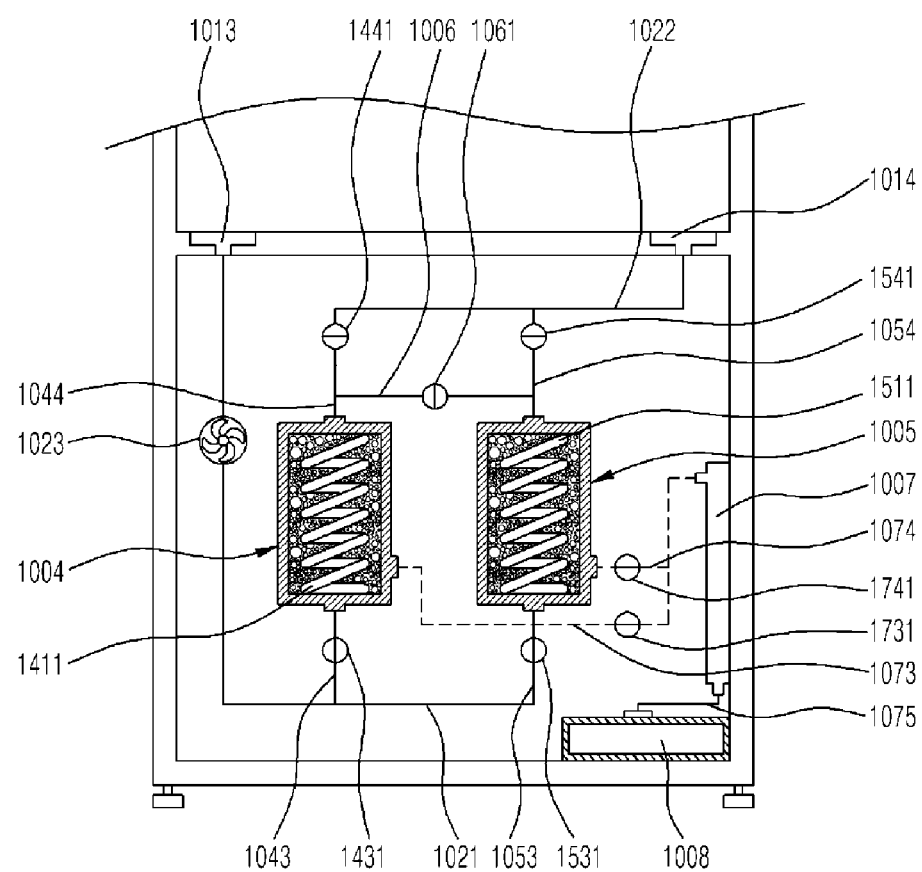

FIG. 43 shows a second mode in which both the first dehumidifier 1004 and the second dehumidifier 1005 perform a regeneration cycle (a cycle of separating moisture absorbed into the dehumidifying material from the dehumidifying material).

In the second mode, the controller can control the first supply valve 1431, the first discharge valve 1441, the second supply valve 1531, and the second discharge valve 1541 such that the first supply path 1043 and the second supply path 1053 are opened and such that the first discharge valve 1441 and the second discharge valve 1541 are closed. In addition, in the second mode, the controller can control the connection valve 1061, the first connection valve 1731, and the second connection valve 1741 such that the communicating pipe 1006 is closed and such that the first connection pipe 1073 and the second connection pipe 1074 are opened.

In the second mode described above, the fan 1023, the first heater 1411, and the second heater 1511 can be operated. When electric power is supplied to the first heater 1411 and the second heater 1511 (when the first heater and the second heater emit heat), the moisture contained in the first dehumidifying material 1042 can be discharged to the first housing 1041, and the moisture contained in the second dehumidifying material 1052 can be discharged to the second housing 1051.

As the air inside the first chamber 1121 is supplied to the first housing 1041 and the second housing 1051 through the first duct 1021, the first supply path 1043, and the second supply path 1053 when the fan 1023 is operated, the moisture stored in the first housing 1041 can move to the condensing path 1072 through the first connection pipe 1073, and the moisture stored in the second housing 1051 can move to the condensing path 1072 through the second connection pipe 1074.

The condensing path 1072 can be fixed to the radiation body 1071, and the radiation body 1071 can be configured to exchange heat with the air inside the second chamber 1122. Accordingly, the air moving along the condensing path 1072 can be cooled, and in this process, the moisture contained in the air can be separated from the air into condensate water. The condensate water stored in the condensing path 1072 can move to the condensate water storage unit 1008 through the drainage path 1075. Accordingly, the drying apparatus 1100 can prevent the humid air discharged during regeneration of the dehumidifiers 1004 and 1005 from being supplied to the drying object or the indoor space in which the drying apparatus is installed.

Figure 44:
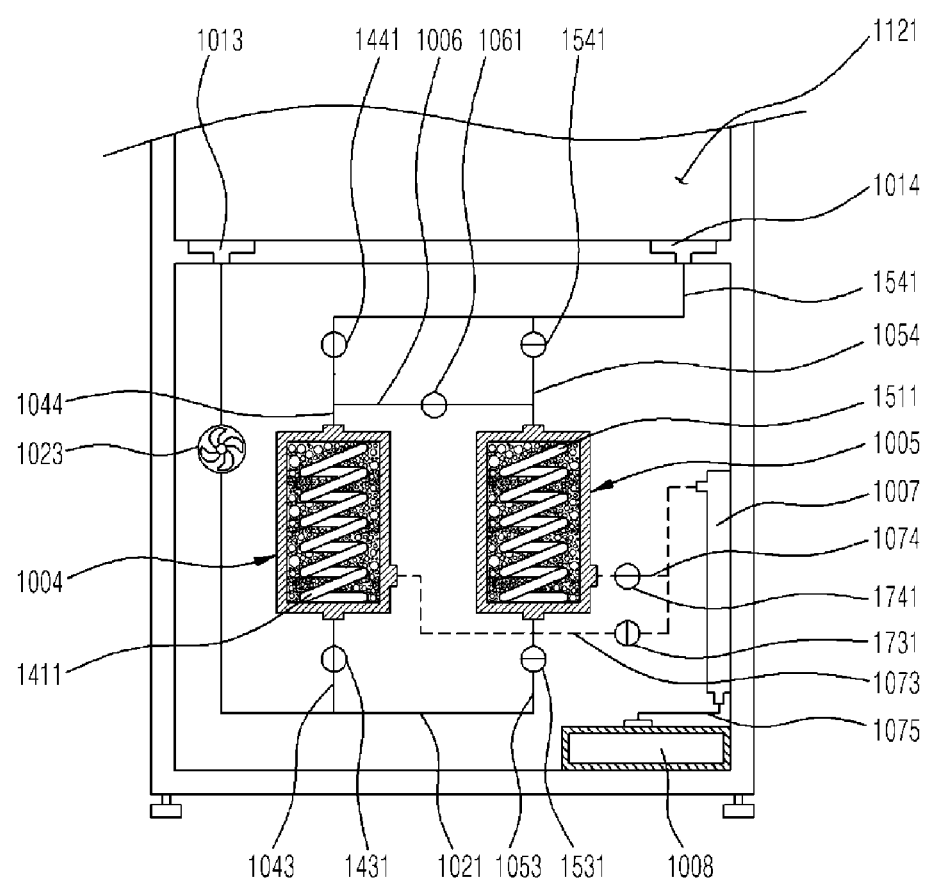

FIG. 44 shows a mode (a third mode) in which one of the first dehumidifier 1004 and the second dehumidifier 1005 performs a dehumidification cycle and the remaining one performs a regeneration cycle.

In the third mode, the controller can operate the second heater 1511 in the state in which the first supply path 1043 and the first discharge path 1044 are opened and in which the second supply path 1053 and the second discharge path 1054 are closed. In some examples, the controller can control the first connection valve 1731 and the second connection valve 1741 such that the first connection pipe 1073 is closed and such that the second connection pipe 1074 is opened.

In addition, in the third mode, the controller can control the connection valve 1061 such that the communicating pipe 1006 is opened. In some examples, the controller can perform control in the third mode such that the amount of air supplied to the first discharge path 1044 is larger than the amount of air supplied to the communicating pipe 1006.

That is, in the third mode, the controller can control the connection valve 1061 such that the flow rate through the communicating pipe 1006 is smaller than the flow rate through the first discharge path 1044.

The air having moved to the first discharge path 1044 can be supplied to the first chamber 1121 through the second duct 1022 and the supply hole 1014. In some examples, the air having moved to the communicating pipe 1006 can flow to the condensing path 1072 through the second discharge path 1054, the second housing 1051, and the second connection pipe 1074, and in this process, the moisture stored inside the second housing 1051 (the moisture discharged from the second dehumidifying material during the operation of the second heater) can move to the condensing path 1072.

In some implementations, in the third mode, the first heater 1411 can be operated in the state in which the first supply path 1043 and the first discharge path 1044 are closed and in which the second supply path 1053 and the second discharge path 1054 are opened. In this case, the controller can control the connection valve 1061, the first connection valve 1731, and the second connection valve 1741 such that the communicating pipe 1006 and the first connection pipe 1073 are opened and such that the second connection pipe 1074 is closed.

Figure 45:
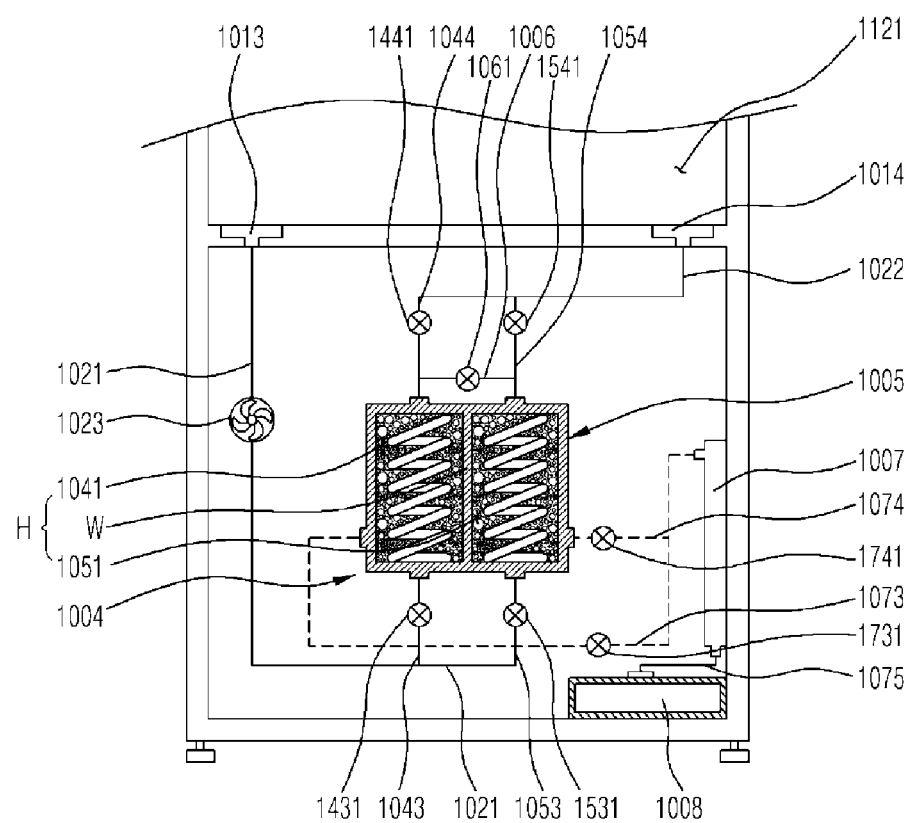
FIGS. 45 to 49 illustrate examples of dehumidifying units.

FIG. 45 illustrates an example of a drying apparatus 1100, which shows a drying apparatus 1100 equipped with a first housing 1041 and a second housing 1051 in one dehumidifier housing H.

That is, the drying apparatus 1100 in FIG. 45 can be configured to include a dehumidifier housing H provided in the second chamber 1122 and a housing partition W that separates the inside of the dehumidifier housing into a first housing 1041 and a second housing 1051.

The first supply path 1043 and the first discharge path 1044 can be connected to the dehumidifier housing H so as to communicate with the first housing 1041, and the second supply path 1053 and the second discharge path 1054 can be connected to the dehumidifier housing H so as to communicate with the second housing 1051.

If the first housing 1041 and the second housing 1051 are configured to be separated by the housing partition W, the heat inside the dehumidifier executing the dehumidification cycle can be transferred to the dehumidifier executing the regeneration cycle in the third mode, thereby reducing the energy for the regeneration cycle.

Figure 46:
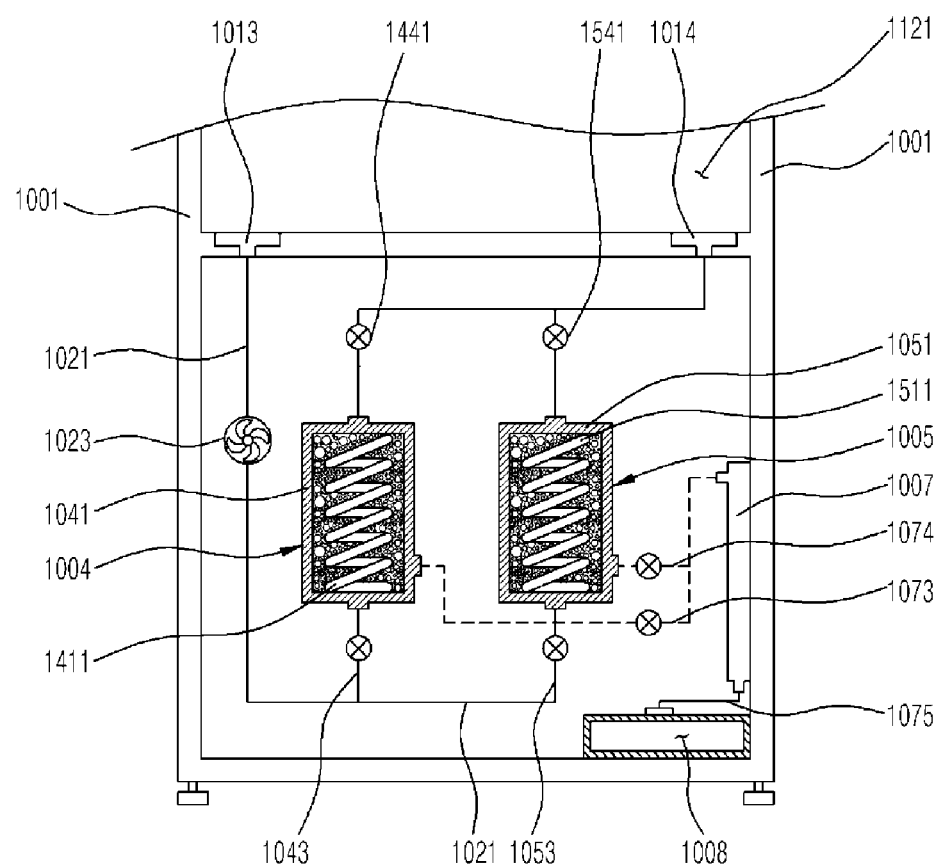

FIG. 46 illustrates an example of a drying apparatus 1100 in which the drying apparatus 1100 is distinguished from the drying apparatuses shown in FIGS. 38 to 45 in that the communicating pipe 1006 connecting the first discharge path 1044 and the second discharge path 1054 is not provided in some examples.

The drying apparatus 1100 excluding the communicating pipe 1006 and the connection valve 1061 can operate as follows. The drying apparatus 1100 in FIG. 46 can control the first connection valve 1731 and the second connection valve 1741 such that the first connection pipe 1073 and the second connection pipe 1074 are closed, control the first supply valve 1431, the second supply valve 1531, the first discharge valve 1441, and the second discharge valve 1541 such that all of the first supply path 1043, the second supply path 1053, the first discharge path 1044, and the second discharge path 1054 are opened, and then operate the fan 1023, thereby performing a first mode (a mode in which both dehumidifiers execute a dehumidification cycle).

In some examples, the drying apparatus 1100 in FIG. 46 can control the first connection valve 1731, the second connection valve 1741, the first supply valve 1431, and the second supply valve 1531 such that the first connection pipe 1073, the second connection pipe 1074, the first supply path 1043, and the second supply path 1053 are opened, control the first discharge valve 1441 and the second discharge valve 1541 such that the first discharge path 1044 and the second discharge path 1054 are closed, and then operate the fan 1023 and the heaters 1411 and 1511, thereby performing a second mode (a mode in which both dehumidifiers execute a regeneration cycle).

In addition, the drying apparatus 1100 in FIG. 46 can open the first supply path 1043, the second supply path 1053, the first discharge path 1044, and the second connection pipe 1074, close the second discharge path and the first connector or valve 1073, and then operate the fan 1023 and the second heater 1511, thereby performing a third mode in which the first dehumidifier 1004 executes a dehumidification cycle and in which the second dehumidifier 1005 executes a regeneration cycle.

The air passing through the first dehumidifier 1004 (dehumidified air) is supplied to the second dehumidifier in the drying apparatus in FIG. 38, whereas the air discharged from the first chamber 1121 is supplied to the second dehumidifier 1005 in the drying apparatus in FIG. 46. This indicates that the drying apparatus in FIG. 38 removes moisture from the air discharged from the first chamber 1121 and then supplies the air to the second dehumidifier, and that the drying apparatus in FIG. 46 directly supplies the air discharged from the first chamber 1121 to the second dehumidifier. Therefore, the drying apparatuses in FIGS. 38 to 45 is advantageous compared to the drying apparatus in FIG. 46 in consideration of only the regeneration efficiency of the dehumidifying material.

Figure 47:
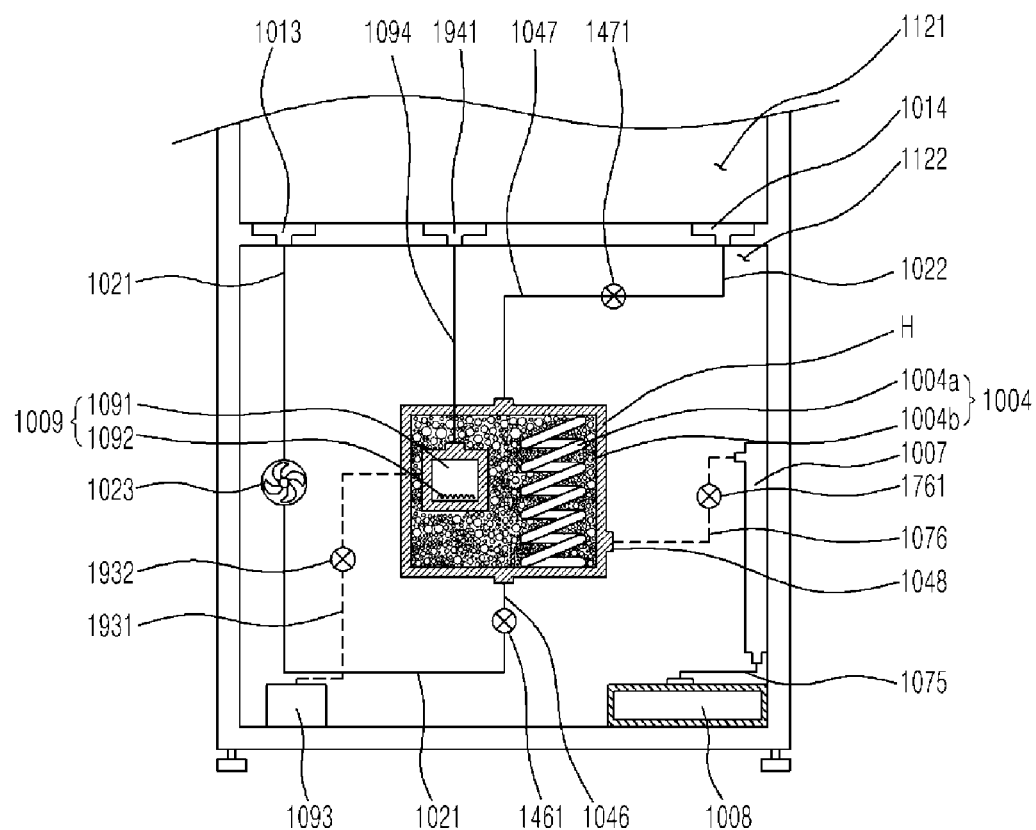

FIG. 47 illustrates an example of a drying apparatus. The structure of a dehumidifying unit of the drying apparatus 1100 is distinguished from the dehumidifying units provided in the drying apparatuses in FIGS. 38 to 46.

The drying apparatus in FIG. 47 can be configured to include a cabinet 1001 equipped with a first chamber 1121 (a drying chamber) and a second chamber 1122, a dehumidifying unit 1002 and 1004 provided in the second chamber 1122, a condensing unit 1007 for removing moisture from the air discharged from the dehumidifying unit, a condensate water storage unit 1008 for storing condensate water discharged from the condensing unit, and a steam supply unit 1009 for supplying steam to the first chamber 1121. Since the structure of the cabinet 1001 is the same as that of the cabinet provided in the drying apparatuses in FIGS. 38 to 46, a detailed description thereof will be omitted.

The dehumidifying unit can be configured to include a duct 1002 provided in the second chamber 1122 and a dehumidifier 1004 connected to the duct 1002. The duct 1002 can be configured to include a first duct 1021 connected to the discharge hole 1013 and a second duct 1022 connected to the supply hole 1014, and the first duct 1021 can have a fan 1023 provided therein.

The dehumidifier 1004 can be configured to include a dehumidifier housing H provided in the second chamber 1122, and a heater 1004a and a dehumidifying material 1004b provided inside the dehumidifier housing. The dehumidifier housing H can be connected to the first duct 1021 through a supply path 1046 and valve 1461 and can be connected to the second duct 1022 through a discharge path 1047 and valve 1471.

The supply controller can be configured to include a supply path 1046 connected between the first duct 1021 and the dehumidifier housing H, and a supply valve 1461 for controlling the opening and closing of the supply path, and the discharge controller can be configured to include a discharge path 1047 connected between the dehumidifier housing H and the second duct 1022, and a discharge valve 1471 for controlling the opening and closing of the discharge path.

The condensing unit 1007 can be configured to include a radiation body 1071 provided in the second chamber 1122 and a condensing path 1072 provided in the radiation body to configure a movement path of air.

The radiation body 1071 can be made of a metal material having high thermal conductivity, and the condensing path 1072 can be configured as a metal pipe forming a zigzag path along the surface of the radiation body 1071. The dehumidifier housing H can be connected to the condensing path 1072 through a connection pipe 1076. The connection pipe 1076 can be connected between a drain 1048 of the dehumidifier housing and the condensing path 1072, and can be configured to be opened and closed by a connection valve 1761.

The condensate water storage unit 1008 can be configured as a storage tank detachably provided in the second chamber 1122, and can be connected to the condensing path 1072 through a drainage path 1075.

The steam supply unit 1009 can be configured to include a water storage unit 1091 provided inside the dehumidifier housing H to provide a space for storing water, a steam heater 1092 provided inside the water storage unit, and a steam path 1094 for guiding the steam inside the water storage unit to the first chamber 1121. The steam path 1094 can be configured as a pipe connected between a nozzle 1941 provided on the partition 1012 and the upper surface of the water storage unit 1091.

The second chamber 1122 can have a water supply tank 1093 storing water and detachably provided in the second chamber, a water supply path 1931 connected between the water supply tank and the water storage unit 1091, and a water supply pump 1932 for supplying water in the water supply tank to the water storage unit 1091 through the water supply path 1931.

In the drying apparatus 1100 in FIG. 47, since the water storage unit 1091 is provided inside the dehumidifier housing H, there is an effect of regenerating the dehumidifying material 1004b with the heat emitted from the water storage unit 1091 when the steam heater 1092 is operated or after the operation of the steam heater is completed. That is, the drying apparatus in FIG. 47 can close the supply path 1046 and the discharge path 1047 and open the connection pipe 1076 when the steam heater 1092 is operated, thereby removing the moisture contained in the dehumidifying material 1004b.

In some implementations, the steam supply unit 1009 in FIG. 47 can be provided in the drying apparatuses in FIGS. 38 to 45. That is, the water storage unit 1091 provided in the steam supply unit can be provided to be positioned inside any one of the first housing 1041 and the second housing 1051 in FIGS. 38 to 45.

Figure 48:
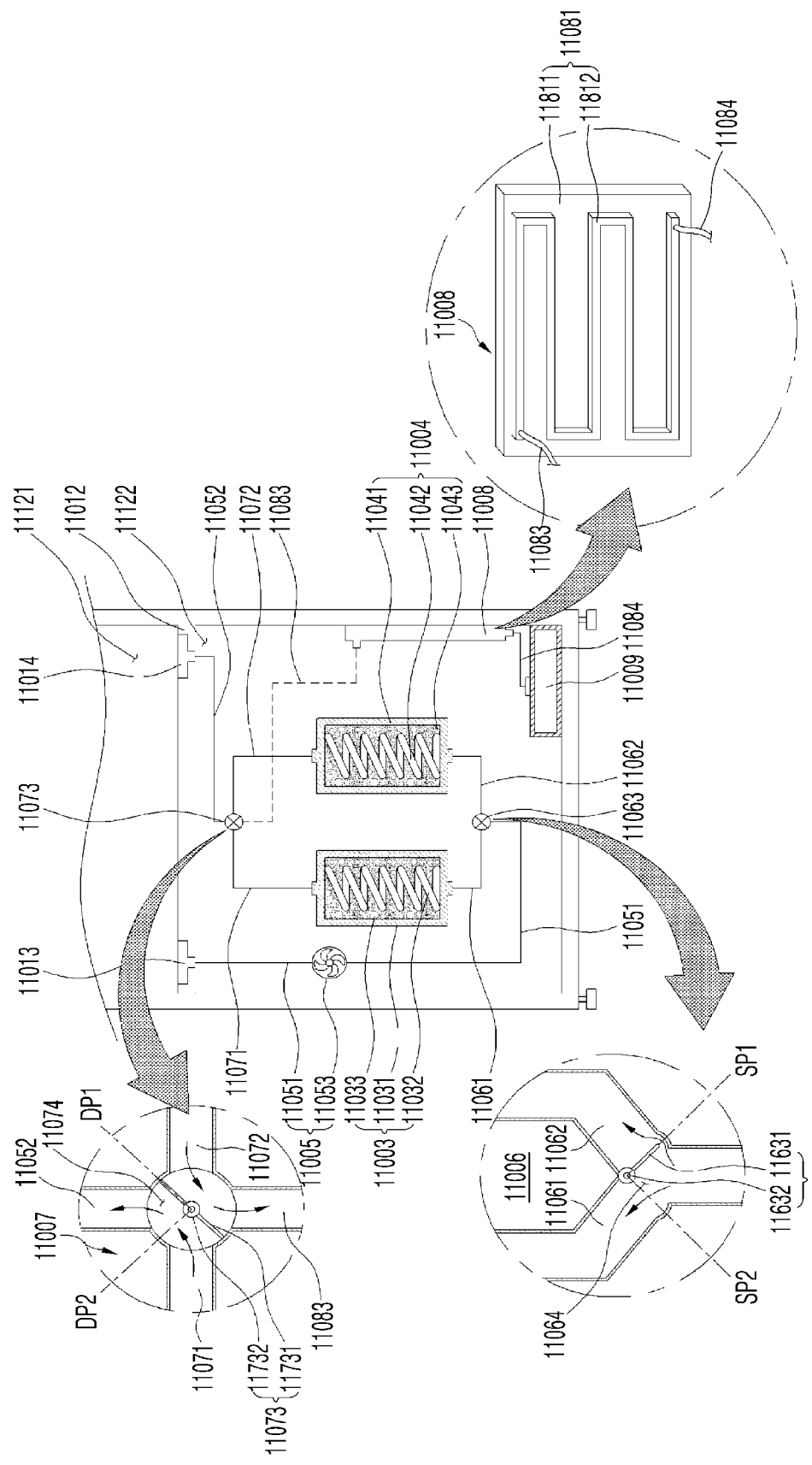

FIG. 48 illustrates an example of a drying apparatus.

As shown in FIG. 48, a dehumidifying unit or system 11003, 11004, 11005, 11006, and 11007 for removing moisture from the air discharged from the first chamber 11121 can be provided in the second chamber 11122.

For example, the dehumidifying unit can include a duct 11005 configuring a path connected to the first chamber 11121, and a first dehumidifier 11003, and a second dehumidifier 11004 for removing moisture from the air moving through the duct 11005.

The duct 11005 can be configured to include a first duct 11051 connected to the discharge hole 11013 to guide the air inside the first chamber 11121 to the second chamber 11122 and a second duct 11052 connected to the supply hole 11014 to supply air to the first chamber. A fan 11053 can be provided in any one of the first duct 11051 and the second duct 11052, and FIG. 48 shows an example in which the fan 11053 is provided in the first duct 11051.

The first dehumidifier 11003 can be configured to include a first housing 11031 positioned inside the second chamber 11122, a first dehumidifying material 11033 provided inside the first housing 11031 to absorb moisture contained in the air, and a first heater 11032 provided inside the first housing 11031 to remove the moisture absorbed into the first dehumidifying material 11033.

As shown in the drawing, the first dehumidifying material 11033 can be provided inside the first housing 11031 to be positioned both in the inner space of the first heater 11032 (the space corresponding to the center of the ring-shaped or coil-shaped first heater) and in the outer space thereof (the outer space of the ring-shaped or coil-shaped first heater). That is, the diameter of the first heater 11032 can be configured to be smaller than the diameter of the first housing 11031. The configuration in which the first dehumidifying material 11033 is positioned both in the inner space and in the outer space of the first heater 11032 is intended to quickly transfer the heat emitted from the first heater 11032 to the first dehumidifying material 11033.

The second dehumidifier 11004 can be configured to include a second housing 11041 positioned inside the second chamber 11122, and a second dehumidifying material 11043 provided inside the second housing 11041 to absorb moisture contained in the air, and a second heater 11042 that is provided inside the second housing 11041 and removes moisture absorbed into the second dehumidifying material 11043.

As shown in FIG. 48, the first housing 11031 and the second housing 11041 can be connected to the first duct 11051 through the supply path 11006, and can be connected to the second duct 11052 through the discharge path 11007.

The supply path 11006 can be configured to include a first supply path 11061 for supplying air to the first housing 11031 and a second supply path 11062 for supplying air to the second housing 11041.

The first duct 11051, the first supply path 11061, and the second supply path 11062 can be connected to each other through a supply chamber 11064, and a supply valve 11063 for controlling opening and closing of the first supply path 11061 and the second supply path 11062 according to a control signal of a controller can be provided inside the supply chamber 11064. For instance, the controller can include one or more processors, an electric circuit, or the like, that can control various devices including valves, fans, condensers, sensors, regulators, and the like.

The supply valve 11063 can be configured to include a first shaft 11632 fixed to the supply chamber 11064, a supply valve body 11631 rotating about the first shaft 11632, and a first driving unit for moving the supply valve body 11631 to reciprocate between a first supply point and a second supply point according to a control signal from the controller. The first driving unit can be configured as a motor that rotates the first shaft 11632.

The first supply point SP1 can be configured as a point where the degree of opening of the first supply path 11061 is greater than the degree of opening of the second supply path 11062, and the second supply point SP2 can be configured as a point where the degree of opening of the second supply path 11062 is greater than the degree of opening of the first supply path 11061.

FIG. 48 illustrates an example of the first supply point SP1 and the second supply point SP2. That is, FIG. 48 shows the case in which the point where the degree of opening of the first supply path 11061 is 90% or more and where the degree of opening of the second supply path 11062 is 10% or less is configured as the first supply point SP1, and in which the point where the degree of opening of the first supply path 11061 is 10% or less and where the degree of opening of the second supply path 11062 is 90% or more is configured as the second supply point SP2.

The discharge path 11007 can be configured to include a first discharge path 11071 configuring a path of the air discharged from the first housing 11031, and a second discharge path 11072 configuring a path of the air discharged from the second housing 11041. The second duct 11052, the first discharge path 11071, and the second discharge path 11072 can be connected through the discharge chamber 11074, and a discharge valve 11073 can be configured inside the discharge chamber 11074.

In order to store, in the second chamber 11122, the moisture discharged from the respective dehumidifiers 11003 and 11004 when the first dehumidifying material 11033 and the second dehumidifying material 11043 are regenerated (in order to prevent the moisture discharged from the dehumidifying material from being discharge to the outside of the first chamber or cabinet), the drying apparatus 11100 can further include a condensing unit 11008 and a storage unit 11009.

The condensing unit 11008 can be configured to include a condenser 11081 provided in the second chamber 11122, and a connection path 11083 connected between the discharge path 11007 and the condenser 11081, and the storage unit 11009 can be configured as a storage tank that is detachably installed to the second chamber 11122. The storage tank can be configured in any shape as long as it can store water, and can be configured to be connected to the condenser 11081 through a drainage path 11084.

The condenser 11081 can be configured to include a radiation body 11811 that is fixed to the second chamber 11122 and exchanges heat with the air inside the second chamber 11122, and a condensing path 11812 that is provided in the radiation body 11811 and guides the air supplied from the connection path 11083 to the drainage path 11084.

The radiation body 11811 can be made of a metal material having high thermal conductivity, and the condensing path 11812 can be configured as a metal pipe forming a zigzag path along the surface of the radiation body 11811. In this case, the connection path 11083 can be configured to connect the discharge chamber 11074 and the condensing path 11812.

The discharge chamber 11074 can be configured as a hollow cylindrical body. In this case, the second duct 11052, the first discharge path 11071, the second discharge path 11072, and the connection path 11083 can be connected to the discharge chamber 11074 so as to be spaced apart from each other at 90 degrees along the circumferential surface thereof.

The discharge valve 11073 can be configured to include a second shaft 11732 positioned on the central axis of the discharge chamber 11074, a discharge valve body 11731 rotating about the second shaft 11732, and a second driving unit for moving the discharge valve body 11731 to reciprocate between a first discharge point DP1 and a second discharge point DP2 by rotating the second shaft 11732. The second driving unit can be configured as a motor for rotating the second shaft 11732.

The first discharge point DP1 can be configured as a point where the first discharge path 11071 is connected to the second duct 11052 and where the second discharge path 11072 is connected to the connection path 11083, and the second discharge point DP2 can be configured as a point where the first discharge path 11071 is connected to the connection path 11083 and where the second discharge path 11072 is connected to the second duct 11052.

The position of the supply valve 11063 and the position of the discharge valve 11073 can be controlled by a controller. That is, if the supply valve 11063 is located at the first supply point SP1, the discharge valve 11073 can be controlled to be located at the first discharge point DP1, and if the supply valve 11063 is located at the second supply point SP2, the discharge valve 11073 can be controlled to be located at the second discharge point DP2.

The drying apparatus having the above-described structure can be controlled to execute a first mode and a second mode. The first dehumidifier 11003 performs a dehumidification cycle and the second dehumidifier 11004 performs a regeneration cycle in the first mode, and the first dehumidifier 11003 performs a regeneration cycle and the second dehumidifier 11004 performs a dehumidification cycle in the second mode.

Referring to FIG. 48, in the first mode, the controller can position the supply valve 11063 and the discharge valve 11073 at the first supply point SP1 and the first discharge point DP1, respectively, and then operate the fan 11053 and the second heater 11042.

When the fan 11053 rotates in the state in which the supply valve 11063 is located at the first supply point SP1, the air inside the first chamber 11121 can flow into the first duct 11051. A portion (90% or more) of the air inside the first duct 11051 can be supplied to the first dehumidifier 11003, and the remaining (10% or less) of the air can be supplied to the second dehumidifier 11004.

The air supplied to the first dehumidifier 11003 can be dehumidified while passing through the first dehumidifying material 11033, and the dehumidified air can move to first chamber 11121 through the first discharge path 11071 and the second duct 11052. When the above-described process is performed, the drying object located inside the first chamber 11121 can be dried.

In some examples, the moisture absorbed into the second dehumidifying material 11043 can be discharged to the outside of the second dehumidifying material 11043 when the second heater 11042 is operated, and the moisture released from the second dehumidifying material 11043 can move to the condensing path 11812 by passing through the second discharge path 11072 and the connection path 11083 due to the air supplied to the second dehumidifier 11004. The moisture discharged from the second dehumidifying material 11043 can be condensed while passing through the condensing path 11812, and condensate water inside the condensing path 11812 can flow to the storage unit 11009 through the drainage path 11084.

In the second mode, the controller can position the supply valve 11063 and the discharge valve 11073 at the second supply point SP2 and the second discharge point DP2, respectively, and then operate the fan 11053 and the first heater 11032.

If the fan 11053 rotates in the state in which the supply valve 11063 is located at the second supply point SP2, some (90% or more) of the air introduced into the first duct 11051 can be supplied to the second dehumidifier 11004, and the remainder (10% or less) of the air can be supplied to the first dehumidifier 11003.

The air supplied to the second dehumidifier 11004 can be dehumidified while passing through the second dehumidifying material 11043, and the dehumidified air can move to the first chamber 11121 through the second discharge path 11072 and the second duct 11052. When the above-described process is performed, the drying object located inside the first chamber 11121 can be dried.

In some examples, the moisture absorbed into the first dehumidifying material 11033 can be discharged to the outside of the first dehumidifying material 11033 when the first heater 11032 is operated, and the moisture released from the first dehumidifying material 11033 can move to the condensing path 11812 through the first discharge path 11071 and the connection path 11083 due to the air supplied to the first dehumidifier 11003. The moisture discharged from the first dehumidifying material 11033 can be condensed while passing through the condensing path 11812, and condensate water inside the condensing path 11812 can flow to the storage unit 11009 through the drainage path 11084.

Figure 49:
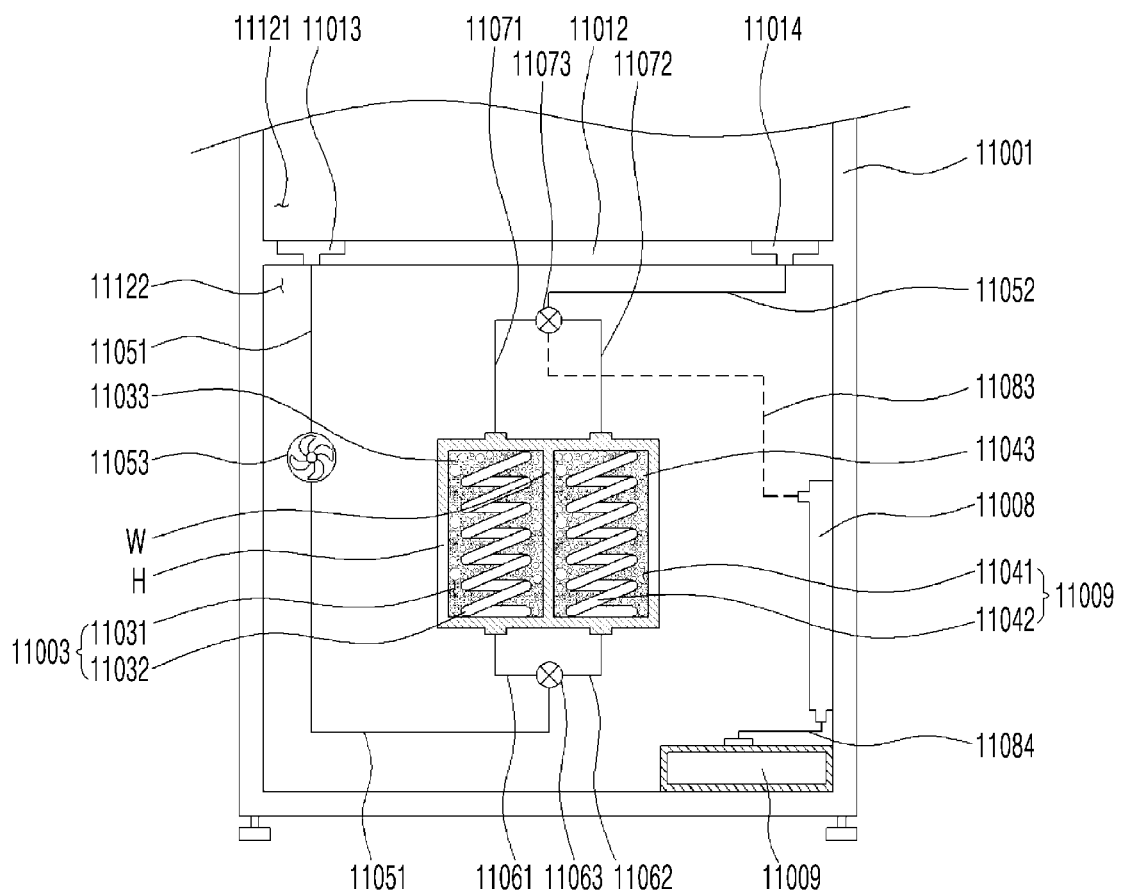

FIG. 49 illustrates an example of a drying apparatus 11100. In the drying apparatus 11100, both the first housing 11041 and the second housing 11051 are provided in one dehumidifier housing H. That is, the drying apparatus 11100 in FIG. 49 can be configured to include a dehumidifier housing H provided in the second chamber 11122 and a housing partition W for separating the inside of the dehumidifier housing into the first housing 11041 and the second housing 11051.

The first supply path 11061 and the first discharge path 11071 can be connected to the dehumidifier housing H so as to communicate with the first housing 11031, and the second supply path 11062 and the second discharge path 11072 can be connected to the dehumidifier housing H to communicate with the second housing 11041.

If the first housing 11041 and the second housing 11051 are provided to be separated by the housing partition W, the heat inside the dehumidifier executing a dehumidification cycle can be transferred to the dehumidifier executing a regeneration cycle, thereby reducing the energy for the regeneration cycle.

In the foregoing, although specific implementations of the present disclosure have been described and illustrated, the present disclosure is not limited to the described implementations, and it will be understood by those of ordinary skill in the art that there can be various changes and modifications into other specific implementations without departing from the spirit and scope of the present disclosure. Accordingly, the scope of the present disclosure should be defined by the technical idea described in the claims, instead of by the described implementations.

What is claimed is:
1. A shoe care device comprising:
an inner cabinet that has:
   an accommodation space configured to accommodate shoes therein,
   an inlet defined at a first portion of the accommodation space and configured to supply air to the accommodation space, and
   an outlet defined at a second portion of the accommodation space and configured to suction air from the accommodation space;

an air supply device configured to blow air to the accommodated space along a plurality of paths, the air supply device comprising a plurality of dehumidifying materials that are separate from one another and disposed in the plurality of paths, the air supply device being configured to heat the plurality of dehumidifying materials; and a controller configured to control the air supply device, wherein the plurality of paths of the air supply device comprise:
- a connection path configured to circulate air between the inlet and the outlet, and
- a regeneration path branched from the connection path and configured to guide air having passed through at least one of the plurality of dehumidifying materials to a portion of the air supply device other than the inlet, and wherein the controller is configured to control the air supply device to selectively open and close at least one of the connection path or the regeneration path based on whether or not at least one of the plurality of dehumidifying materials is heated.

2. The shoe care device according to claim 1, further comprising a steam generator configured to supply steam to the accommodation space.

3. The shoe care device according to claim 1, wherein the controller is configured to, based on any one of the plurality of dehumidifying materials being heated, control the air supply device in a first operation mode by:
- closing a first portion of the connection path corresponding to a heated dehumidifying material among the plurality of dehumidifying materials to thereby open a first portion of the regeneration path corresponding to the heated dehumidifying material, and
- opening a second portion of the connection path corresponding to an unheated dehumidifying material among the plurality of dehumidifying materials to thereby close a second portion of the regeneration path corresponding to the unheated dehumidifying material.

4. The shoe care device according to claim 3, wherein the controller is configured to, in the first operation mode, control the air supply device to alternately heat the plurality of dehumidifying materials one after another.

5. The shoe care device according to claim 3, wherein the controller is configured to, in the first operation mode, control the air supply device to supply a first amount of air to the heated dehumidifying material and a second amount of air to the unheated dehumidifying material, the first amount of air being less than the second amount of air.

6. The shoe care device according to claim 3, wherein the controller is configured to, based on none of the plurality of dehumidifying materials being heated, control the air supply device in a second operation mode by opening the connection path to thereby close the regeneration path.

7. The shoe care device according to claim 6, wherein the controller is configured to, based on all of the plurality of dehumidifying materials being heated, control the air supply device in a third operation mode by closing the connection path to thereby open the regeneration path.

8. The shoe care device according to claim 7, further comprising a control panel configured to receive an operation signal from a user,
wherein the controller is configured to, based on the operation signal being received through the control panel, control the air supply device to perform the third operation mode for a predetermined time.

9. The shoe care device according to claim 7, further comprising a sensor configured to measure an amount of moisture adsorbed in the plurality of dehumidifying materials,
wherein the controller is configured to control the air supply device to perform the third operation mode until the amount of moisture measured by the sensor becomes less than or equal to a predetermined value.

10. The shoe care device according to claim 1, wherein the air supply device comprises:
- a plurality of chambers that are spaced apart from one another and connected to branches of the connection path, respectively, each of the plurality of chambers accommodating one of the plurality of dehumidifying materials; and
- a plurality of heaters, each of the plurality of heaters being disposed at one of the plurality of chambers and configured to heat one of the plurality of dehumidifying materials in the one of the plurality of chambers, wherein each chamber of the plurality of chambers defines:
- a drying path hole configured to discharge air having passed through the dehumidifying material in the chamber toward the inlet, and
- a regeneration path hole that is separate from the drying path hole and configured to discharge air having passed through the dehumidifying material in the chamber in a direction other than toward the inlet, wherein the air supply device further comprises a plurality of dampers that are disposed in the plurality of chambers, respectively, and configured to selectively open and close the drying path hole and the regeneration path hole of each the plurality of chambers, and wherein the controller is configured to control the plurality of dampers to selectively open and close the drying path hole and the regeneration path hole of each the plurality of chambers based on operation of at least one of the plurality of heaters.

11. The shoe care device according to claim 10, wherein the air supply device further comprises a condenser connected to the regeneration path holes and configured to condense moisture from air discharged through the regeneration path holes.

12. The shoe care device according to claim 10, wherein the controller is configured to, based on one of the plurality of heaters operating, (i) control one of the plurality of dampers to close the drying path hole corresponding to an operating heater among the plurality of heaters to thereby open the regeneration path hole corresponding to the operating heater, and (ii) control another of the plurality of dampers to open the drying path hole corresponding to a remaining heater that is not the operating heater among the plurality of heaters to thereby close the regeneration path hole corresponding to the remaining heater.

13. The shoe care device according to claim 12, wherein the controller is configured to alternately operate the plurality of heaters one after another.

14. The shoe care device according to claim 12, wherein the controller is configured to control the plurality of dampers to supply a first amount of air to one of the plurality of chambers corresponding to the operating heater and a second amount of air to another of the plurality of chambers corresponding to the remaining heater, the first amount of air being less than the second amount of air.

15. The shoe care device according to claim 10, wherein an open area of the regeneration path hole is less than an open area of the drying path hole.

16. The shoe care device according to claim 10, wherein the controller is configured to, based on none of the plurality of heaters operating, control the plurality of dampers to open the drying path holes to thereby close the regeneration path through the regeneration path holes.

17. The shoe care device according to claim 10, wherein the controller is configured to, based on all of the plurality of heaters operating, control the plurality of dampers to close the drying path holes to thereby open the regeneration path through the regeneration path holes.

18. The shoe care device according to claim 17, further comprising a control panel configured to receive an operation signal from a user,
    wherein the controller is configured to, based on the operation signal being received through the control panel, operate all of the plurality of heaters for a predetermined time.

19. The shoe care device according to claim 17, further comprising a sensor configured to measure an amount of moisture adsorbed in the plurality of dehumidifying materials,
    wherein the controller is configured to operate all of the plurality of heaters until the amount of moisture measured by the sensor becomes less than or equal to a predetermined value.

20. The shoe care device according to claim 11, wherein the air supply device further comprises:
    a blowing fan connected to the outlet and configured to blow air toward each of the plurality of chambers; and
    a drain tank connected to the condenser and configured to receive water generated from the condenser.

\* \* \* \* \*